US010000478B2

(12) United States Patent
Walensky et al.

(10) Patent No.: US 10,000,478 B2
(45) Date of Patent: *Jun. 19, 2018

(54) PYRAZOL-3-ONES THAT ACTIVATE PRO-APOPTOTIC BAX

(71) Applicant: Dana-Farber Cancer Institute, Inc., Boston, MA (US)

(72) Inventors: Loren D. Walensky, Newton Centre, MA (US); Evripidis Gavathiotis, Boston, MA (US)

(73) Assignee: Dana-Farber Cancer Institute, Inc., Boston, MA (US)

( * ) Notice: Subject to any disclaimer, the term of this patent is extended or adjusted under 35 U.S.C. 154(b) by 0 days. days.

This patent is subject to a terminal disclaimer.

(21) Appl. No.: 15/048,918

(22) Filed: Feb. 19, 2016

(65) Prior Publication Data

US 2016/0264564 A1    Sep. 15, 2016

Related U.S. Application Data

(63) Continuation of application No. 14/350,847, filed as application No. PCT/US2012/059799 on Oct. 11, 2012, now Pat. No. 9,303,024.

(60) Provisional application No. 61/546,022, filed on Oct. 11, 2011.

(51) Int. Cl.
| | |
|---|---|
| C07D 417/04 | (2006.01) |
| C07D 403/14 | (2006.01) |
| C07D 417/14 | (2006.01) |
| C07D 403/04 | (2006.01) |
| A61K 31/4155 | (2006.01) |
| A61K 31/4178 | (2006.01) |
| A61K 31/427 | (2006.01) |
| A61K 31/497 | (2006.01) |
| C07D 413/04 | (2006.01) |

(52) U.S. Cl.
CPC ........ *C07D 417/04* (2013.01); *A61K 31/4155* (2013.01); *A61K 31/4178* (2013.01); *A61K 31/427* (2013.01); *A61K 31/497* (2013.01); *C07D 403/04* (2013.01); *C07D 403/14* (2013.01); *C07D 413/04* (2013.01); *C07D 417/14* (2013.01)

(58) Field of Classification Search
CPC .................................................. C07D 417/04
See application file for complete search history.

(56) References Cited

U.S. PATENT DOCUMENTS

| | | | |
|---|---|---|---|
| 7,160,870 B2 | 1/2007 | Duffy et al. | |
| 9,303,024 B2 * | 4/2016 | Walensky | A61K 31/4155 |
| 2009/0012148 A1 | 1/2009 | Maxfield et al. | |
| 2009/0163545 A1 | 6/2009 | Goldfarb | |
| 2011/0003851 A1 | 1/2011 | Zhi et al. | |

FOREIGN PATENT DOCUMENTS

| | | |
|---|---|---|
| AR | 049472 A1 | 8/2006 |
| CN | 101343268 A | 1/2009 |
| CN | 101766602 A | 7/2010 |
| DE | 3728278 A1 | 6/1988 |
| EP | 2305250 A1 | 4/2011 |
| WO | 200174769 A1 | 10/2001 |
| WO | 2003011855 A1 | 2/2003 |
| WO | 2004014902 A2 | 2/2004 |
| WO | 2005077345 A1 | 8/2005 |
| WO | 2005077368 A2 | 8/2005 |
| WO | 2005077939 A1 | 8/2005 |
| WO | 2007053847 A2 | 5/2007 |
| WO | 2009071701 A1 | 6/2009 |
| WO | 2011029046 A1 | 9/2009 |
| WO | 2009130242 A1 | 10/2009 |
| WO | 2010042225 A2 | 4/2010 |

OTHER PUBLICATIONS

Chemical Abstracts Registry No. 331244-88-3, indexed in the Registry file on STN CAS Online on Apr. 13, 2001.*
Chemical Abstracts Registry No. 314290-35-2, indexed in the Registry file on STN CAS Online on Jan. 17, 2001.*
Chemical Abstracts Registry No. 314290-60-3, indexed in the Registry file on STN CAS Online on Jan. 17, 2001.*
Chemical Abstracts Registry No. 314290-78-3, indexed in the Registry file on STN CAS Online on Jan. 17, 2001.*
Chemical Abstracts Registry No. 314761-59-6, indexed in the Registry file on STN CAS Online on Jan. 18, 2001.*
Chemical Abstracts Registry No. 314761-79-0, indexed in the Registry file on STN CAS Online on Jan. 18, 2001.*
An English translation of CN 101343268 A, Jan. 14, 2009.*
Adam, et al., *Synthesis and studies of TH(IV) and Ce(III) complexes with some azopyrazolone compounds*, Delta Journal of Science, 11(3):1089-103 (1987).
Amir, et al., *Synthesis and antimicrobial activity of pyrazolinones and pyrazoles having benzothiazole moiety*, Med Chem Res, 21:1261-1270 (2012).
Atta, Aly H., *Reactions of 1-(2-benzothiazolyl)-4-(dicyanomethylene)-3-methyl-2-pyrazolin-5-one towards amines*, Heterocyclic Communications, 5(3):243-247 (1999).
Baell, et al., *New Substructure Filters for Removal of Pan Assay Interference Compounds (PAINS) from Screening Libraries and for Their Exclusion in Bioassays*, J Med Chem, 53(7):2719-2740 (2010).
Bondock, et al., *Ecofriendly solvent-free synthesis of thiazolylpyrazole derivatives*, Monatshefte fuer Chemie 139(11):1329-1335 (2008).

(Continued)

Primary Examiner — Laura L Stockton
(74) Attorney, Agent, or Firm — Fish & Richardson P.C.

(57) ABSTRACT

This application features pyrazol-3-one compounds that activate pro-apoptotic BAX. Also featured are methods of using such compounds, e.g., for the treatment or prevention of diseases, disorders, and conditions associated with deregulated apoptosis of cells (e.g., insufficient apoptosis of diseased or damaged cells or essentially the absence of apoptosis of diseased or damaged cells).

28 Claims, 65 Drawing Sheets

(56) References Cited

OTHER PUBLICATIONS

Chemical Abstracts Registry No. 314292-25-6, indexed in the Registry file on STN CAS Online Jan. 17, 2001.
Chemical Abstracts Registry No. 314293-69-1, indexed in the Registry file on STN CAS Online Jan. 17, 2001.
Chemical Abstracts Registry No. 314293-18-0, indexed in the Registry file on STN CAS Online Jan. 17, 2001.
Chemical Abstracts Registry No. 7104-71-4, indexed in the Registry file on STN CAS Online Nov. 16, 1984.
Efros, et al., *Benzothiazole derivatives. Preparation of 1-benzothiazolyl-3-methyl-5(4H)-pyrazolone.* Zhurnal Obshchei Khimii, 21:2046-50 (1951).
El-Haty, *A Co-ordination and stability study on some heterocyclic azopyrazolin-5-ones with Y(III), La(III), Ce(III) and $UO_2^{2+}$ ions*, Journal of the Electrochemical Society of India, 40(3):113-18 (1991).
Emandi, et al., *1-(2-Benzothiazolyl)-3-methyl-5-pyrazolone-based dyes*, Revistade Chimie (Bucharest, Romania) 45(3):179-82 (1994) [with English Abstract].
Erickson-Miller et al., *Preclinical Activity of Eltromboapag (SB-497115), an Oral, Nonpeptide Thrombopoietin Receptor Agonist*, Stem Cells, 27:424-430 (2009).
Gavathiotis et al., "Direct and selective small-molecule activation of proapoptotic BAX", Nature Chemical Biology, 8(7):639-645 (May 2012).
Ibrahim, et al., *Synthesis of pyrazoles and fused pyrazoles. Novel synthesis of pyrano[2,3-c]pyrazole, thieno[2,3-c]pyrazole and pyrazolo[3, 4-b]pyridine derivatives*, Journal of the Indian Chemical Society, 74(3):206-208 (1997).
Kalluraya, et al., *Synthesis of some triheterocyclic thiazole derivatives of biological interest*, Indian Journal of Heterocyclic Chemistry, 8(3):241-242 (1999).
Mahesh, et al., *Separation of some closely related 1-(2-benzothiazolyl)-3-methyl-4-arylhydrazono-pyrazoline-5-one derivatives by thin layer chromatography*, Fresenius' Zeitschrift fuer Analytische Chemie, 309(5):404 (1981).
Mamedov, et al., *Reactions of Isomeric Arylchloropyruvates and Glycidates with Hydrazines*, Russian Journal of Organic Chemistry, 41(5):694-702 (2005).
Naylor, et al., *Identification of a chemical probe for NAACP by virtual screening*, Nature Chemical Biology 5(4):220-226 (2009).
Parija, et al., *Preparation of azamerocyanines and evaluation of the effect of introduction of nitrogen atom in the chromophoric chain*, Journal of the Indian Chemical Society, 47(12):1129-34 (1970).
Patel, et al., *Synthesis and biological evaluation of some new pyrazolones and imidazolinones*, Oriental Journal of Chemistry 19(2):435-440 (2003), Abstract Only.
Ren et al., "BID, BIM, and PUMA Are Essential for Activation of the BAX- and BAK-Dependent Cell Death Program", Science, 330(6009):1390-1393 (Dec. 2010).
Rosenbaum et al., *Chemical screen to reduce sterol accumulation in Niemann—Pick C disease cells identifies novel lysosomal acid lipase inhibitors*, Biochimica et Biophysica Acta, Molecular and Cell Biology of Lipids, 1791(12), 1155-1165 (2009).
Rout, M.K., *Influence of structural changes on absorption. Merocyanine dyes and aza-analogues of merocyanines, unsymmetrical cyanines, and p-dialkylamino styryl dyes*, Jour. & Proc. Inst. Chem., (India), 35(3):117-130 (1963).
Chemical Structure Search Report by Science IP, dated Oct. 9, 2012 (49 pages).
EP Patent Office, Partial Supplementary European Search Report, for EP Application No. 12840731.9-1453/2766355 PCT/US2012059799, dated Jan. 18, 2015.
International Search Report for PCT/US2012/059799 dated Mar. 13, 2013, 4 pages.
Examination Report in Australian Pat. App. No. 2012322660, dated Jul. 8, 2016 (4 pages).

* cited by examiner

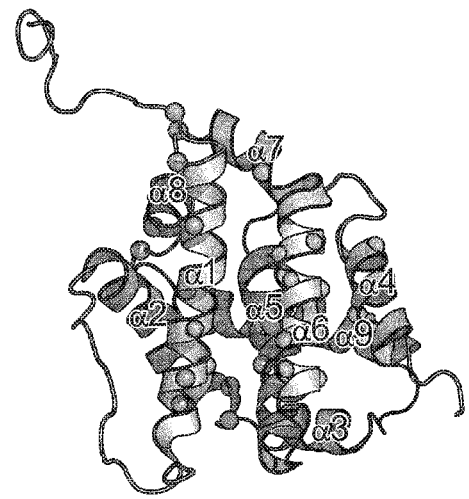
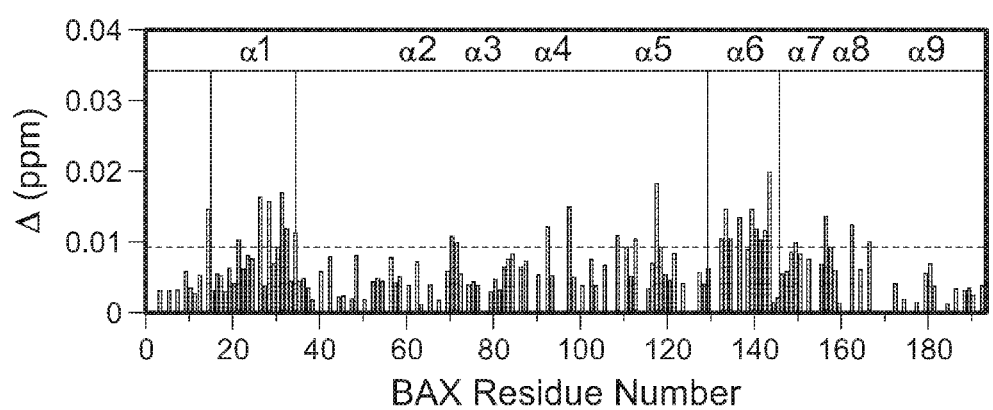
FIG. 6A

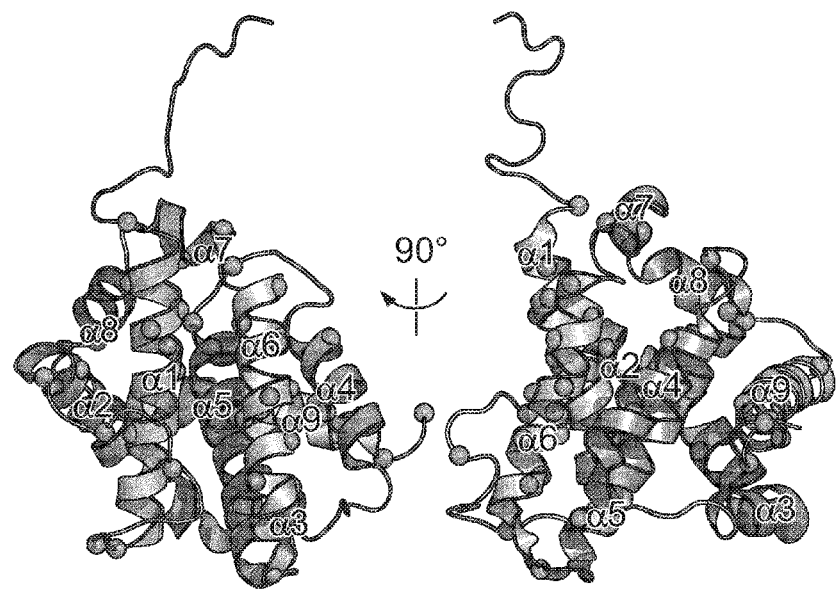
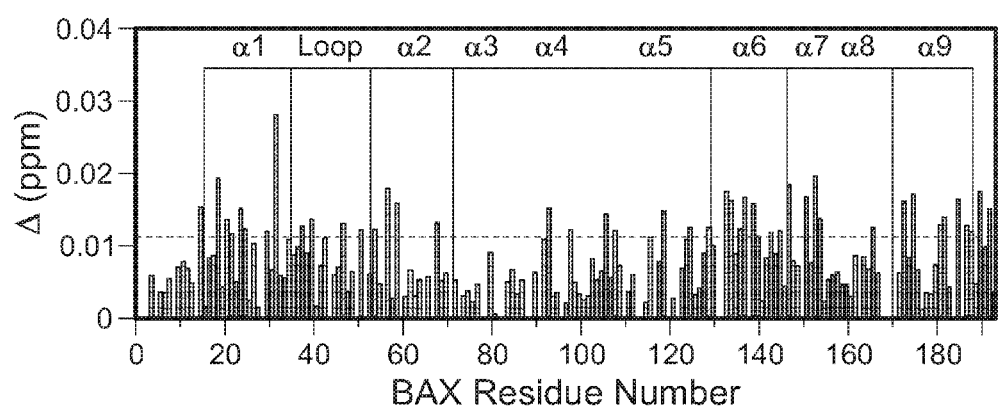
FIG. 7

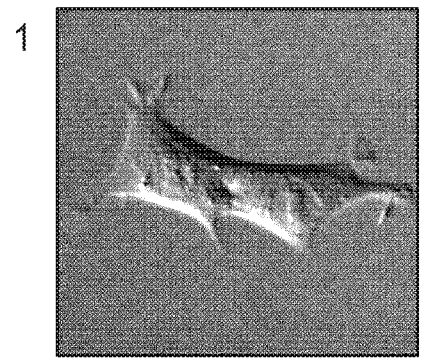
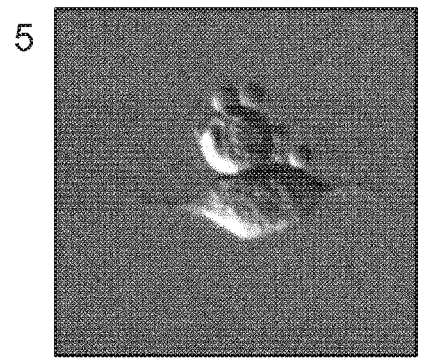
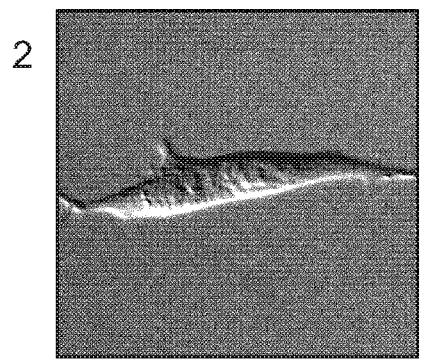
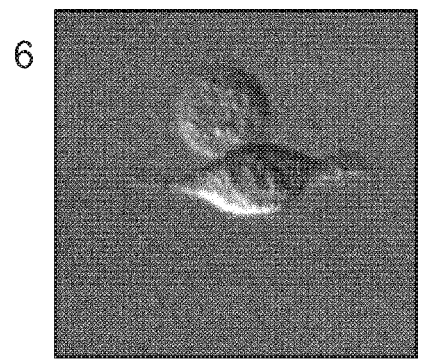
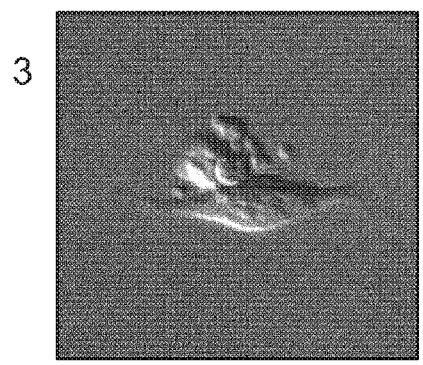
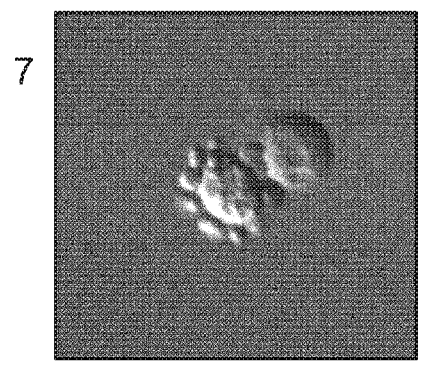
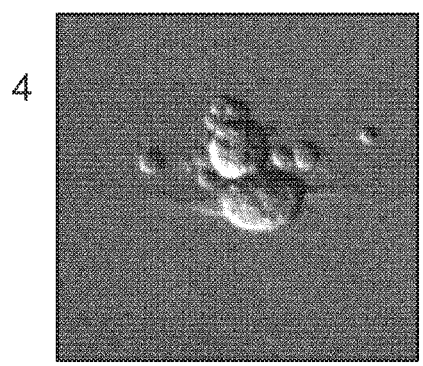
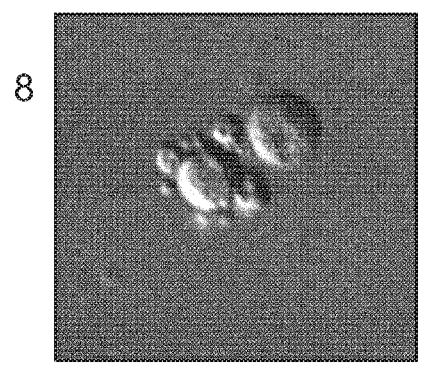
FIG. 8E

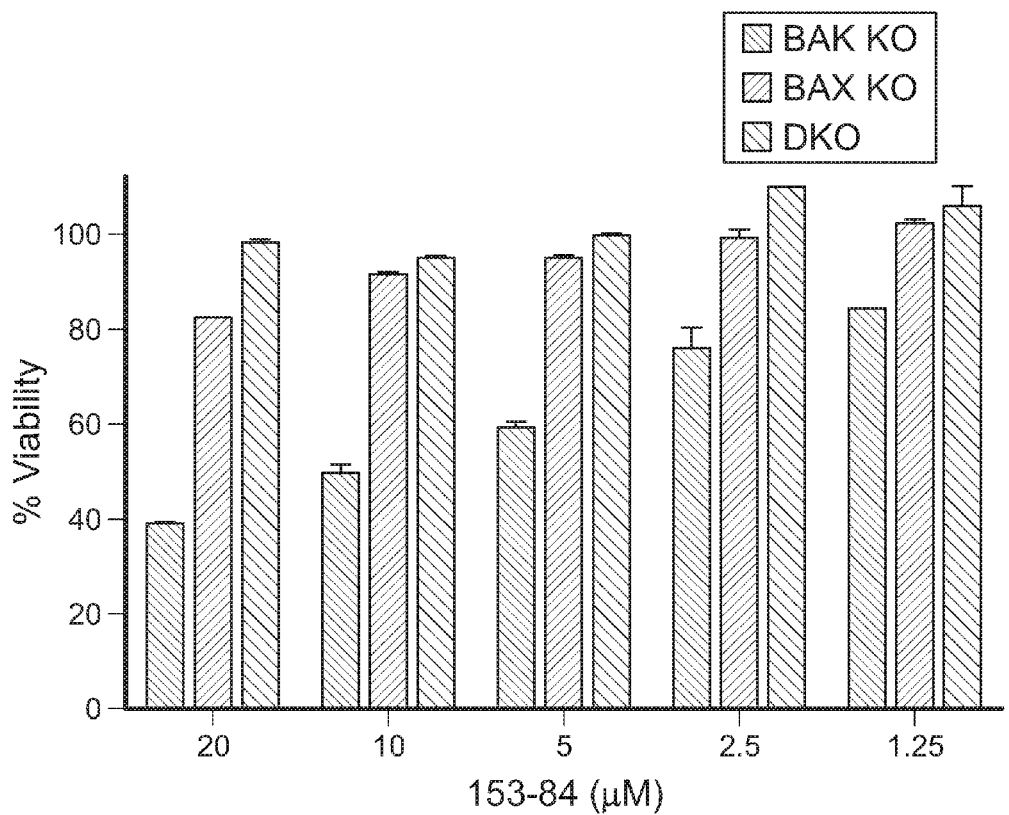
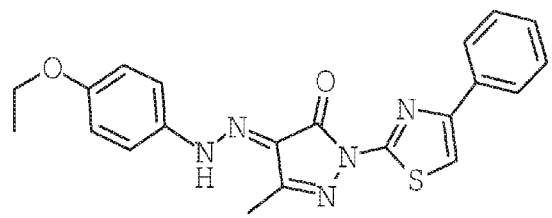
FIG. 9A

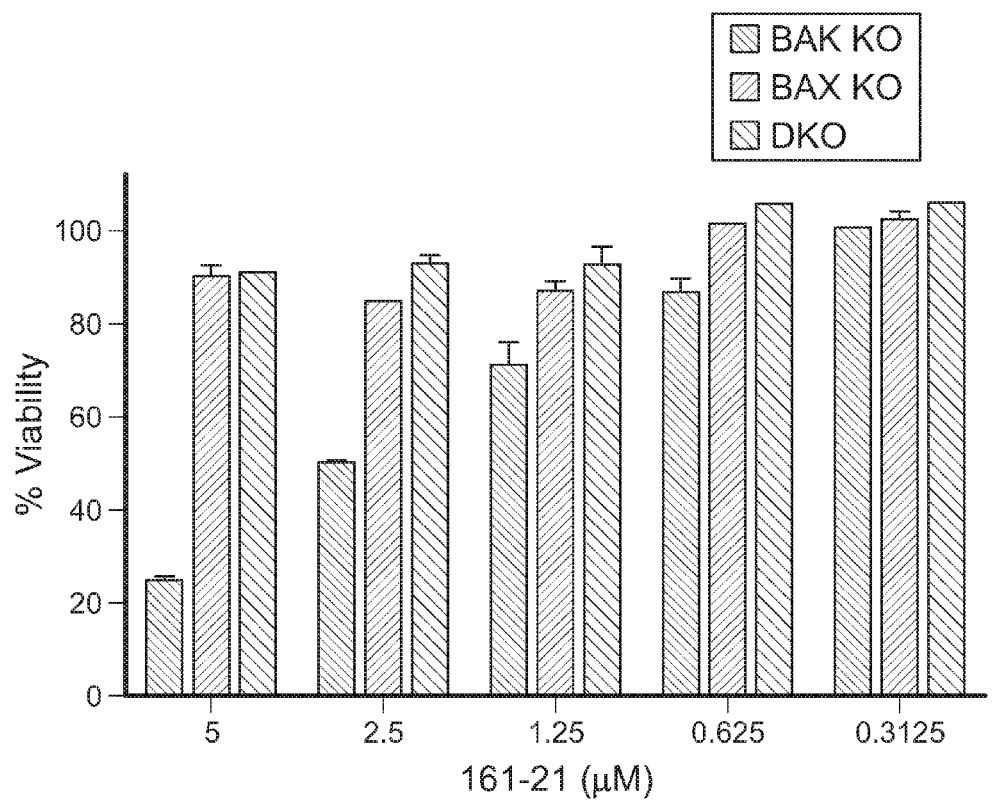
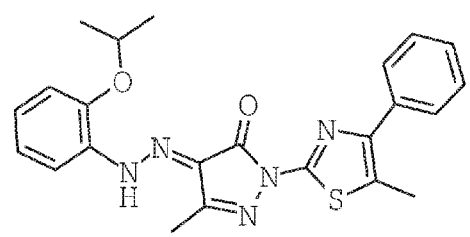
FIG. 9B

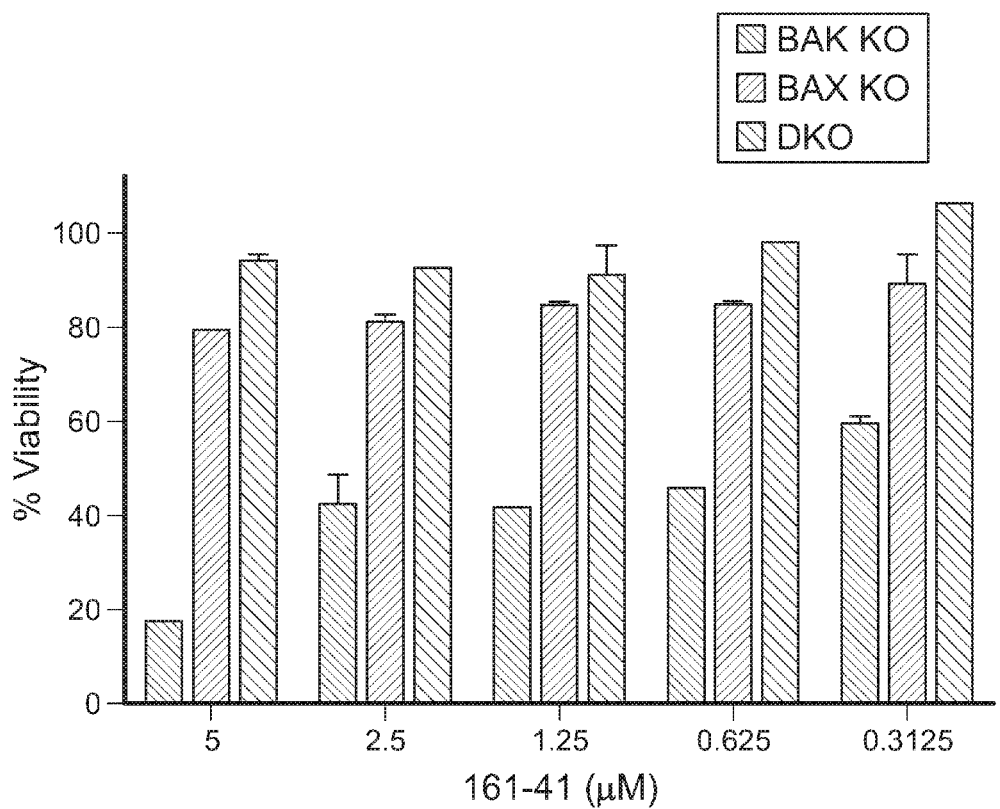
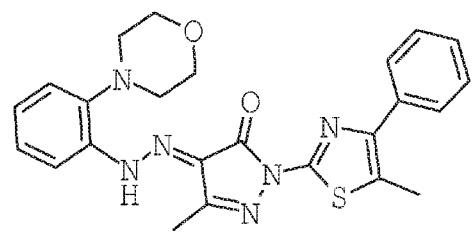
FIG. 9C

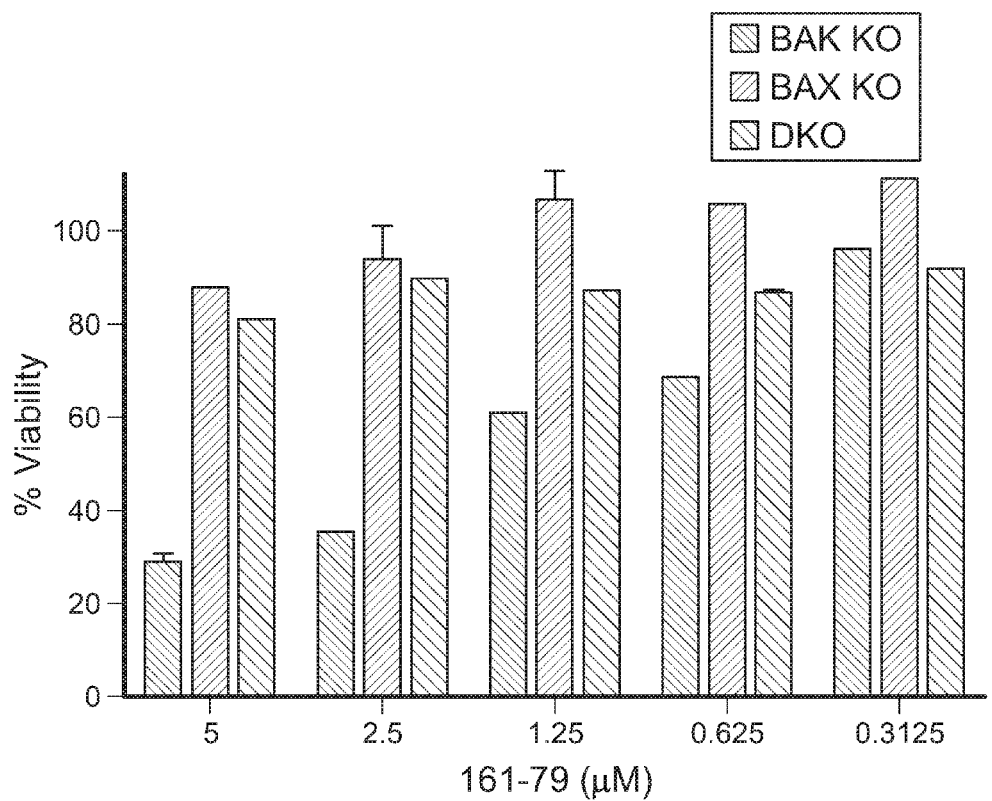
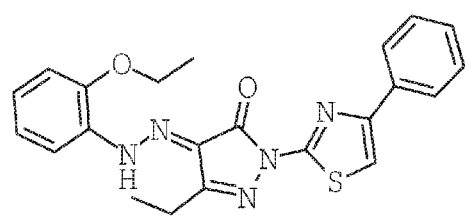
FIG. 9D

| Structure | Code | MW | IC50 (μM) |
|---|---|---|---|
| 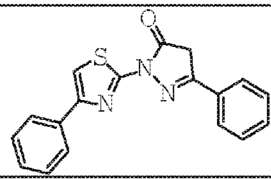 | 153-04 | 319.4 | 60 |
| 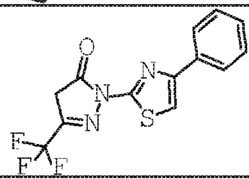 | 153-19 | 311.3 | No binding |
| 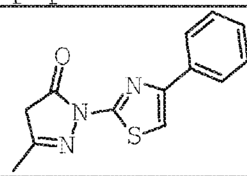 | 153-18 | 257.3 | No binding |
| 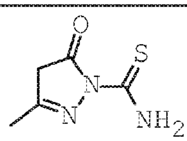 | 153-21 | 157.2 | No binding |
| 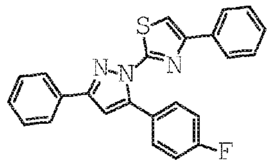 | 153-26 | 397.5 | 67 |
| 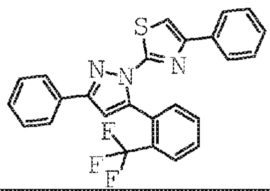 | 153-31 | 447.5 | 40 |
| 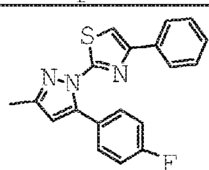 | 153-37 | 335.4 | 93 |
| 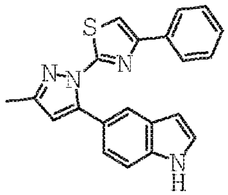 | 153-38 | 356.4 | 20-40 |

FIG. 11

| Structure | ID | MW | Value |
|---|---|---|---|
| (structure) | 153-32 | 418.5 | No binding |
| (structure) | 153-39 | 385.4 | No binding |
| (structure) | 153-40 | 313.4 | No binding |
| (structure) | 153-44 | 365.5 | 157 |
| (structure) | 153-47 | 395.5 | 44 |
| (structure) | 153-48 | 457.6 | 20-50 |
| (structure) | 153-49 | 427.5 | 52 |
| (structure) | 153-50 | 494.6 | No binding |

FIG. 11 (Cont.)

| Structure | ID | MW | Value |
|---|---|---|---|
| 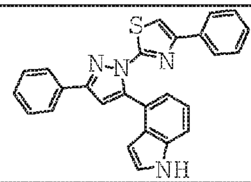 | 153-51 | 418.5 | No binding |
| 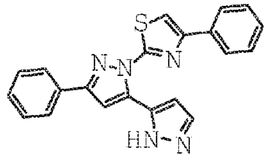 | 153-53 | 369.4 | No binding |
| 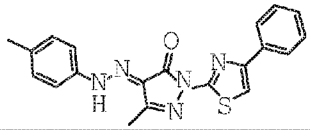 | 153-74 | 375.4 | 27.5 |
| 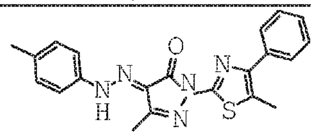 | 153-80 | 389.5 | 9.5 |
| 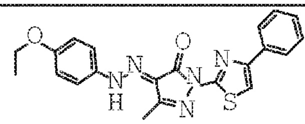 | 153-84 | 405.5 | 15 |
| 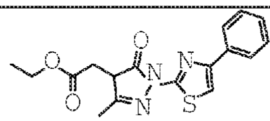 | 153-86-3 | 343.4 | 100 |
| 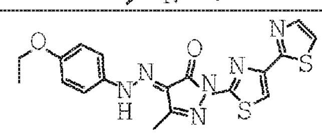 | 153-92 | 412.5 | 30 |
| 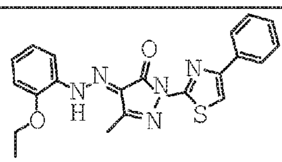 | 153-95 | 405.5 | 27 |
| 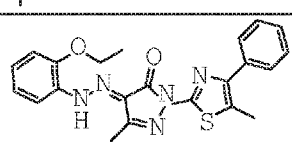 | 153-96 | 419.5 | 2-6 |
| 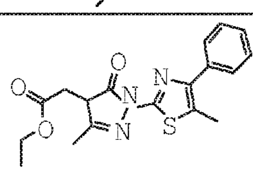 | 153-97 | 357.4 | No binding |

FIG. 11 (Cont.)

| Structure | ID | MW | Binding |
|---|---|---|---|
| 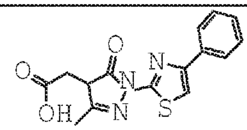 | 153-99 | 315.3 | No binding |
| 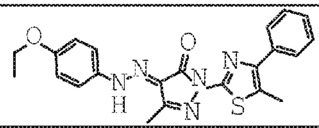 | 161-04 | 419.5 | 15 |
| 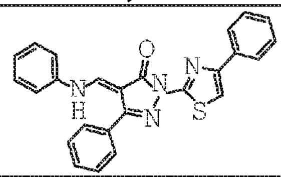 | 161-08 | 422.5 | 50 |
| 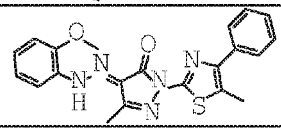 | 161-12 | 405.5 | 43 |
| 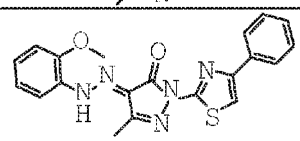 | 161-13 | 391.4 | >100 |
| 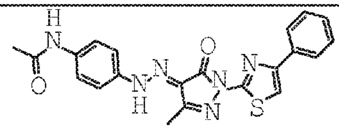 | 161-23 | 418.5 | >100 |
| 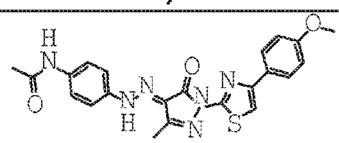 | 161-24 | 448.5 | 76 |
| 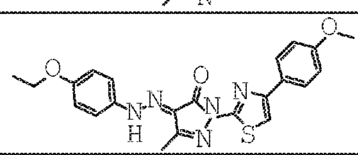 | 161-26 | 435.5 | >100 |
| 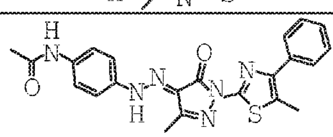 | 161-22 | 432.5 | 15 |
| 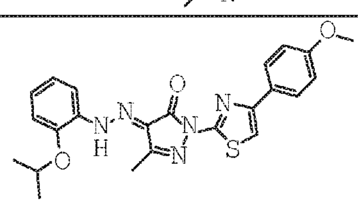 | 161-25 | 449.5 | 97 |

FIG. 11 (Cont.)

| Structure | ID | MW | IC50 |
|---|---|---|---|
| 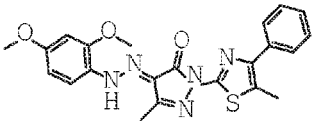 | 161-30 | 435.5 | 54 |
| 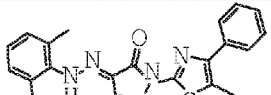 | 161-31 | 403.5 | >100 |
| 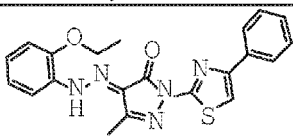 | 153-95 | 405.5 | 15 |
| 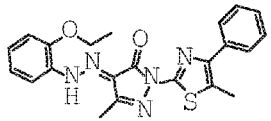 | 153-96 | 419.5 | 2 |
| 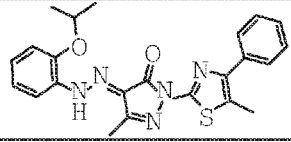 | 161-21 | 433.2 | 1.6 |
| 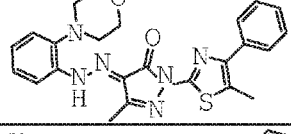 | 161-41 | 460.6 | 4.6 |
| 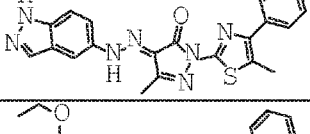 | 161-46 | 405.5 | 7.2 |
| 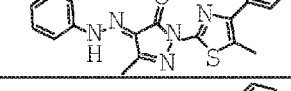 | 161-49 | 419.5 | >100 |
| 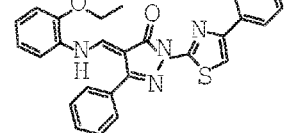 | 161-51 | 466.6 | 44 |
| 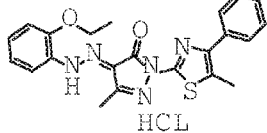 | 161-62 | 456 | 1.5 |
FIG. 11 (Cont.)

| Structure | ID | MW | Value |
|---|---|---|---|
| 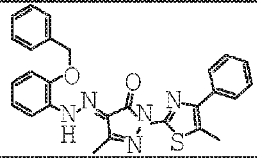 | 161-67 | 481.6 | No binding |
| 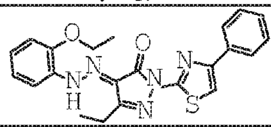 | 161-79 | 419.5 | 6.2 |
| 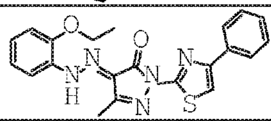 | 161-91 | 405.5 | 2 |
| 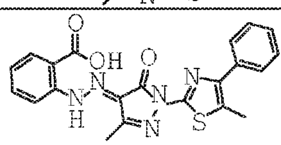 | 161-86 | 419.5 | 1.4 |
| 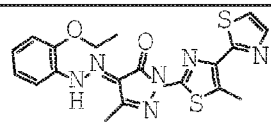 | 161-87 | 426.5 | 2.4 |
| 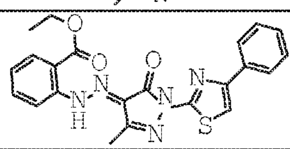 | 165-17 | 433.5 | No binding |
| 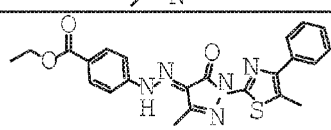 | 165-09 | 448 | 6 |
| 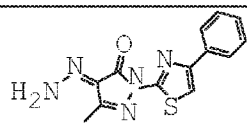 | 165-15 | 285.3 | 7.5 |
| 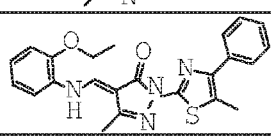 | 165-18 | 418.5 | 12 |
| 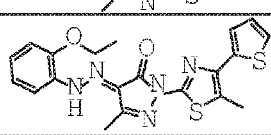 | 165-19 | 425.5 | 10 |
| 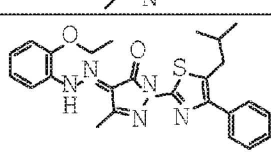 | 165-7 | 461.6 | 9 |

FIG. 11 (Cont.)

| Structure | Compound | MW | Value |
|---|---|---|---|
| 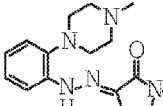 | 161-56 | 433.5 | 7.9 |
| 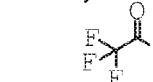 | 165-28 | 570.6 | 5.4 |
| 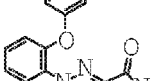 | 165-42 | 467.5 | 30 |
| 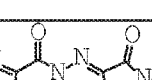 | 165-45 | 396.0 | 7.6 |
| 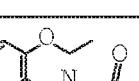 | 165-53 | 481.0 | 5 |
| 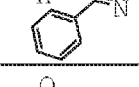 | 165-60 | 467.1 | 0.9 |
| 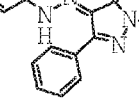 | 165-62 | 497.2 | <70 |
| 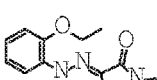 | Eltrombopag | 442.5 | 0.25 |
FIG. 11 (Cont.)

| Structure | ID | MW | Value |
|---|---|---|---|
| (structure) | 165-74 | 467.0 | 0.22 |
| (structure) | 165-75 | 505.0 | No binding |
| (structure) | 165-85 | 421 | 10 |
| (structure) | 165-86 | 481 | 0.5 |
| (structure) | 165-86-1 | 481.1 | 0.75 |
| (structure) | 165-86-2 | 591.1 | 2.2 |
| (structure) | 165-87 | 473 | 0.1 |
| (structure) | 165-92 | 379 | No binding |
| (structure) | 165-93 | 388 | 0.5-1 |

FIG. 11 (Cont.)

| Structure | ID | MW | Value |
|---|---|---|---|
| 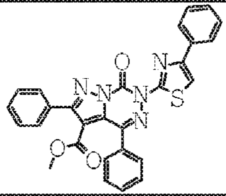 | 165-90 | 505.55 | No binding |
| 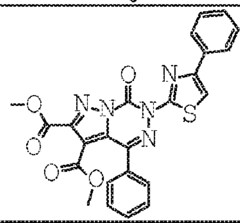 | 165-94 | 487.49 | >20 |
| 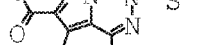 | 165-95 | 429.45 | >30 |
| 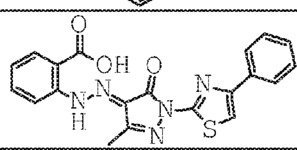 | 165-97 | 405.43 | 1.7 |
| 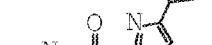 | 172-02 | 491.61 | 6 |
| 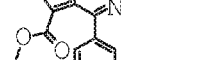 | 172-11 | 545.66 | 1.5 |
| 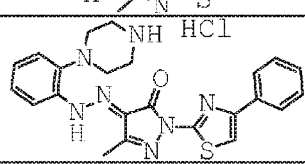 | 172-19 | 482 | 2.7 |
| 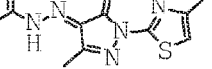 | 172-22 | 457.46 | |
FIG. 11 (Cont.)

| Structure | ID | Mass |
|---|---|---|
| (structure) | 172-8 | 516.62 |
| (structure) | 172-28 | 490.62 |
| (structure) | 172-29 | 476.5 |

FIG. 11 (Cont.)

| Structure | ID | Name |
|---|---|---|
| (H3C-O-C6H4)-NH-N=... pyrazolone-thiazole-phenyl | 5258079 | |
| benzimidazole dimer with NH2 groups | 5180073 | AN-BAM 1 |
| (HOOC-C6H4)-NH-N=... pyrazolone-thiazole-phenyl | 5256949 | ANA-BAM 2 |
| (HOOC-C6H4)-N=N-... pyrazolone-thiazole-(4-methoxyphenyl) | 5257582 | ANA-BAM 3 |
| (HO-C6H4)-NH-N=... pyrazolone-thiazole-phenyl | 5259941 | ANA-BAM 4 |
| (HO-C6H4)-N=N-... pyrazolone-thiazole-(4-methylphenyl) | 5260500 | ANA-BAM 5 |
| (Cl-C6H4)-NH-N=... pyrazolone-thiazole-phenyl | 5261856 | ANA-BAM 6 |

FIG. 12

| Structure | CID | Name |
|---|---|---|
| 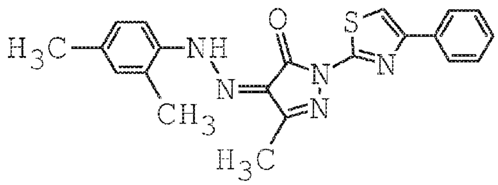 | 5262094 | ANA-BAM 7 |
| 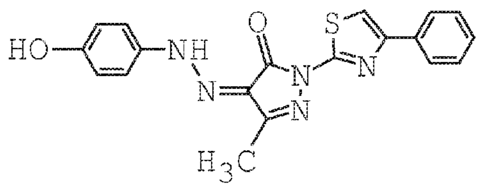 | 5267338 | ANA-BAM 8 |
| 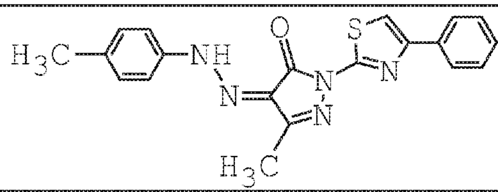 | 5269167 | ANA-BAM 9 |
| 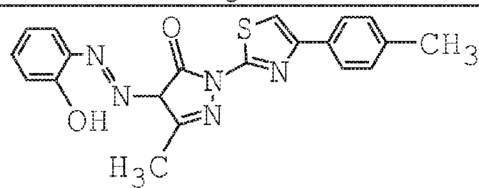 | 5270356 | ANA-BAM 10 |
| 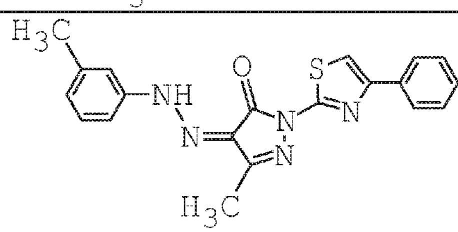 | 5270896 | ANA-BAM 11 |
| 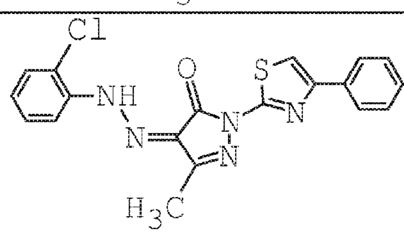 | 5271978 | ANA-BAM 12 |
| 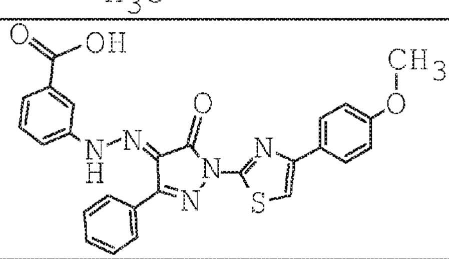 | 5647645 | ANA-BAM 13 |

FIG. 12 (Cont.)

| Structure | | |
|---|---|---|
| (Cl-phenyl-NH-N=pyrazolone-CH3, N-thiazole-phenyl) | 5278089 | ANA-BAM 14 |
| (ethyl ester-phenyl-NH-N=pyrazolone-CH3, N-thiazole-phenyl) | 5284438 | ANA-BAM 15 |
| (HOCH2-phenyl-N=N-pyrazolone-CH3, N-thiazole-phenyl-Br) | 5646979 | ANA-BAM 16 |
| (thiazole-NH-N=pyrazolone-phenyl, N-thiazole-phenyl-OCH3) | 5647019 | ANA-BAM 17 |
| (OH-phenyl-N=N-pyrazolone-CH3, N-thiazole-phenyl-Br) | 5647028 | ANA-BAM 18 |
| (HOCH2-phenyl-N=N-pyrazolone-CH3, N-thiazole-phenyl-OCH3) | 5647029 | ANA-BAM 19 |

FIG. 12 (Cont.)

| | | |
|---|---|---|
| 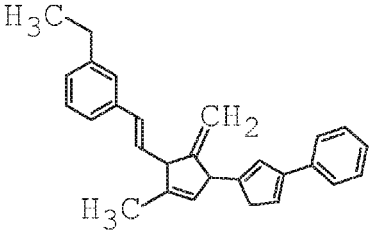 | 5647182 | ANA-BAM 20 |
| 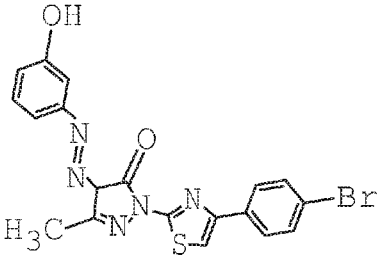 | 5647191 | ANA-BAM 21 |
| 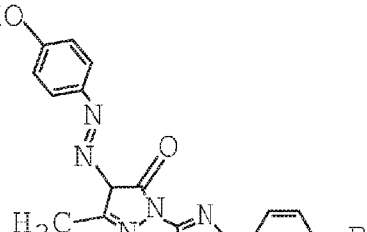 | 5647601 | ANA-BAM 22 |
| 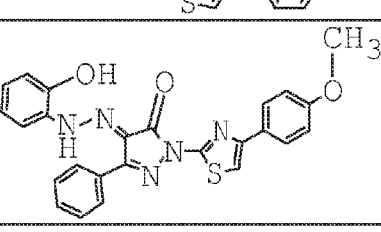 | 5647618 | ANA-BAM 23 |
| 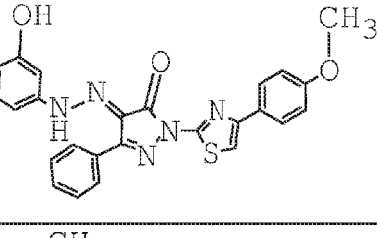 | 5647643 | ANA-BAM 24 |
| 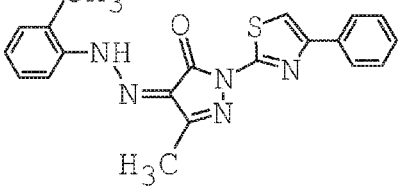 | 5274742 | ANA-BAM 25 |
FIG. 12 (Cont.)

| | | |
|---|---|---|
| 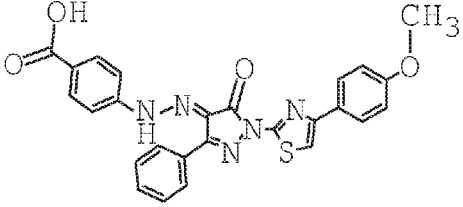 | 5647655 | ANA-BAM 26 |
| 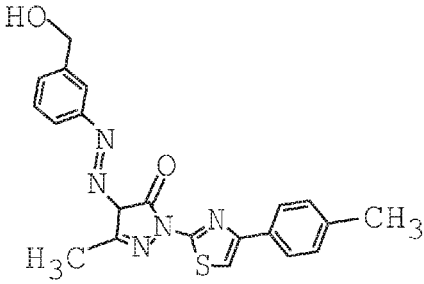 | 5647765 | ANA-BAM 27 |
| 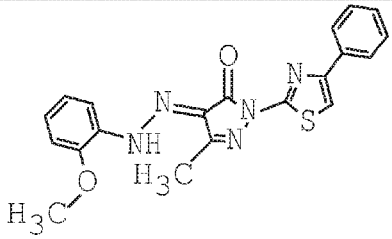 | 5705788 | ANA-BAM 28 |
| 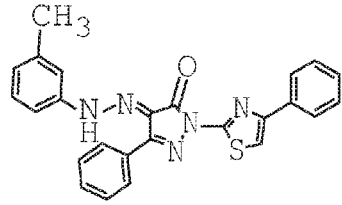 | 5705806 | ANA-BAM 29 |
| 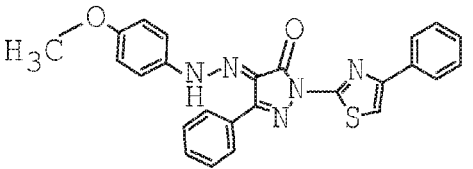 | 5705808 | ANA-BAM 30 |
| 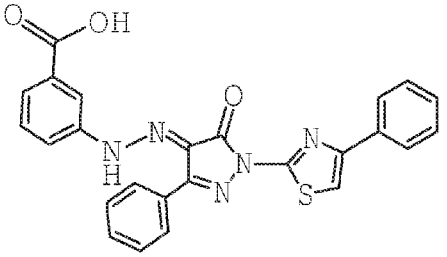 | 5705811 | ANA-BAM 31 |
FIG. 12 (Cont.)

| | | |
|---|---|---|
| 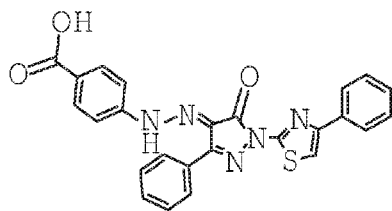 | 5705812 | ANA-BAM 32 |
| 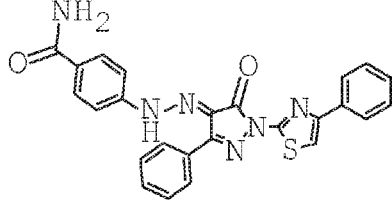 | 5705813 | ANA-BAM 33 |
| 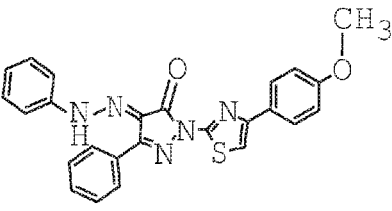 | 5705814 | ANA-BAM 34 |
| 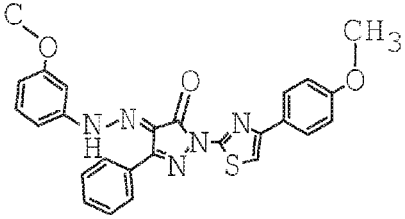 | 5705815 | ANA-BAM 35 |
| 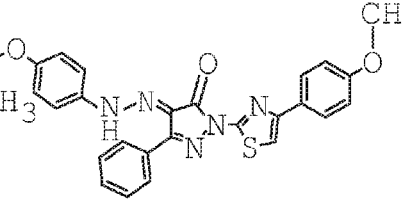 | 5705816 | ANA-BAM 36 |
| 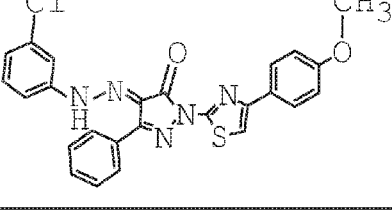 | 5705817 | ANA-BAM 37 |
FIG. 12 (Cont.)

| | | |
|---|---|---|
| 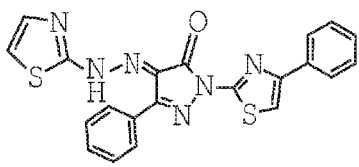 | 5705824 | ANA-BAM 38 |
| 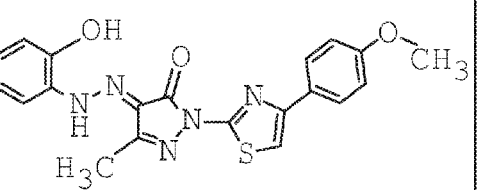 | 5705844 | ANA-BAM 39 |
| 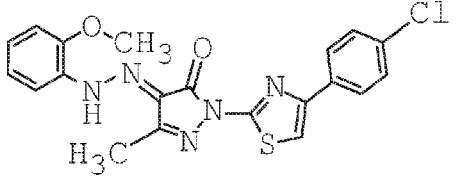 | 5705849 | ANA-BAM 40 |
| 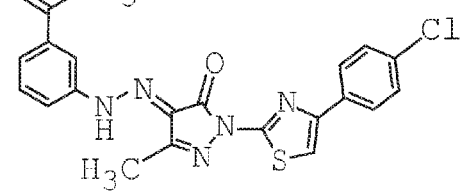 | 5705850 | ANA-BAM 41 |
| 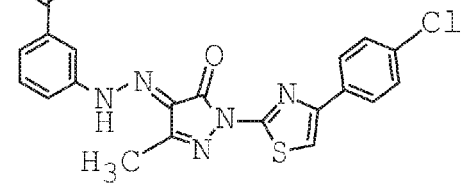 | 5705851 | ANA-BAM 42 |
| 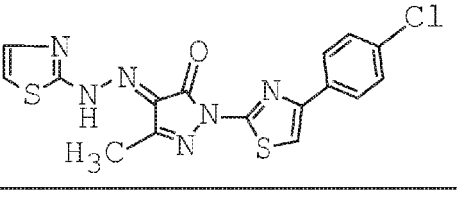 | 5705852 | ANA-BAM 43 |
FIG. 12 (Cont.)

| Structure | ID | Name |
|---|---|---|
| 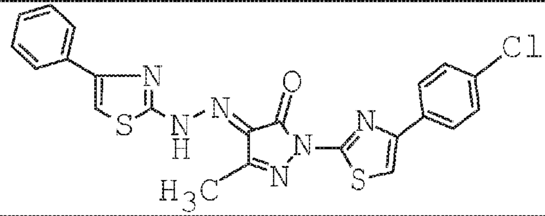 | 5705853 | ANA-BAM 44 |
| 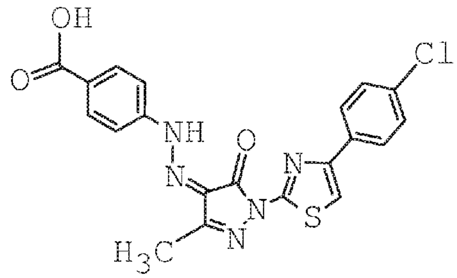 | 5708460 | ANA-BAM 45 |
| 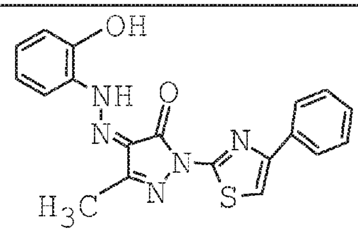 | 5709214 | ANA-BAM 46 |
| 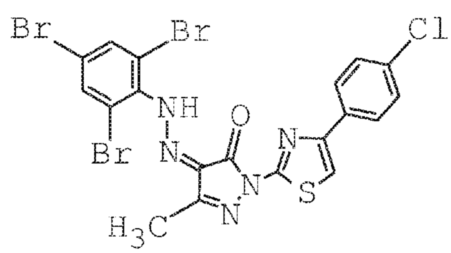 | 5713675 | ANA-BAM 47 |
| 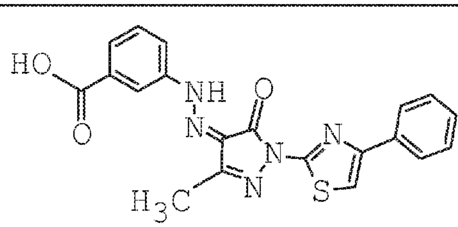 | 5714543 | ANA-BAM 48 |
| 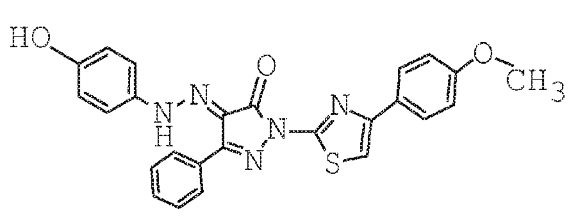 | 5719952 | ANA-BAM 49 |

FIG. 12 (Cont.)

| Structure | ID | Name |
|---|---|---|
| 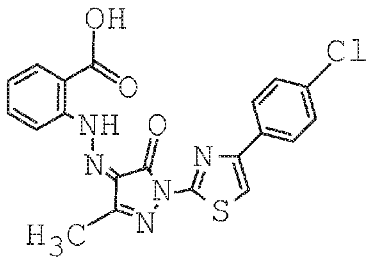 | 5720534 | ANA-BAM 50 |
| 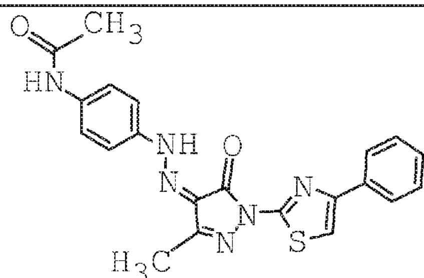 | 5724596 | ANA-BAM 51 |
| 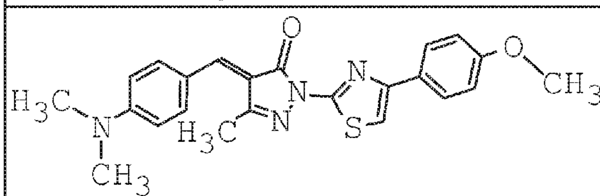 | 5725541 | ANA-BAM 52 |
| 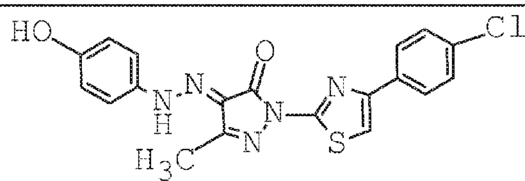 | 5725688 | ANA-BAM 53 |
| 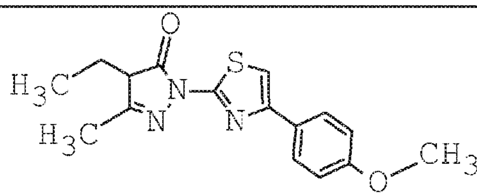 | 5844931 | ANA-BAM 54 |
| 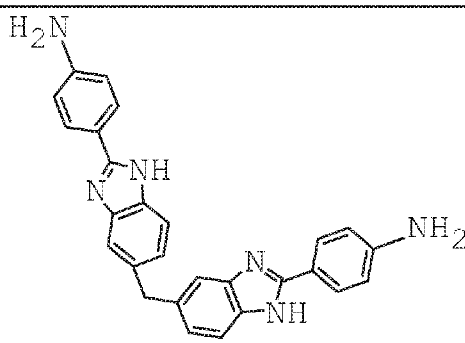 | 7609381 | ANA-BAM 55 |

FIG. 12 (Cont.)

| Compound | Code |
|---|---|
| (structure) | 165-87 |
| (structure) | 172-32 |
| (structure) | 165-74 |
| (structure) | 172-22 |
| (structure) | ANA-38 |

FIG. 14

| Structure | ID |
|---|---|
| (structure with NH2-ethoxy-phenyl hydrazone pyrazolone methyl thiazole phenyl) | 172-90 |
| (structure with 2-ethoxyphenyl hydrazone pyrazolone methyl imidazole phenyl) | 165-93 |
| (structure with 2-ethoxyphenyl hydrazone pyrazolone thiophene thiazole phenyl) | 183-50 |
| (structure with 2-ethoxyphenyl hydrazone pyrazolone phenyl thiazole phenyl) | 165-60 |
| (structure with piperazinyl-phenyl hydrazone pyrazolone methyl thiazole phenyl, HCL) | 172-19 |
| (structure with 2-carboxyphenyl hydrazone pyrazolone methyl thiazole phenyl) | 165-97 |

FIG. 14 (Cont.)

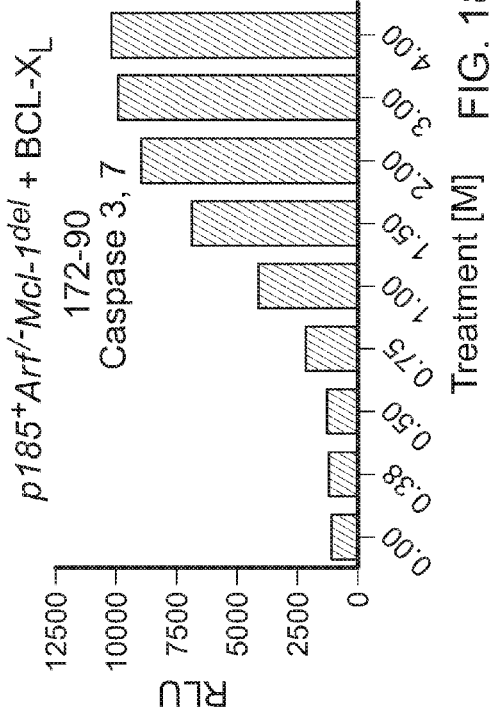
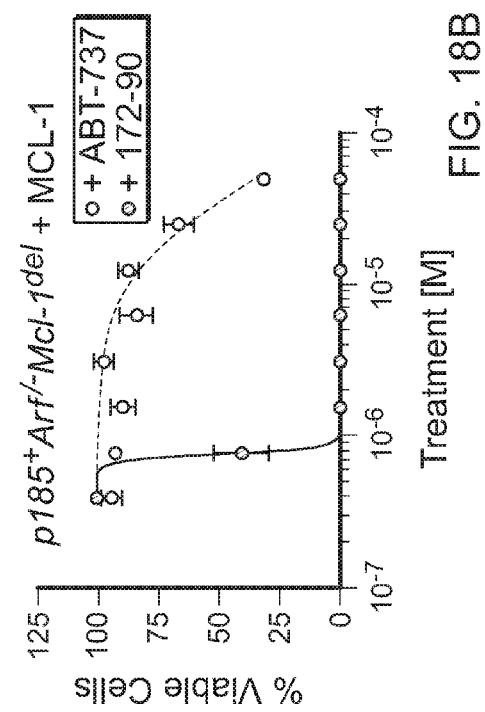
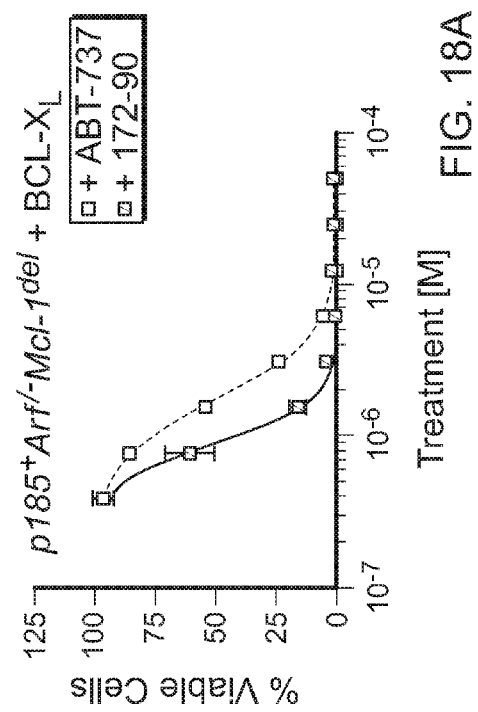
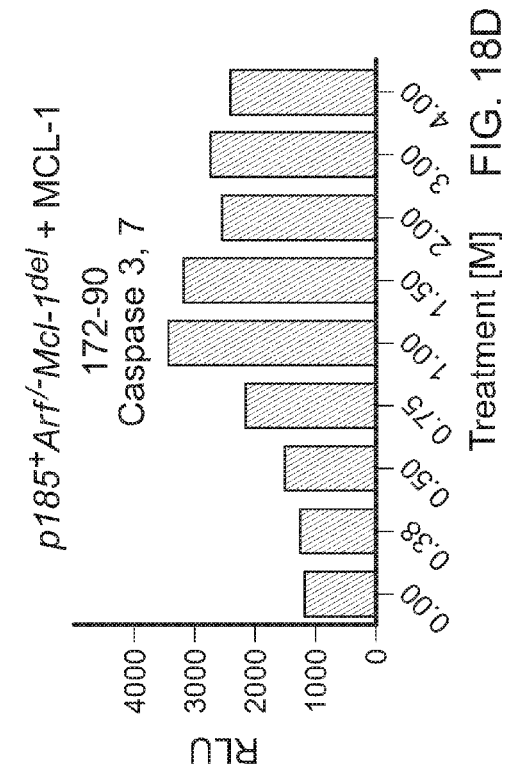

PYRAZOL-3-ONES THAT ACTIVATE PRO-APOPTOTIC BAX

CROSS REFERENCE TO RELATED APPLICATIONS

This is a continuation of U.S. Utility application Ser. No. 14/350,847, filed Apr. 10, 2014, which is a U.S. National Phase application under 35 U.S.C. § 371 of International Patent Application No. PCT/US2012/059799, filed Oct. 11, 2012, which claims the benefit of U.S. Provisional Application No. 61/546,022, filed on Oct. 11, 2011, all of which are incorporated by reference herein.

TECHNICAL FIELD

This application features pyrazol-3-one compounds that activate a pro-apoptotic function of BAX. Also featured are methods of using such compounds, e.g., for the treatment or prevention of diseases, disorders, and conditions associated with deregulated apoptosis of cells (e.g., diseased or damaged cells; e.g., insufficient apoptosis of diseased or damaged cells or reduced apoptosis of diseased or damaged cells). Examples of such diseases, disorders, and conditions include, but are not limited to, those associated with blockade(s) of cell death pathways (e.g., over-expression of anti-apoptotic BCL-2 proteins), e.g., hyperproliferative diseases, such as cancer.

BACKGROUND

BCL-2 family proteins are key regulators of the mitochondrial apoptotic pathway in health and disease. The BCL-2 family includes both pro-apoptotic (e.g., BAX) and anti-apoptotic proteins that form a complex protein interaction network of checks and balances that dictate cell fate (see, e.g., Danial, N. N. & Korsmeyer, S. J. Cell death: critical control points. *Cell* 116, 205-19 (2004)).

The α-helical BCL-2 homology 3 (BH3) domains of pro-apoptotic members (e.g., BAX) function as death ligands. Pro-apoptotic member BAX is an executioner protein of the BCL-2 family that, when activated, undergoes a structural transformation, which converts it from an inactive cytosolic monomer into a lethal mitochondrial pore (see Gavathiotis, E., Reyna, D. E., Davis, M. L., Bird, G. H. & Walensky, L. D. BH3-triggered structural reorganization drives the activation of proapoptotic BAX. *Mol Cell* 40, 481-92 (2010)).

Oligomerization of BAX (and its close homologue BAK) within the mitochondrial outer membrane enables the release of apoptogenic factors such as cytochrome c and smac/diablo that turn on caspases, the enzymatic effectors of apoptosis (see Liu, X., Kim, C. N., Yang, J., Jemmerson, R. & Wang, X. Induction of apoptotic program in cell-free extracts: requirement for dATP and cytochrome c. *Cell* 86, 147-57 (1996); Li, P. et al. Cytochrome c and dATP-dependent formation of Apaf-1/caspase-9 complex initiates an apoptotic protease cascade. *Cell* 91, 479-89 (1997); Du, C., Fang, M., Li, Y., Li, L. & Wang, X. Smac, a mitochondrial protein that promotes cytochrome c-dependent caspase activation by eliminating IAP inhibition. *Cell* 102, 33-42 (2000); Wei, M. C. et al. Proapoptotic BAX and BAK: a requisite gateway to mitochondrial dysfunction and death. *Science* 292, 727-30 (2001)). The explicit mechanism by which BAX is triggered and how select pro-apoptotic BCL-2 proteins directly engage and activate BAX have been key questions in the apoptosis field (see, e.g., Youle, R. J. & Strasser, A. The BCL-2 protein family: opposing activities that mediate cell death. *Nat Rev Mol Cell Biol* 9, 47-59 (2008)).

The α-helical BCL-2 homology 3 (BH3) domains of activated pro-apoptotic members (e.g., BAX) can, however, be intercepted and sequestered by structurally-defined surface grooves within the anti-apoptotic members (see, e.g., Sattler, M. et al. Structure of Bcl-xL-Bak peptide complex: recognition between regulators of apoptosis. *Science* 275, 983-6 (1997)). The relative levels of death-activating (pro-apoptotic) BH3 domains and anti-apoptotic BH3-binding pockets dictate the cellular response to stress. Cancer cells hijack the survival circuitry of the BCL-2 family pathway, exploiting pathologic overexpression of anti-apoptotic proteins to stymie physiologic and pharmacologic pro-apoptotic stimuli. By overexpressing these anti-apoptotic proteins, cancer cells maintain a survival advantage in the face of pro-apoptotic stimuli. Thus, the over-expression of anti-apoptotic members is believed to contribute to cancer pathogenesis.

Whereas the mainstay of developmental BCL-2 family therapeutics has focused on the loss-of-function strategy of inhibiting anti-apoptotic proteins, direct activation of BAX by select pro-apoptotic BCL-2 members that only contain a conserved BH3 domain ("BH3-only" proteins) has also emerged as a physiologically relevant mechanism for inducing mitochondrial apoptosis during development and homeostasis (see Ren, D. et al. BID, BIM, and PUMA are essential for activation of the BAX- and BAK-dependent cell death program. *Science* 330, 1390-3 (2010)).

SUMMARY

I

This application features pyrazol-3-one compounds that activate a pro-apoptotic function of BAX, making them therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or lack of apoptosis of diseased or damaged cells). Examples of such diseases, disorders, and conditions include (but are not limited to) those associated with blockade(s) of cell death pathways (e.g., over-expression of anti-apoptotic BCL-2 proteins), e.g., hyperproliferative diseases, such as cancer (e.g., leukemia, e.g., acute lymphoblastic leukemia ("ALL") or acute myelogenous leukemia ("AML"); e.g., chronic lymphoblastic leukemia ("CLL") or chronic myelogenous leukemia ("CML")). While not wishing to be bound by theory, it is believed that the compounds described herein induce and increase apoptosis in target cells (e.g., pathogenic cells including, but not limited to, cancer cells), thereby suppressing tumor growth and/or proliferation. It is further believed that increasing apoptosis in such target cells reestablishes the normal apoptotic control that, during homeostasis, is associated with a regulated balance between pro- and anti-apoptotic protein functions.

II

[A] In some embodiments, the compounds described herein directly activate BAX by direct binding to BAX.

In some embodiments, the compounds described herein selectively bind to and activate BAX. For example, the compounds described herein selectively bind to and activate BAX in the presence of one (or more) different BCL-2 proteins, e.g., in the presence of one (or more) other pro-apoptotic BCL-2 proteins (e.g., BAK) and/or in the presence of one (or more) anti-apoptotic BCL-2 proteins.

In some embodiments, the compounds described herein directly activate BAX by direct binding to BAX; and selectively bind to and activate BAX, e.g. selectively bind to and activate BAX in the presence of one (or more) different BCL-2 proteins, e.g., in the presence of one (or more) other pro-apoptotic BCL-2 proteins (e.g., BAK) and/or in the presence of one (or more) anti-apoptotic BCL-2 proteins.

[B] It has been discovered that BAX contains a geographically distinct BH3 binding groove, which has been shown to mediate the direct activation of BAX. Specifically, structural analysis of a BIM BH3 death domain in complex with pro-apoptotic BAX uncovered a BH3 interaction site that, when engaged, results in the direct activation of BAX (see Gavathiotis, E. et al. BAX activation is initiated at a novel interaction site. *Nature* 455, 1076-81 (2008)). A BIM BH3 α-helix, structurally reinforced by hydrocarbon stapling, engages BAX at the opposite side of the protein from the canonical BH3-binding groove of anti-apoptotic proteins (see Gavathiotis, E. et al. BAX activation is initiated at a novel interaction site. *Nature* 455, 1076-81 (2008)). See FIG. 1A. This BH3 trigger site on BAX is formed by the confluence of α-helices 1 and 6, and is structurally defined by a hydrophobic groove comprised of amino acids M20, A24, L27, I31, I133, M137, and L141, and a perimeter of charged and hydrophilic residues, including K21, Q28, Q32, E131, and R134. See FIG. 1B. The flexible loop between α-helices 1 and 2 partially overlies the binding site and its displacement by BIM BH3 has been implicated as the first ligand-induced conformational change of the BAX activation mechanism (see Gavathiotis, E., Reyna, D. E., Davis, M. L., Bird, G. H. & Walensky, L. D. BH3-triggered structural reorganization drives the activation of proapoptotic BAX. *Mol Cell* 40, 481-92 (2010)). For ease of exposition, this activating binding groove that is discussed at the start of section [III] is sometimes referred to herein as the "BAX trigger site"

In some embodiments, the compounds described herein directly activate BAX by binding to BAX at the BAX trigger site.

In some embodiments, the compounds described herein selectively activate BAX by binding to BAX at the BAX trigger site; e.g., selectively activate BAX in the presence of one (or more) different BCL-2 proteins, e.g., in the presence of one (or more) other pro-apoptotic BCL-2 proteins (e.g., BAK) and/or in the presence of one (or more) anti-apoptotic BCL-2 proteins.

[C] In some embodiments, the compounds described herein induce or activate BAX-dependent or mediated apoptosis (cell death).

[D] In some embodiments, the methods described herein can include in vitro methods, e.g., contacting a sample containing BAX (e.g., a cell or tissue containing BAX) with a compound of formula (I) or a pharmaceutically acceptable salt thereof (e.g., including any subgenera or specific compound thereof of formula (I), e.g., formula (I-A))

In some embodiments, the methods described herein can include administering a compound of formula (I) or a pharmaceutically acceptable salt thereof (e.g., including any subgenera or specific compound thereof of formula (I), e.g., formula (I-A)) to a subject (e.g., a subject in need thereof, e.g., a mammal, such as a human).

[E] Accordingly, in one aspect, methods for activating (e.g., directly, selectively, directly and selectively as defined anywhere herein) BAX and/or inducing or activating BAX-dependent apoptosis are featured, which include contacting BAX with a compound of formula (I) or a pharmaceutically acceptable salt thereof:

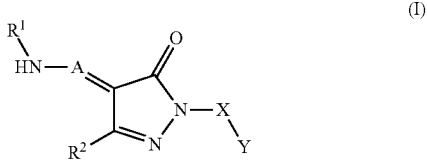

(I)

wherein:

A is N or CH;

X is heteroaryl, which contains 5 ring atoms, wherein from 1-2 of the ring atoms is/are independently selected from N, NH, N($C_1$-$C_3$ alkyl), O, and S; wherein:
X is connected to the pyrazolone nitrogen via a ring carbon atom in X; and
X is optionally further substituted with 1 $R^a$:
or
X is phenyl optionally substituted with from 1-5 $R^a$;
or
X is heteroaryl, which contains from 8-10 ring atoms, wherein from 1-4 of the ring atoms is/are independently selected from N, NH, N($C_1$-$C_3$ alkyl), O, and S; wherein:
X is connected to the pyrazolone nitrogen via a ring carbon atom in X; and
X is optionally further substituted with 1 $R^a$:

Y is:
(i) $C_6$-$C_{10}$ aryl, which is optionally substituted with from 1-5 independently selected $R^b$; or
(ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^b$; or
(iii) $C_1$-$C_6$ alkyl, $C_1$-$C_6$ haloalkyl, $C_1$-$C_6$ alkoxy, $C_1$-$C_6$ thioalkoxy, $C_1$-$C_6$ haloalkoxy, or $C_1$-$C_6$ halothioalkoxy, each of which is optionally substituted with —OH, —$NH_2$, or —SH;

$R^1$ is:
(i) $C_6$-$C_{10}$ aryl, which is optionally substituted with from 1-5 independently selected $R^c$; or
(ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^c$; or
(iii) —C(O)—($C_6$-$C_{10}$ aryl or heteroaryl, which contains from 5-10 ring atoms as defined in $R^1$ definition (i) and (ii), respectively, above); or
(iv) hydrogen;

each of $R^2$ and $R^a$ is, independently, selected from any one of the substituents delineated collectively in (a), (b), (c), (d), and (e) below:
(a) $C_1$-$C_8$ alkyl or $C_1$-$C_8$ haloalkyl, each of which is optionally substituted with from 1-2 $R^d$;
(b) phenyl that is optionally substituted with from 1-4 $R^e$;
(c) heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$;

(d) $C_3$-$C_8$ cycloalkyl or $C_3$-$C_8$ cycloalkenyl, each of which is optionally substituted with from 1-4 independently selected $C_1$-$C_4$ alkyl groups; or (e) —NHC(O)($C_1$-$C_6$ alkyl), —C(O)($C_1$-$C_6$ alkyl); or —C(O)O($C_1$-$C_6$ alkyl);

$R^b$, at each occurrence, is independently selected from any one the substituents delineated collectively in (aa), (bb) and (cc) below:

(aa) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH ($C_1$-$C_6$ alkyl), N($C_1$-$C_6$ alkyl)$_2$, or —NHC(O)($C_1$-$C_6$ alkyl), each of which is optionally substituted with —OH, —NH$_2$, azido (—N$_3$), or —SH;

(bb) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), or —NHSO$_2$($C_1$-$C_6$ alkyl); and (cc) $C_3$-$C_6$ cycloalkyl, $C_3$-$C_6$ cycloalkoxy, or heterocyclyl containing from 5-6 ring atoms, wherein from 1-2 of the ring atoms of the heterocyclyl is independently selected from N, NH, N($C_1$-$C_6$ alkyl), NC(O)($C_1$-$C_6$ alkyl), O, and S; and each of said ring systems is optionally substituted with from 1-3 independently selected $C_1$-$C_4$ alkyl groups;

each occurrence of $R^c$ and $R^e$ is, independently, selected from any one the substituents delineated collectively in (aaa), (bbb), (ccc), and (ddd) below:

(aaa) $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_1$-$C_6$ haloalkyl, —NH ($C_1$-$C_6$ alkyl), N($C_1$-$C_6$ alkyl)$_2$, or —NHC(O)($C_1$-$C_6$ alkyl), each of which is optionally substituted with —OH, —NH$_2$, or —SH; (and optionally benzyloxy);

(bbb) halo; —OH; —CN; nitro; —NH$_2$; azido; $C_2$-$C_4$ alkenyl; $C_2$-$C_4$ alkynyl; —C(O)H; —C(O)($C_1$-$C_6$ alkyl); C(O)OH; —C(O)O($C_1$-$C_6$ alkyl); —OC(O)($C_1$-$C_6$ alkyl); —SO$_2$($C_1$-$C_6$ alkyl); —SO$_2$($C_1$-$C_6$ haloalkyl); —C(O)NH$_2$; —C(O)NH($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); —SO$_2$N($C_1$-$C_6$ alkyl)$_2$; —NHCO($C_1$-$C_6$ alkyl), —NHSO$_2$($C_1$-$C_6$ alkyl); —C(O)O—(CH$_2$)$_{1-3(e.g., 1)}$—C(O)-(phenyl optionally substituted as defined in (ddd) below (e.g., —C(O)O—CH$_2$—C(O)-(phenyl);

(ccc) L-$C_3$-$C_8$ cycloalkyl, $C_3$-$C_6$ cycloalkoxy, or L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of said ring systems is optionally substituted with from 1-3 independently selected $C_1$-$C_4$ alkyl groups; and wherein L is a bond or $C_1$-$C_6$ alkylene; and (ddd) phenyl, —O-(phenyl), or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$; —NHC (O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH; and $R^d$ at each occurrence is, independently, selected from hydroxyl, $C_1$-$C_6$ alkoxy; $C_1$-$C_6$ thioalkoxy; $C_1$-$C_6$ haloalkoxy; $C_1$-$C_6$ thiohaloalkoxy; —NH$_2$; —NH($C_1$-$C_6$ alkyl); N($C_1$-$C_6$ alkyl)$_2$; —NHC(O)($C_1$-$C_6$ alkyl); cyano; —C(O)H; —C(O)($C_1$-$C_6$ alkyl); —C(O)($C_1$-$C_6$ haloalkyl); C(O)OH; —C(O)O($C_1$-$C_6$ alkyl); —C(O)NH$_2$; —C(O)NH ($C_1$-$C_6$ alkyl); C(O)N($C_1$-$C_6$ alkyl)$_2$; —SO$_2$($C_1$-$C_6$ alkyl); —SO$_2$NH$_2$; —SO$_2$NH($C_1$-$C_6$ alkyl); and —SO$_2$N($C_1$-$C_6$ alkyl)$_2$.

One or more of the following can apply.

In some embodiments, X is not phenyl optionally substituted with from 1-5 $R^a$.

In some embodiments, IV is not substituted directly or indirectly with one or more hydroxyl (—OH) groups.

In some embodiments, X is not phenyl optionally substituted with from 1-5 $R^a$; and $R^1$ is not substituted directly or indirectly with one or more hydroxyl (—OH) groups.

In some embodiments, when $R^1$ is 2-methoxyphenyl, and $R^2$ is $C_1$-$C_8$ alkyl (e.g., CH$_3$), then Y cannot be substituted phenyl, e.g., monosubstituted phenyl, e.g., phenyl monosubstituted at the para position, e.g., 4-chlorophenyl).

In some embodiments, when $R^1$ is 2-carboxyphenyl, and $R^2$ is $C_1$-$C_8$ alkyl (e.g., CH$_3$), then Y cannot be substituted phenyl, e.g., monosubstituted phenyl, e.g., phenyl monosubstituted at the para position, e.g., 4-methoxyphenyl).

In some embodiments, $R^1$ is other than 3-nitro-4-chlorophenyl. In certain embodiments, $R^1$ is other than 3-nitro-4-chlorophenyl when $R^2$ and Y are both unsubstituted phenyl.

In some embodiments, the compound is other than the compound sometimes referred to herein as "BAM7."

In another aspect, compounds having formula (I-A), or a pharmaceutically acceptable salt thereof, are featured:

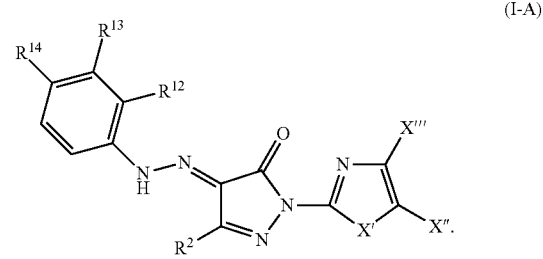

(I-A)

In some embodiments of formula (I-A):
X' is S;
X''' is unsubstituted phenyl,
X'' is H or $C_1$-$C_4$ alkyl;
$R^2$ is:
$C_1$-$C_4$ alkyl; or
phenyl that is optionally substituted with from 1-4 $R^e$; or heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$;
$R^{12}$ is:
—C(O)OH;
$C_2$-$C_6$ alkoxy that is optionally substituted with —NH$_2$; or heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S;

and each of which is optionally substituted with from 1-3 independently selected $C_1$-$C_4$ alkyl groups;

each of $R^{13}$ and $R^{14}$ is H; and each occurrence of $R^e$ is, independently, halo; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl.

One or more of the following can apply.

In certain embodiments, it is provided that $R^{12}$ cannot be —C(O)OH when $R^2$ is unsubstituted phenyl.

In certain embodiments, it is provided that $R^{12}$ cannot be —$OCH_2CH_3$ when $R^2$ is unsubstituted phenyl.

In certain embodiments, it is provided that $R^{12}$ cannot be —$OCH_2CH_3$ when $R^2$ is $CH_3$.

In other embodiments of formula (I-A):

X' is NH;

X''' is unsubstituted phenyl,

X'' is H or $C_1$-$C_4$ alkyl;

$R^2$ is:

$C_1$-$C_4$ alkyl; or phenyl that is optionally substituted with from 1-4 $R^e$; or heteroaryl containing from 5-6 ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$;

$R^{12}$ is:

—C(O)OH;

$C_2$-$C_6$ alkoxy that is optionally substituted with —$NH_2$; or heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups;

each of $R^{13}$ and $R^{14}$ is H; and each occurrence of $R^e$ is, independently, halo; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl.

[F] In one aspect, methods for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or the lack of apoptosis of diseased or damaged cells) in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

[G] In another aspect, methods for treating (e.g., controlling, relieving, ameliorating, alleviating, or slowing the progression of) or preventing (e.g., delaying the onset of or reducing the risk of developing) diseases, disorders, and conditions associated with blockade(s) of cell death pathways (e.g., over-expression of anti-apoptotic proteins BCL-2 proteins) in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

[H] In a further aspect, methods for treating (e.g., controlling, relieving, ameliorating, alleviating, or slowing the progression of) or preventing (e.g., delaying the onset of or reducing the risk of developing) a hyperproliferative disease in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

In an aspect, methods for treating (e.g., controlling, relieving, ameliorating, alleviating, or slowing the progression of) a hyperproliferative disease in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

[I] In still another aspect, methods for treating (e.g., controlling, relieving, ameliorating, alleviating, or slowing the progression of) or preventing (e.g., delaying the onset of or reducing the risk of developing) cancer (e.g., leukemia, e.g., ALL or AML; e.g., CLL or CML) in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

In an aspect, methods for treating (e.g., controlling, relieving, ameliorating, alleviating, or slowing the progression of) cancer (e.g., leukemia, e.g., ALL or AML) in a subject in need thereof are featured. The methods include administering to the subject (e.g., an effective amount of) a compound of formula (I), or a pharmaceutically acceptable salt thereof (e.g., including any subgenera or specific compound thereof of formula (I), e.g., formula (I-A)).

[J] In yet another aspect, methods of modulating (e.g., increasing) apoptosis in vitro or in vivo are featured. Also featured are methods of modulating (e.g., decreasing) cell division in vitro or in vivo are featured. The methods can include contacting a sample containing BAX (e.g., a cell or tissue containing BAX) with a compound of formula (I) or a pharmaceutically acceptable salt thereof (e.g., including any subgenera or specific compound thereof of formula (I)); or administering a compound of formula (I) or a pharmaceutically acceptable salt thereof (e.g., including any subgenera or specific compound thereof of formula (I), e.g., formula (I-A)) to a subject (e.g., a subject in need thereof, e.g., a mammal, such as a human).

[K] In some embodiments, the methods described above and throughout this disclosure can include one or more of the following features.

The cancer can include carcinomas (originating in the outer layer of cells of the skin and internal membranes, e.g., breasts, lungs, intestines, skin, prostate, etc.); sarcomas (arising from connective tissue such as bone, muscle, cartilage and blood vessels), and hematologic malignancies (e.g., lymphomas and leukemias, which arise in the blood or blood-forming organs such as the spleen, lymph nodes and bone marrow, e.g., leukemias, e.g., ALL or AML; e.g., CLL or CML). Cancer cells can include, for example, tumor cells, neoplastic cells, malignant cells, metastatic cells, and hyperplastic cells.

Non-limiting examples of cancers include breast cancer, prostate cancer, lymphoma, skin cancer, pancreatic cancer, colon cancer, melanoma, malignant melanoma, ovarian cancer, brain cancer, primary brain carcinoma, head-neck cancer, glioma, glioblastoma, liver cancer, bladder cancer, non-small cell lung cancer, head or neck carcinoma, breast carcinoma, ovarian carcinoma, lung carcinoma, small-cell lung carcinoma, Wilms' tumor, cervical carcinoma, testicular carcinoma, bladder carcinoma, pancreatic carcinoma, stomach carcinoma, colon carcinoma, prostatic carcinoma, genitourinary carcinoma, thyroid carcinoma, esophageal carcinoma, myeloma, multiple myeloma, adrenal carcinoma, renal cell carcinoma, endometrial carcinoma, adrenal cortex carcinoma, malignant pancreatic insulinoma, malignant carcinoid carcinoma, choriocarcinoma, mycosis fungoides, malignant hypercalcemia, cervical hyperplasia, leukemia, acute lymphocytic leukemia, chronic lymphocytic leukemia, chronic granulocytic leukemia, acute granulocytic leukemia, acute myelogenous leukemia, chronic myelogenous leukemia, hairy cell leukemia, neuroblastoma, rhabdomyosarcoma, Kaposi's sarcoma, polycythemia vera, essential thrombocytosis, Hodgkin's disease, non-Hodgkin's lymphoma, soft-tissue sarcoma, osteogenic sarcoma, primary macroglobulinemia, and retinoblastoma.

In some embodiments, the patient has not been treated with an agent that causes a thrombocytopenia-associated condition. In some embodiments the patient is not suffering from and/or is not a risk from developing a thrombocytopenia-associated condition.

In some embodiments, the methods further include administering one or more additional therapeutic agents (e.g., anticancer/chemotherapeutic agents) and/or techniques (e.g., radiation therapies, surgical interventions, and the like) to a subject or in vitro cells, tissues, and organs.

In certain embodiments, the methods further include administering one or more additional therapeutic agents such as: agents that induce apoptosis; polynucleotides (e.g., anti-sense, ribozymes, siRNA); polypeptides (e.g., enzymes and antibodies); biological mimetics (BH3 mimetics); agents that bind to and inhibit anti-apoptotic proteins (e.g., agents that inhibit anti-apoptotic BCL-2 proteins); alkaloids; alkylating agents; antitumor antibiotics; antimetabolites; hormones; platinum compounds; monoclonal or polyclonal antibodies (e.g., antibodies conjugated with anticancer drugs, toxins, defensins, etc.), toxins, radionuclides; biological response modifiers (e.g., interferons (e.g., IFN-.alpha., etc.) and interleukins (e.g., IL-2, etc.), etc.); adoptive immunotherapy agents; hematopoietic growth factors; agents that induce tumor cell differentiation (e.g., all-trans-retinoic acid, etc.); gene therapy reagents (e.g., antisense therapy reagents and nucleotides); tumor vaccines; angiogenesis inhibitors; proteosome inhibitors: NF kappa .beta. modulators; anti-CDK compounds; HDAC inhibitors; and the like.

In certain embodiments, the methods further include administering one or more additional therapeutic agents that bind to and inhibit anti-apoptotic proteins (e.g., agents that inhibit anti-apoptotic BCL-2 proteins), such as ABT-263, obatoclax, gossypol derivatives, IAP inhibitors, and stapled peptides that target anti-apoptotic proteins (MCL-1 SAHB (see, Stewart et al, Nature Chem Biol, 2010), BID SAHB (Walensky et al Science 2004), BAD SAHB (Danial et al Nature Medicine 2008), BIM SAHB (Gavathiotis et al Nature 2008), etc.).

In certain embodiments, the methods further include administering one or more additional therapeutic agents that induce or stimulate apoptosis. Agents that induce apoptosis include, but are not limited to, radiation (e.g., X-rays, gamma rays, UV); kinase inhibitors (e.g., Epidermal Growth Factor Receptor (EGFR) kinase inhibitor, Vascular Growth Factor Receptor (VGFR) kinase inhibitor, Fibroblast Growth Factor Receptor (FGFR) kinase inhibitor, Platelet-derived Growth Factor Receptor (PDGFR) kinase inhibitor, and Bcr-Abl kinase inhibitors such as GLEEVEC); antisense molecules; antibodies (e.g., HERCEPTIN, RITUXAN, ZEVALIN, and AVASTIN); anti-estrogens (e.g., raloxifene and tamoxifen); anti-androgens (e.g., flutamide, bicalutamide, finasteride, aminoglutethamide, ketoconazole, and corticosteroids); cyclooxygenase 2 (COX-2) inhibitors (e.g., celecoxib, meloxicam, NS-398, and non-steroidal anti-inflammatory drugs (NSAIDs)); anti-inflammatory drugs (e.g., butazolidin, DECADRON, DELTASONE, dexamethasone, dexamethasone intensol, DEXONE, HEXADROL, hydroxychloroquine, METICORTEN, ORADEXON, ORASONE, oxyphenbutazone, PEDIAPRED, phenylbutazone, PLAQUENIL, prednisolone, prednisone, PRELONE, and TANDEARIL); and cancer chemotherapeutic drugs (e.g., irinotecan (CAMPTOSAR), CPT-11, fludarabine (FLUDARA), dacarbazine (DTIC), dexamethasone, mitoxantrone, MYLOTARG, VP-16, cisplatin, carboplatin, oxaliplatin, 5-FU, doxorubicin, gemcitabine, bortezomib, gefitinib, bevacizumab, TAXOTERE or TAXOL); cellular signaling molecules; ceramides and cytokines; and staurosporine, and the like.

In some embodiments, the subject can be a subject in need thereof (e.g., a subject identified as being in need of such treatment, such as a subject having, or at risk of having, one or more of the diseases or conditions described herein). Identifying a subject in need of such treatment can be in the judgment of a subject or a health care professional and can be subjective (e.g. opinion) or objective (e.g. measurable by a test or diagnostic method). In some embodiments, the subject can be a mammal. In certain embodiments, the subject can be a human.

In certain embodiments, the subject has not previously undergone chemotherapy. In certain embodiments, the subject is not suffering from, or at risk of, thrombocytopenia, such as thrombocytopenia resulting from chemotherapy, radiation therapy, or bone marrow transplantation as treatment for cancer or lymphoma.

[L] In another aspect, methods of screening for (thereby identifying) compounds that activate BAX are featured. Said methods generally include screening a compound of formula (I) or a pharmaceutically acceptable salt thereof (e.g., including any subgenera or specific compound thereof of formula (I), e.g., formula (I-A)) and a test compound. The methods include providing: a compound of formula (I) or a pharmaceutically acceptable salt thereof (e.g., including any subgenera or specific compound thereof of formula (I)); a test compound; a first group of cells; and contacting the first group of cells with the formula (I) compound and the test compound; and observing the effects of contacting the first group of cells with the formula (I) compound and the test compound. In some of these embodiments, the methods further provide the additional step of comparing the effects observed in the first cells against a second group of the cells contacted with the formula (I) compound alone, or with the test compound alone. Effects that may be observed include, but are not limited to, those described in the Examples section.

[M] In one aspect, pharmaceutical compositions are featured, which include a compound of formula (I), or a pharmaceutically acceptable salt thereof (e.g., including any subgenera or specific compound thereof of formula (I), e.g., formula (I-A)) and a pharmaceutically acceptable carrier. In some embodiments, the compositions can include one or more additional therapeutic agents (e.g., anticancer/chemotherapeutic agents) as defined anywhere herein.

In another aspect, methods of making the pharmaceutical compositions described herein are featured. In some embodiments, the methods include taking any one or more of the compounds of formula (I) (e.g., including any subgenera or specific compound thereof of formula (I), e.g., formula (I-A)) or a salt (e.g., a pharmaceutically acceptable salt) thereof as defined anywhere herein, and mixing said compound(s) with one or more pharmaceutically acceptable carriers.

[N] In one aspect, methods of making the compounds described herein are featured. In some embodiments, the methods include taking any one of the intermediate compounds described herein and reacting it with one or more chemical reagents in one or more steps to produce a compound of formula (I) (and/or a compound of any of the other formulae described herein) or a salt (e.g., a pharmaceutically acceptable salt) thereof as defined anywhere herein.

[O] In one aspect, the compounds of formula (I) themselves (e.g., including any subgenera or specific compound thereof of formula (I)) or a salt (e.g., a pharmaceutically acceptable salt) thereof as defined anywhere herein are featured. In another aspect, any of the formula (I) compounds specifically described herein are featured.

In some embodiments, the compounds of formula (I) are other than those described in the following printed publications:

---

US 2011/0003851
U.S. Pat. No. 7,160,870
Stem Cells 2009, 27, 424

---

Amir, Mohd.; Javed, Sadique A.; Hassan, Mohd. Zaheen. Synthesis and antimicrobial activity of pyrazolinones and pyrazoles having benzothiazole moiety. Medicinal Chemistry Research No pp. yet given. CODEN: MCREEB ISSN: 1054-2523. AN 2011: 444952 CAPLUS Wang, Renxiao; Ma, Dawei; Li, Xun; Sun, Wei; Zhou, Bingcheng; Shi, Zhimin; Zhang, Xinglong; Zhu, Cuixia; Li, Wenwen. Preparation of thiazolylpyrazolone derivatives as Bcl-2 family proteins antagonists. Faming Zhuanli Shenqing (2009), 26 pp. CODEN: CNXXEV CN 101343268 A 20090114 CAN 150: 191511 AN 2009: 65234 CAPLUS Efros, L. S.; Davidenkov, L. S. Benzothiazole derivatives. Preparation of 1-benzothiazolyl-3-methyl-5(4H)-pyrazolone. Zhurnal Obshchei Khimii (1951), 21 2046-50. CODEN: ZOKHA4 ISSN: 0044-460X. CAN 46: 48608 AN 1952: 48608 CAPLUS Patel, Satyen P.; Joshi, Ashutosh M.; Hirapara, Ketan V.; Parekh, Hansa H. Synthesis and biological evaluation of some new pyrazolones and imidazolinones. Oriental Journal of Chemistry (2003), 19(2), 435-440. CODEN: OJCHEG ISSN: 0970-020X. CAN 140: 287320 AN 2003: 876733 CAPLUS Emandi, Anca; Maior, Ovidiu; Negoiu, Maria; Lazar, Laurentiu. 1-(2-Benzothiazolyl)-3-methyl-5-pyrazolone-based dyes. Revistade Chimie (Bucharest, Romania) (1994), 45(3), 179-82. CODEN: RCBUAU ISSN: 0034-7752. CAN 122: 83682 AN 1995: 17782 CAPLUS Mahesh, V. K.; Maheshwari, Mamta; Kumar, Virendra. Separation of some closely related 1-(2-benzothiazolyl)-3-methyl-4-arylhydrazono-pyrazoline-5-one derivatives by thin-layer chromatography. Fresenius' Zeitschrift fuer Analytische Chemie (1981), 309(5), 404. CODEN: ZACFAU ISSN: 0016-1152. CAN 96: 144438 AN 1982: 144438 CAPLUS Wang, Renxiao; Ma, Dawei; Li, Xun; Sun, Wei; Zhou, Bingcheng; Shi, Zhimin; Zhang, Xinglong; Zhu, Cuixia; Li, Wenwen. Preparation of thiazolylpyrazolone derivatives as Bcl-2 family proteins antagonists. Faming Zhuanli Shenqing (2009), 26 pp. CODEN: CNXXEV CN 101343268 A 20090114 CAN 150: 191511 AN 2009: 65234 CAPLUS Mamedov, V. A.; Mustakimova, L. V.; Gubaidullin, A. T.; Litvinov, I. A.; Levin, Ya. A. Reactions of Isomeric Arylchloropyruvates and Glycidates with Hydrazines. Russian Journal of Organic Chemistry (2005), 41(5), 694-702. CODEN: RJOCEQ ISSN: 1070-4280. CAN 144: 232964 AN 2005: 584176 CAPLUS Goldfarb, David Scott. Method using lifespan-altering compounds for altering the lifespan of eukaryotic organisms, and screening for such compounds. U.S. Pat. Appl. Publ. (2009), 57 pp. CODEN: USXXCO US 20090163545 A1 20090625 CAN 151: 115084 AN 2009: 875996 CAPLUS Westman, Jacob; Kull, Bjoern; Stenberg, Patric. Hydrazono-5-oxo-4,5-dihydropyrazole-1-carbothioic acid amide derivatives, and use thereof in the treatment of prostaglandin E synthase-related diseases. PCT Int. Appl. (2009), 30 pp. CODEN: PIXXD2 WO 2009130242 A1 20091029 CAN 151: 485350 AN 2009: 1330996 CAPLUS Wang, Renxiao; Ma, Dawei; Li, Xun; Sun, Wei; Zhou, Bingcheng; Shi, Zhimin; Zhang, Xinglong; Zhu, Cuixia; Li, Wenwen. Preparation of thiazolylpyrazolone derivatives as Bcl-2 family proteins antagonists. Faming Zhuanli Shenqing (2009), 26 pp. CODEN: CNXXEV CN 101343268 A 20090114 CAN 150: 191511 AN 2009: 65234 CAPLUS Baell, Jonathan B.; Holloway, Georgina A. New Substructure Filters for Removal of Pan Assay Interference Compounds (PAINS) from Screening Libraries and for Their Exclusion in Bioassays. Journal of Medicinal Chemistry (2010), 53(7), 2719-2740. CODEN: JMCMAR ISSN: 0022-2623. CAN 152: 326153 AN 2010: 159922 CAPLUS hi, Lin; Hudson, Andrew R.; Van Oeveren, Cornelis A.; Roach, Steven L.; Pickens, Jason C.; Shen, Yixing; Cuervo, Catalina; Valdez, Lino J.; Basinger, Jillian; Grant, Virgina H. Preparation of small molecule hematopoietic growth factor mimetic compounds that activate hematopoietic growth factor receptors. U.S. Pat. Appl. Publ. (2011), 40 pp. CODEN: USXXCO US 20110003851 A1 20110106 CAN 154: 109601 AN 2011: 20083 CAPLUS El-Haty, M. T. A coordination and stability study on some heterocyclic azopyrazolin-5-ones with yttrium(III), lanthanum(III), cerium(III) and uranyl(2+) ions. Journal of the Electrochemical Society of India (1991), 40(3), 113-18. CODEN: JESIA5 ISSN: 0013-466X. CAN 118: 176931 AN 1993: 176931 CAPLUS -continued US 2011/0003851
U.S. Pat. No. 7,160,870
Stem Cells 2009, 27, 424

El-Haty, M. T.; Adam, F. A.; Amrallah, A. H.; Abdalla, N. A. Structure of some new azopyrazolones derived from heterocyclic amines. Bulletin of the Faculty of Science, Assiut University (1989), 18(1), 23-33. CODEN: BSAUDW ISSN: 0366-4740. CAN 114: 23321 AN 1991: 23321 CAPLUS
Atta, Aly H. Reactions of 1-(2-benzothiazolyl)-4-(dicyanomethylene)-3-methyl-2-pyrazolin-5-one towards amines. Afinidad (1999), 56(483), 303-306. CODEN: AFINAE ISSN: 0001-9704. CAN 132: 78501 AN 1999: 719130 CAPLUS
Adam, F. A.; El-Haty, M. T. Synthesis and studies of thorium(IV) and cerium(III) complexes with some azopyrazolone compounds. Delta Journal of Science (1987), 11(3), 1089-103. CODEN: DJSCES ISSN: 1012-5965. CAN 111: 145745 AN 1989: 545745 CAPLUS
Atta, Aly H. Reactions of 1-(2-benzothiazolyl)-4-(dicyanomethylene)-3-methyl-2-pyrazolin-5-one towards amines. Heterocyclic Communications (1999), 5(3), 243-247. CODEN: HCOMEX ISSN: 0793-0283. CAN 131: 257477 AN 1999: 508741 CAPLUS
Gehring, Reinhold; Lindig, Markus; Wroblowsky, Heinz Juergen; Santel, Hans Joachim; Schmidt, Robert R.; Brandes, Wilhelm; Strang, Harry. Preparation of 4-(aminomethylene)-2-pyrazolin-5-ones as herbicides and fungicides. Ger. Offen. (1988), 155 pp. CODEN: GWXXBX DE 3728278 A1 19880623 CAN 110: 23881 AN 1989: 23881 CAPLUS
Goldfarb, David Scott. Method using lifespan-altering compounds for altering the lifespan of eukaryotic organisms, and screening for such compounds. U.S. Pat. Appl. Publ. (2009), 57 pp. CODEN: USXXCO US 20090163545 A1 20090625 CAN 151: 115085 AN 2009: 875997 CAPLUS
Parija, K.; Nayak, A.; Rout, Mahendra K. Preparation of azamerocyanines and evaluation of the effect of introduction of nitrogen atom in the chromophoric chain. Journal of the Indian Chemical Society (1970), 47(12), 1129-34. CODEN: JICSAH ISSN: 0019-4522. CAN 74: 113196 AN 1971: 113196 CAPLUS
Rout, M. K. Effect of structural changes on absorption. I. Merocyanine dyes and aza analogs of merocyanines, unsymmetrical cya nines, and p-dialkylaminostyryl dyes. Proceedings of the Institution of Chemists (India) (1963), 35(Pt. 3), 11730. CODEN: PCHIA2 ISSN: 0369-8599. CAN 59: 82634 AN 1963: 482634 CAPLUS
Zhi, Lin; Hudson, Andrew R.; Van Oeveren, Cornelis A.; Roach, Steven L.; Pickens, Jason C.; Shen, Yixing; Cuervo, Catalina; Valdez, Lino J.; Basinger, Jillian; Grant, Virgina H. Preparation of small molecule hematopoietic growth factor mimetic compounds that activate hematopoietic growth factor receptors. U.S. Pat. Appl. Publ. (2011), 40 pp. CODEN: USXXCO US 20110003851 A1 20110106 CAN 154: 109601 AN 2011: 20083 CAPLUS
Goldfarb, David Scott. Method using lifespan-altering compounds for altering the lifespan of eukaryotic organisms, and screening for such compounds. U.S. Pat. Appl. Publ. (2009), 57 pp. CODEN: USXXCO US 20090163545 A1 20090625 CAN 151: 115085 AN 2009: 875997 CAPLUS
Bondock, Samir; El-Azap, Hossam; Kandeel, Ez-Eldin M.; Metwally, Mohamed A. Eco-friendly solvent-free synthesis of thiazolylpyrazole derivatives. Monatshefte fuer Chemie (2008), 139(11), 1329-1335. CODEN: MOCMB7 ISSN: 0026-9247. CAN 151: 33471 AN 2008: 1321203 CAPLUS
Naylor, Edmund; Arredouani, Abdelilah; Vasudevan, Sridhar R.; Lewis, Alexander M.; Parkesh, Raman; Mizote, Akiko; Rosen, Daniel; Thomas, Justyn M.; Izumi, Minoru; Ganesan, A.; Galione, Antony; Churchill, Grant C. Identification of a chemical probe for NAADP by virtual screening. Nature Chemical Biology (2009), 5(4), 220-226. CODEN: NCBABT ISSN: 1552-4450. CAN 150: 369168 AN 2009: 216734 CAPLUS
Wang, Renxiao; Ma, Dawei; Li, Xun; Sun, Wei; Zhou, Bingcheng; Shi, Zhimin; Zhang, Xinglong; Zhu, Cuixia; Li, Wenwen. Preparation of thiazolylpyrazolone derivatives as Bcl-2 family proteins antagonists. Faming Zhuanli Shenqing (2009), 26 pp. CODEN: CNXXEV CN 101343268 A 20090114 CAN 150: 191511 AN 2009: 65234 CAPLUS
brahim, M. K. A.; Elghandour, A. H. H.; Abdel-Sayed, G. S. M.; Abdel Fattah, A. S. M. Synthesis of pyrazoles and fused pyrazoles. Novel synthesis of pyrano[2,3-c]pyrazole, thieno[2,3-c]pyrazole and pyrazolo[3,4-b]pyridine derivatives. Journal of the Indian Chemical Society (1997), 74(3), 206-208. CODEN: JICSAH ISSN: 0019-4522. CAN 127: 5036 AN 1997: 260589 CAPLUS
Zhi, Lin; Hudson, Andrew R.; Van Oeveren, Cornelis A.; Roach, Steven L.; Pickens, Jason C.; Shen, Yixing; Cuervo, Catalina; Valdez, Lino J.; Basinger, Jillian; Grant, Virgina H. Preparation of small molecule hematopoietic growth factor mimetic compounds that activate hematopoietic growth factor receptors. U.S. Pat. Appl. Publ. (2011), 40 pp. CODEN: USXXCO US 20110003851 A1 20110106 CAN 154: 109601 AN 2011: 20083 CAPLUS
Kalluraya, Balakrishna; Gunaga, Prashantha; Ramana, M. V. Synthesis of some triheterocyclic thiazole derivatives of biological interest. Indian Journal of Heterocyclic Chemistry (1999), 8(3), 241-242. CODEN: IJCHEI ISSN: 0971-1627. CAN 131: 87864 AN 1999: 285731 CAPLUS
Goldfarb, David Scott. Method using lifespan-altering compounds for altering the lifespan of eukaryotic organisms, and screening for such compounds. U.S. Pat. Appl. Publ. (2009), 57 pp. CODEN: USXXCO US 20090163545 A1 20090625 CAN 151: 115085 AN 2009: 875997 CAPLUS
Commercially available compounds.

In some embodiments, the foregoing exclusions can be combined with any one or more of the exclusions described in section [E] above.

[P] Embodiments can include any one or more of the following features.

X can contain 2 ring atoms independently selected from N, NH, N($C_1$-$C_3$ alkyl), O, and S; e.g., N and S or N and NH.

One of the two ring atoms can be independently selected from N, NH, and N($C_1$-$C_3$ alkyl) (e.g., N), and the other ring atom is independently selected from N, NH, N($C_1$-$C_3$ alkyl), O, and S (e.g., S or NH, e.g., S).

X can have formula X-1:

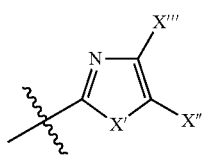

(X-1)

in which:
X' is NH, O, or S; and
one of X" and X"' is Y, and the other of X" and X"' is H or $R^a$.
X' can be S.
X' can be NH.
X"' can be Y.
X" can be H or $R^a$.
X" can be H.
X" can be $R^a$. In embodiments, $R^a$ can be $C_1$-$C_8$ alkyl (e.g., $CH_3$). In other embodiments, $R^a$ can be phenyl that is optionally substituted with from 1-4 $R^e$; or $C_3$-$C_8$ cycloalkyl which is optionally substituted with from 1-4 independently selected $C_1$-$C_4$ alkyl groups.

Y can be $C_6$-$C_{10}$ aryl (e.g., phenyl), which is optionally substituted with from 1-5 independently selected $R^b$. In embodiments, Y can be unsubstituted phenyl.

$R^1$ can be $C_6$-$C_{10}$ aryl, which is optionally substituted with from 1-5 independently selected $R^c$.

$R^1$ can be phenyl, which is substituted with from 1-5 (e.g., 1-3, 1-2, or 1) independently selected $R^c$.

Each occurrence of $R^c$ can be, independently, selected from any one of the substituents delineated collectively in (aaa), (bbb), (ccc), and (ddd) below:

(aaa) $C_1$-$C_6$ alkoxy, $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, —$NH_2$, or —SH;

(bbb) C(O)OH; —C(O)O($C_1$-$C_6$ alkyl); —OC(O)($C_1$-$C_6$ alkyl); —$SO_2NH_2$; —$SO_2$NH($C_1$-$C_6$ alkyl); or —$SO_2$N($C_1$-$C_6$ alkyl)$_2$; or —C(O)O—($CH_2$)$_{1-3(e.g., 1)}$—C(O)-(phenyl) optionally substituted as defined in (ddd) below (e.g., —C(O)O—$CH_2$—C(O)-(phenyl);

(ccc) $C_3$-$C_6$ cycloalkoxy or L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene; and (ddd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —$NH_2$, or —SH.

In embodiments, each occurrence of $R^c$ is, independently, selected from:
$C_1$-$C_6$ alkoxy;
$C_1$-$C_6$ alkoxy (e.g., $C_2$-$C_6$ alkoxy, e.g., ethoxy); or $C_1$-$C_6$ alkoxy (e.g., $C_2$-$C_6$ alkoxy, e.g., ethoxy) that is substituted with —$NH_2$;
$C_1$-$C_6$ alkyl;
—NHC(O)($C_1$-$C_6$ alkyl)
—C(O)OH;
L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., a bond); e.g., $R^c$ is optionally substituted morpholino or optionally substituted piperazinyl; and
phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —$NH_2$, or —SH.

In embodiments, $R^c$ can be $C_1$-$C_6$ alkoxy (e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy) that is substituted with —$NH_2$.

$R^1$ can have formula A:

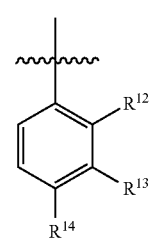

(A)

The following definitions apply to any formula described herein that contains formula (A).

One or two of $R^{12}$, $R^{13}$, and $R^{14}$ is(are) an independently selected $R^c$, and the other(s) is(are) hydrogen.
$R^{12}$ can be $R^c$ (as defined anywhere herein).
$R^{13}$ can be H.
$R^{14}$ can be H.
$R^{14}$ can be $R^c$.

$R^{12}$ can be $R^c$ (as defined anywhere herein), and each of $R^{13}$ and $R^{14}$ can be H.

$R^{14}$ can be $R^c$ (as defined anywhere herein), and each of $R^{12}$ and $R^{13}$ can be H.

In embodiments, $R^c$ can be $C_1$-$C_6$ alkoxy (e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy) that is substituted with —$NH_2$.

$R^c$ can be —C(O)OH.

$R^c$ can be L-heterocyclyl containing from 5-7 (e.g., 6) ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., a bond); e.g., $R^c$ is morpholino or piperazinyl. In embodiments, L can be a bond or $CH_2$ (e.g., L can be a bond).

$R^{13}$ can be H, and each of $R^{12}$ and $R^{14}$ can be $R^c$ (each independently as defined anywhere herein).

One of $R^{12}$ and $R^{14}$ can be $C_1$-$C_6$ alkoxy (e.g., ethoxy), and the other of $R^{12}$ and $R^{14}$ can be independently selected from:
- $C_1$-$C_6$ alkoxy;
- $C_1$-$C_6$ alkyl;
- —C(O)OH;
- —NHC(O)($C_1$-$C_6$ alkyl);
- L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., a bond); e.g., $R^c$ is optionally substituted morpholino or optionally substituted piperazinyl; and
- phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —$NH_2$, or —SH.

$R^1$ can be heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^c$.

$R^1$ can be heteroaryl, which contains from 5-6 ring atoms, wherein from 1-4 (e.g., 1-2) of the ring atoms is independently selected from N, NH, N($C_1$-$C_3$ alkyl), O, and S; and wherein said heteroaryl ring is optionally substituted with from 1-3 (e.g., 1-2 or 1) independently selected $R^c$. For example, $R^1$ can be thiazolyl.

$R^1$ can be heteroaryl, which contains from 8-10 ring atoms, wherein from 1-4 (e.g., 1-2) of the ring atoms is independently selected from N, NH, N($C_1$-$C_3$ alkyl), O, and S; and wherein said heteroaryl ring is optionally substituted with from 1-3 (e.g., 1-2 or 1) independently selected $R^c$. For example, $R^1$ can be indazolyl.

$R^2$ can be $C_1$-$C_8$ alkyl. For example, $R^2$ can be $CH_3$.

$R^2$ can be phenyl that is optionally substituted with from 1-4 $R^e$. In embodiments, $R^2$ can be unsubstituted phenyl.

$R^2$ can be $C_3$-$C_8$ cycloalkyl which is optionally substituted with from 1-4 independently selected $C_1$-$C_4$ alkyl groups.

$R^2$ is heteroaryl containing from 5-6 (e.g., 5) ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$. For example, $R^2$ can be furanyl, thienyl, or thiazolyl.

A can be N.

In some embodiments:

A is N;

X contains 2 ring atoms independently selected from N, NH, N($C_1$-$C_3$ alkyl), O, and S, and one of the ring atoms is independently selected from N, NH, and N($C_1$-$C_3$ alkyl), and the other ring atom is independently selected from N, NH, N($C_1$-$C_3$ alkyl), O, and S; and $R^1$ is $C_6$-$C_{10}$ aryl, which is optionally substituted with from 1-5 independently selected $R^c$ (e.g., $R^1$ can be phenyl, which is substituted with from 1-5 (e.g., 1-3, 1-2, or 1) independently selected $R^c$).

In certain embodiments, the compound can have formula I-A:

(I-A)

wherein:

X' is NH, O, or S;

one of X" and X'" is Y, and the other of X" and X'" is H or $R^a$;

one or two of $R^{12}$, $R^{13}$, and $R^{14}$ is(are) an independently selected $R^c$, and the other(s) is(are) hydrogen; and $R^2$ can be as defined anywhere herein.

X' can be S or NH (e.g., S), X'" is Y, and X" is H or $R^a$ (e.g., X" can be H or $C_1$-$C_3$ alkyl, e.g., $CH_3$).

Y can be $C_6$-$C_{10}$ aryl, which is optionally substituted with from 1-5 independently selected $R^b$ (e.g., Y can be unsubstituted phenyl).

$R^{12}$ can be $R^c$, and each of $R^{13}$ and $R^{14}$ is H; or $R^{14}$ is $R^c$, and each of $R^{12}$ and $R^{13}$ is H.

Each occurrence of $R^c$ is, independently, selected from:
- $C_1$-$C_6$ alkoxy;
- $C_1$-$C_6$ alkoxy (e.g., $C_2$-$C_6$ alkoxy, e.g., ethoxy); or $C_1$-$C_6$ alkoxy (e.g., $C_2$-$C_6$ alkoxy, e.g., ethoxy) that is substituted with —$NH_2$;
- $C_1$-$C_6$ alkyl;
- —C(O)OH;
- —NHC(O)($C_1$-$C_6$ alkyl);
- L-heterocyclyl containing from 5-7 (e.g., 6) ring atoms, wherein from 1-2 of the ring atoms of the heterocyclyl is independently selected from N, NH, N($C_1$-$C_6$ alkyl), NC(O)(C$_1$-C$_6$ alkyl), NC(O)O(C$_1$-C$_6$ alkyl), O, and S; and each of which is optionally substituted with from 1-3 independently selected C$_1$-C$_4$ alkyl groups; and wherein L is a bond or C$_1$-C$_6$ alkylene (e.g., a bond); e.g., R$^c$ is an optionally substituted morpholino or optionally substituted piperazinyl ring; and phenyl or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; —C(O)(C$_1$-C$_6$ alkyl); C(O)OH; —C(O)O(C$_1$-C$_6$ alkyl); nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl, wherein said alkyl or alkyl portion is optionally substituted with —OH, —NH$_2$, or —SH.

R$^c$ can be C$_1$-C$_6$ alkoxy (e.g., ethoxy or iso-propoxy); or R$^c$ can be —COOH; or R$^c$ can be morpholino or piperazinyl.

R$^c$ can be C$_1$-C$_6$ alkoxy (e.g., C$_2$-C$_6$ alkoxy, e.g., ethoxy or iso-propoxy) that is optionally substituted with —NH$_2$; or R$^c$ can be —COOH; or R$^c$ can be an optionally substituted morpholino or optionally substituted piperazinyl ring.

R$^c$ can be C$_1$-C$_6$ alkoxy (e.g., C$_2$-C$_6$ alkoxy, e.g., ethoxy or iso-propoxy) that is optionally substituted with —NH$_2$.

R$^2$ can be C$_1$-C$_8$ alkyl (e.g., CH$_3$).

R$^2$ can be phenyl or heteroaryl containing from 5-6 (e.g., 5) ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$ (e.g., R$^2$ is heteroaryl as defined above, e.g., thienyl, furanyl, or thiazolyl).

X" can be H or CH$_3$.

R$^2$ can be C$_1$-C$_4$ alkyl, such as CH$_3$. R$^2$ can be unsubstituted phenyl. R$^2$ can be heteroaryl containing from 5-6 ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$, such as thienyl, furanyl, or thiazolyl.

R$^{12}$ can be —C(O)OH. R$^{12}$ can be C$_2$-C$_6$ alkoxy that is optionally substituted with NH$_2$, such as —OCH$_2$CH$_3$ or —OCH$_2$CH$_2$NH$_2$. R$^{12}$ can be heterocyclyl containing from 5-7 ring atoms, wherein from 1-2 of the ring atoms of the heterocyclyl is independently selected from N, NH, N(C$_1$-C$_6$ alkyl), NC(O)(C$_1$-C$_6$ alkyl), NC(O)O(C$_1$-C$_6$ alkyl), O, and S; and each of which is optionally substituted with from 1-3 independently selected C$_1$-C$_4$ alkyl groups, such as an optionally substituted piperazinyl ring.

X" can be H or CH$_3$; and R$^2$ can be C$_1$-C$_4$ alkyl, such as CH$_3$; or R$^2$ can be unsubstituted phenyl; or R$^2$ can be heteroaryl containing from 5-6 ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$, such as thienyl, furanyl, or thiazolyl.

X" can be H or CH$_3$; and
R$^2$ can be C$_1$-C$_4$ alkyl, such as CH$_3$; or R$^2$ can be unsubstituted phenyl; or R$^2$ can be heteroaryl containing from 5-6 ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$, such as thienyl, furanyl, or thiazolyl; and
R$^{12}$ can be —C(O)OH; or R$^{12}$ can be C$_2$-C$_6$ alkoxy that is optionally substituted with —NH$_2$, such as —OCH$_2$CH$_3$ or —OCH$_2$CH$_2$NH$_2$; or R$^{12}$ can be heterocyclyl containing from 5-7 ring atoms, wherein from 1-2 of the ring atoms of the heterocyclyl is independently selected from N, NH, N(C$_1$-C$_6$ alkyl), NC(O)(C$_1$-C$_6$ alkyl), NC(O)O(C$_1$-C$_6$ alkyl), O, and S; and each of which is optionally substituted with from 1-3 independently selected C$_1$-C$_4$ alkyl groups, such as an optionally substituted piperazinyl ring.

X" can be H or CH$_3$; and
R$^2$ can be C$_1$-C$_4$ alkyl, such as CH$_3$; and
R$^{12}$ can be C$_2$-C$_6$ alkoxy that is optionally substituted with —NH$_2$, such as —OCH$_2$CH$_3$ or —OCH$_2$CH$_2$NH$_2$;
In some embodiments:
A is N;
X contains 2 ring atoms independently selected from N, NH, N(C$_1$-C$_3$ alkyl), O, and S, and one of the ring atoms is independently selected from N, NH, and N(C$_1$-C$_3$ alkyl), and the other ring atom is independently selected from N, NH, N(C$_1$-C$_3$ alkyl), O, and S; and
R$^1$ is heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-3 independently selected W.

In certain embodiments, the compound can have formula I-B:

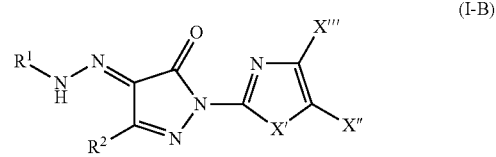

(I-B)

wherein:
X' is NH, O, or S; and
one of X" and X'" is Y, and the other of X" and X'" is H or R$^a$;
X' can be S, X'" can be Y, and X" can be H or R$^a$.
X" can be H.
R$^1$ can be thiazolyl.
Y can be C$_6$-C$_{10}$ aryl, which is optionally substituted with from 1-5 independently selected R$^b$ (e.g., unsubstituted phenyl).
R$^2$ can be phenyl that is optionally substituted with from 1-4 R$^e$; or heteroaryl containing from 5-6 (e.g., 5) ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$.
R$^2$ can be unsubstituted phenyl.

The compound can be selected from compounds delineated in FIGS. 11, 12, and 14.
The contacting can be in vitro.
The contacting is in vivo.
In some embodiments, any compound, composition, or method described herein can also include or further include any one or more of the other features delineated in the detailed description and/or in the claims.

[Q] Definitions
The term "mammal" includes organisms, which include mice, rats, cows, sheep, pigs, rabbits, goats, horses, monkeys, dogs, cats, and humans.

In embodiments, an amount of a compound of formula (I) or salt thereof can be an effective amount. "An effective amount" refers to an amount of a compound that confers a therapeutic effect (e.g., treats, e.g., controls, relieves, ameliorates, alleviates, or slows the progression of or prevents, e.g., delays the onset of or reduces the risk of developing, a disease, disorder, or condition or symptoms thereof) on the treated subject. The therapeutic effect may be objective (i.e., measurable by some test or marker) or subjective (i.e., subject gives an indication of or feels an effect). An effective amount of the compound described above may range from about 0.01 mg/kg to about 1000 mg/kg, (e.g., from about 0.1 mg/kg to about 100 mg/kg, from about 1 mg/kg to about 100 mg/kg). Effective doses will also vary depending on route of administration, as well as the possibility of co-usage with other agents.

The term "halo" or "halogen" refers to any radical of fluorine, chlorine, bromine or iodine.

In general, and unless otherwise indicated, substituent (radical) prefix names are derived from the parent hydride by either (i) replacing the "ane" in the parent hydride with the suffixes "yl," "diyl," "triyl," "tetrayl," etc.; or (ii) replacing the "e" in the parent hydride with the suffixes "yl," "diyl," "triyl," "tetrayl," etc. (Here the atom(s) with the free valence, when specified, is (are) given numbers as low as is consistent with any established numbering of the parent hydride). Accepted contracted names, e.g., adamantyl, naphthyl, anthryl, phenanthryl, furyl, pyridyl, isoquinolyl, quinolyl, and piperidyl, and trivial names, e.g., vinyl, allyl, phenyl, and thienyl are also used herein throughout. Conventional numbering/lettering systems are also adhered to for substituent numbering and the nomenclature of fused, bicyclic, tricyclic, and polycyclic rings.

The following definitions are used unless otherwise described. Specific and general values listed below for radicals, substituents, and ranges are for illustration only. They do not exclude other defined values or other values within defined ranges for the radicals and substituents. Unless otherwise indicated, alkyl, alkylene, alkoxy, alkenyl, and the like denote both straight and branched groups.

The term "alkyl" refers to a saturated hydrocarbon chain that may be a straight chain or branched chain, containing the indicated number of carbon atoms. For example, $C_1$-$C_6$ alkyl indicates that the group may have from 1 to 6 (inclusive) carbon atoms in it. Any atom can be optionally substituted, e.g., by one or more substitutents. Examples of alkyl groups include, without limitation, methyl, ethyl, n-propyl, isopropyl, and tert-butyl.

As used herein, the term "$C_{n-m}$ alkylene," employed alone or in combination with other terms, refers to a non-branched divalent alkyl linking group having n to m carbon atoms.

The term "haloalkyl" refers to an alkyl group in which at least one hydrogen atom is replaced by halo. In some embodiments, more than one hydrogen atom (e.g., 2, 3, 4, 5, 6, 7, 8, 9, 10, 11, 12, 13, or 14) is replaced by halo. In these embodiments, the hydrogen atoms can each be replaced by the same halogen (e.g., fluoro) or the hydrogen atoms can be replaced by a combination of different halogens (e.g., fluoro and chloro). "Haloalkyl" also includes alkyl moieties in which all hydrogens have been replaced by halo (sometimes referred to herein as perhaloalkyl, e.g., perfluoroalkyl, such as trifluoromethyl). Any atom can be optionally substituted, e.g., by one or more substituents.

As referred to herein, the term "alkoxy" refers to a group of formula —O(alkyl). Alkoxy can be, for example, methoxy (—OCH$_3$), ethoxy, propoxy, isopropoxy, butoxy, iso-butoxy, sec-butoxy, tert-butoxy, pentoxy, 2-pentoxy, 3-pentoxy, or hexyloxy. Likewise, the term "thioalkoxy" refers to a group of formula —S(alkyl). The terms "haloalkoxy" and "thio-haloalkoxy" refer to —O(haloalkyl) and —S(haloalkyl), respectively. Finally, the terms "cycloalkoxy" and "heterocyclyloxy" refer to a group of the formula —O(cycloalkyl) and —O(heterocyclyl), respectively.

The term "alkenyl" refers to a straight or branched hydrocarbon chain containing the indicated number of carbon atoms and having one or more carbon-carbon double bonds. Any atom can be optionally substituted, e.g., by one or more substituents. Alkenyl groups can include, e.g., vinyl, allyl, 1-butenyl, and 2-hexenyl. One of the double bond carbons can optionally be the point of attachment of the alkenyl substituent.

The term "alkynyl" refers to a straight or branched hydrocarbon chain containing the indicated number of carbon atoms and having one or more carbon-carbon triple bonds. Alkynyl groups can be optionally substituted, e.g., by one or more substituents. Alkynyl groups can include groups such as ethynyl, propargyl, and 3-hexynyl. One of the triple bond carbons can optionally be the point of attachment of the alkynyl substituent.

The term "heterocyclyl" refers to a fully saturated monocyclic, bicyclic, tricyclic or other polycyclic ring system having one or more constituent heteroatom ring atoms independently selected from O, N (it is understood that one or two additional groups may be present to complete the nitrogen valence and/or form a salt), or S. The heteroatom or ring carbon can be the point of attachment of the heterocyclyl substituent to another moiety. Any atom can be optionally substituted, e.g., by one or more substituents. Heterocyclyl groups can include groups such as tetrahydrofuryl, tetrahydropyranyl, piperidyl (piperidino), piperazinyl, morpholinyl (morpholino), pyrrolinyl, and pyrrolidinyl. By way of example, a phrase such as "heterocyclic ring containing from 5-6 ring atoms", wherein from 1-2 of the ring atoms is independently selected from N, NH, N($C_1$-$C_6$ alkyl), NC(O) ($C_1$-$C_6$ alkyl), O, and S; and wherein said heterocyclic ring is optionally substituted with from 1-3 independently selected $R^a$ would include (but not be limited to) tetrahydrofuryl, tetrahydropyranyl, piperidyl (piperidino), piperazinyl, morpholinyl (morpholino), pyrrolinyl, and pyrrolidinyl.

The term "cycloalkyl" refers to a fully saturated monocyclic, bicyclic, tricyclic, or other polycyclic hydrocarbon group. Any atom can be optionally substituted, e.g., by one or more substituents. A ring carbon serves as the point of attachment of a cycloalkyl group to another moiety. Cycloalkyl moieties can include groups such as cyclopropyl, cyclobutyl, cyclopentyl, cyclohexyl, cycloheptyl, adamantyl, and norbornyl (bicyclo[2.2.1]heptyl).

The term "cycloalkenyl" refers to partially unsaturated monocyclic, bicyclic, tricyclic, or other polycyclic hydrocarbon groups. A ring carbon (e.g., saturated or unsaturated) is the point of attachment of the cycloalkenyl substituent. Any atom can be optionally substituted e.g., by one or more substituents. Cycloalkenyl moieties can include, e.g., cyclohexenyl, cyclohexadienyl, or norbornenyl.

The term "aryl" refers to an aromatic monocyclic, bicyclic (2 fused rings), tricyclic (3 fused rings), or polycyclic (>3 fused rings) hydrocarbon ring system. One or more ring atoms can be optionally substituted by one or more substituents for example. Aryl moieties include groups such as phenyl and naphthyl.

The term "heteroaryl" refers to an aromatic monocyclic, bicyclic (2 fused rings), tricyclic (3 fused rings), or polycyclic (>3 fused rings) hydrocarbon groups having one or more heteroatom ring atoms independently selected from O, N (it is understood that one or two additional groups may be present to complete the nitrogen valence and/or form a salt), or S. One or more ring atoms can be optionally substituted, e.g., by one or more substituents. Examples of heteroaryl groups include, but are not limited to, 2H-pyrrolyl, 3H-indolyl, 4H-quinolizinyl, acridinyl, benzo[b]thienyl, benzothiazolyl, β-carbolinyl, carbazolyl, coumarinyl, chromenyl, cinnolinyl, dibenzo[b,d]furanyl, furazanyl, furyl, imidazolyl, imidizolyl, indazolyl, indolyl, isobenzofuranyl, isoindolyl, isoquinolyl, isothiazolyl, isoxazolyl, naphthyridinyl, oxazolyl, perimidinyl, phenanthridinyl, phenanthrolinyl, phenarsazinyl, phenazinyl, phenothiazinyl, phenoxathiinyl, phenoxazinyl, phthalazinyl, pteridinyl, purinyl, pyranyl, pyrazinyl, pyrazolyl, pyridazinyl, pyridyl, pyrimidinyl, pyrrolyl, quinazolinyl, quinolyl, quinoxalinyl, thiadiazolyl, thianthrenyl, thiazolyl, thienyl, triazolyl, and xanthenyl.

As used herein, the descriptor "—CN" represents the cyano group (and vice versa), wherein the carbon and nitrogen atoms are bound together by a triple bond. As used herein, the descriptor "—OH" represents the hydroxy group (and vice versa). The descriptors "C=O" or "C(O)" refers to a carbon atom that is doubly bonded to an oxygen atom.

In general, when a definition for a particular variable includes hydrogen and non-hydrogen (halo, alkyl, aryl, etc.) possibilities, the term "substituent(s) other than hydrogen" refers collectively to the non-hydrogen possibilities for that particular variable.

The term "substituent" refers to a group "substituted" on groups such as an alkyl, haloalkyl, cycloakyl, heterocyclyl, aryl, or heteroaryl group at any atom of that group. In one aspect, the substituent(s) on a group are independently any one single or any combination of two or more of the permissible atoms or groups of atoms delineated for that substituent. In another aspect, a substituent may itself be substituted with any one of the above substituents.

Further, as used herein, the phrase "optionally substituted" means unsubstituted (e.g., substituted with hydrogen (H)) or substituted. As used herein, the term "substituted" means that a hydrogen atom is removed and replaced by a substituent. It is understood that substitution at a given atom is limited by valency.

Descriptors such as "$C_6$-$C_{10}$ aryl that is optionally substituted with from 1-4 independently selected $R^b$ (and the like) is intended to include both an unsubstituted $C_6$-$C_{10}$ aryl group and a $C_6$-$C_{10}$ aryl group that is substituted with from 1-4 independently selected $R^b$. The use of a substituent (radical) prefix name such as alkyl without the modifier "optionally substituted" or "substituted" is understood to mean that the particular substituent is unsubstituted. However, the use of "haloalkyl" without the modifier "optionally substituted" or "substituted" is still understood to mean an alkyl group, in which at least one hydrogen atom is replaced by halo.

[R] Unless otherwise defined, all technical and scientific terms used herein have the same meaning as commonly understood by one of ordinary skill in the art to which this invention belongs. Methods and materials are described herein for use in the present invention; other, suitable methods and materials known in the art can also be used. The materials, methods, and examples are illustrative only and not intended to be limiting. All publications, patent applications, patents, sequences, database entries, and other references mentioned herein are incorporated by reference in their entirety. In case of conflict, the present specification, including definitions, will control.

Other features and advantages of the invention will be apparent from the following detailed description and figures, and from the claims.

DESCRIPTION OF DRAWINGS

FIG. 6A shows (i) a graph in which the measured chemical shift changes of $^{15}$N-BAX upon BAM7 titration up to a ratio of 1:1 BAX:BAM7 are plotted as a function of BAX residue number and (ii) a ribbon diagram. Residues with significant backbone amide chemical shift change are concentrated in the region of the trigger site (α1, α6; magenta). The Cα atoms of affected residues are represented as spheres in the ribbon diagram and lighter shaded bars in the graph (calculated significance threshold >0.009 p.p.m.).

FIG. 7 includes a ribbon diagram and a graph. BAM7 induces allosteric changes in key functional domains implicated in functional BAX activation. Upon increasing the ratio of BAM7:$^{15}$N-BAX from 1:1 to 2:1, a series of chemical shift changes become more prominent in the α1-α2 loop, α2 (BH3), and α9, three regions previously implicated in BIM BH3-triggered N-terminal loop opening, BAX BH3 exposure, and C-terminal helix mobilization, respectively[11]. These BAM7-induced allosteric changes reflect a major conformational change that has been linked to functional BAX activation. Cα atoms of affected residues are represented as spheres in the ribbon diagram and lighter shaded bars in the plot (calculated significance threshold >0.011 p.p.m.). The α1-α2 loop, α2 (BH3), and α9 are highlighted in pink, cyan, and yellow, respectively.

BAM7 treatment triggers dose-responsive BAX-mediated liposomal release. The exposure of liposomes to BAM7 or BAX alone had no such effect.

Figure 8A:
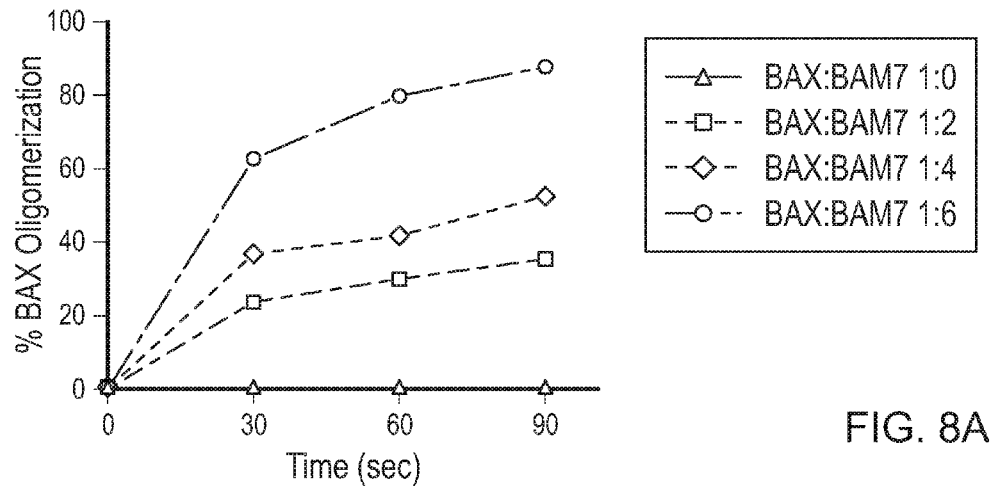
FIG. 8A is a graph showing that Co-incubation of BAM7 (10, 20, and 30 μM) and monomeric BAX (5 μM) induces dose- and time-responsive BAX oligomerization, as monitored by size exclusion chromatography.
Figure 8B:
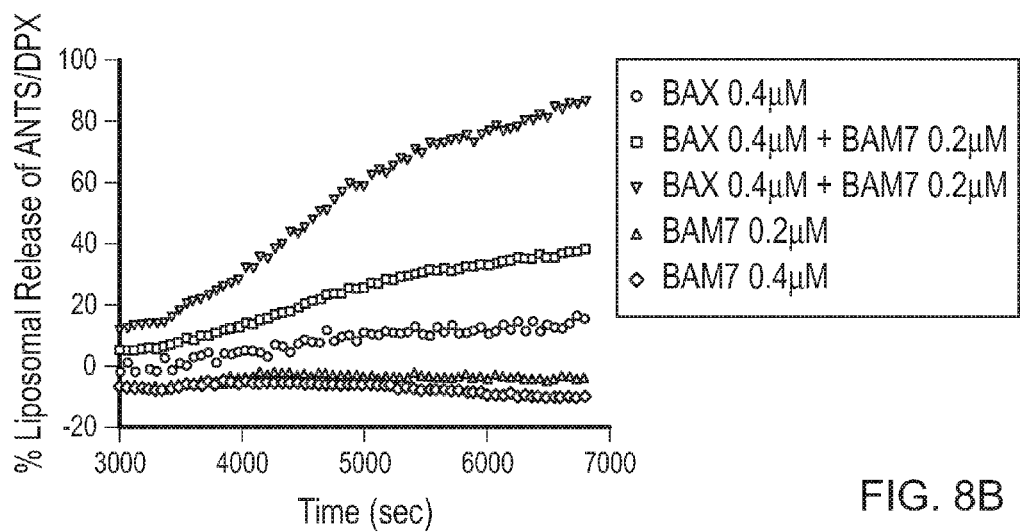
FIG. 8B is a graph showing that in the presence of ANTS/DPX-loaded liposomes.
Figure 8C:
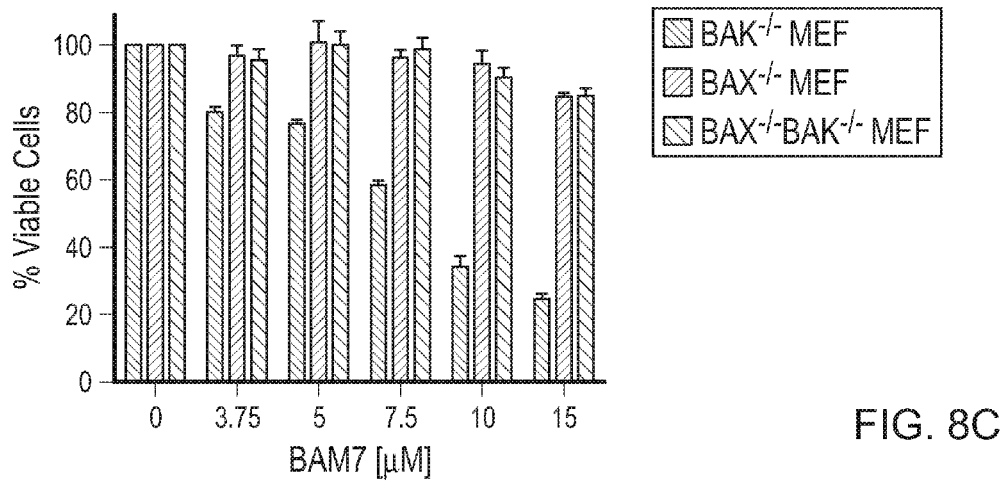

FIG. 8C is a bar graph that shows BAM7 selectively impaired the viability of Bak$^{-/-}$ MEFs, but had no effect on MEFs that lack BAX (Bax$^{-/-}$) or both BAX and BAK (Bax$^{-/-}$Bak$^{-/-}$).

Figure 8D:
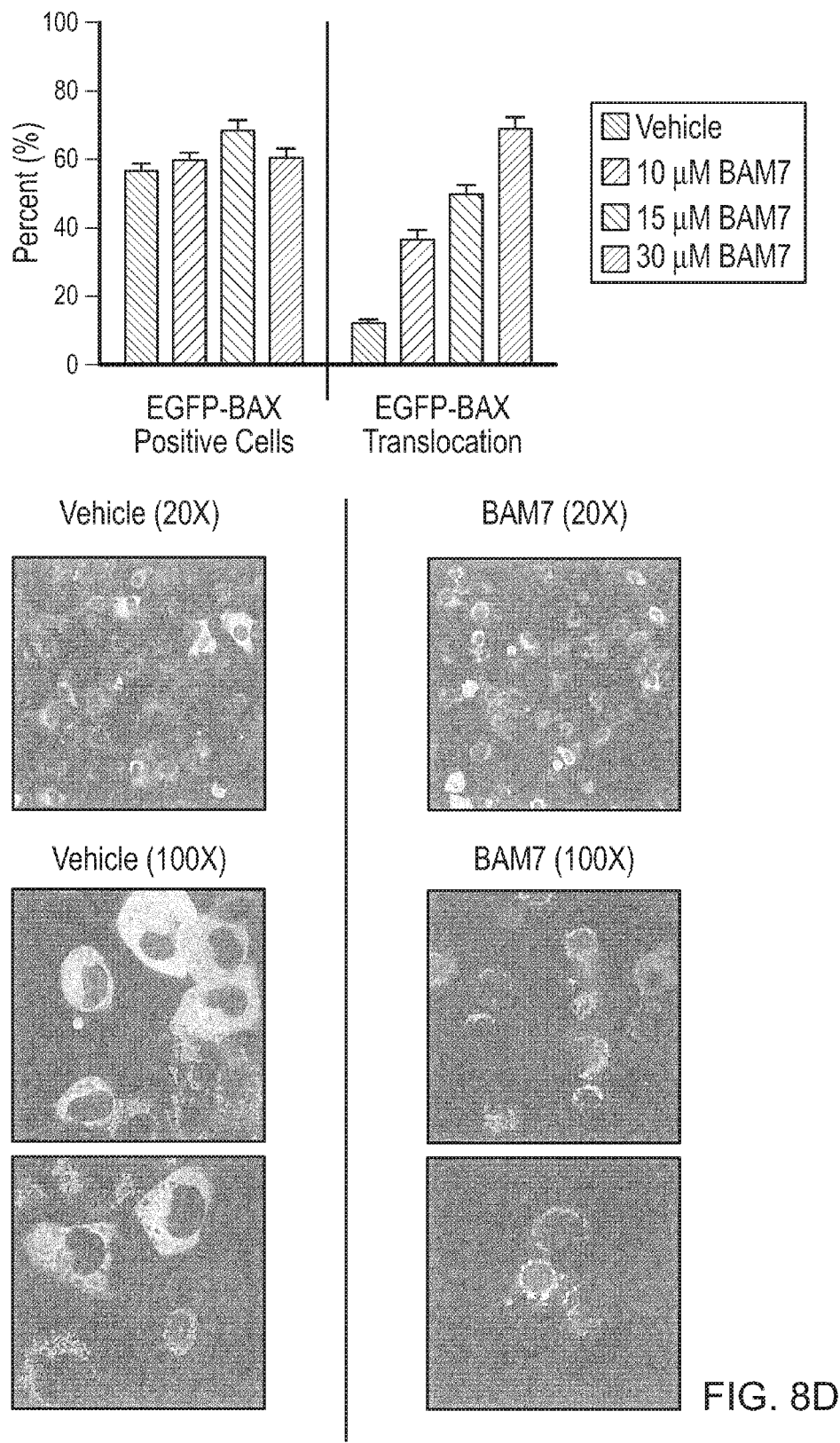

FIG. 8D shows that Bax$^{-/-}$Bak$^{-/-}$ MEFs reconstituted with EGFP-BAX (~60% EGFP-positive cells) display dose-responsive BAX translocation upon exposure to BAM7, as evidenced by the conversion of EGFP-BAX localization from a diffuse pattern to a mitochondrion-localized distribution. EGFP-BAX, green; Mitotracker, red; Colocalization, yellow; BAM7, 30 μM; Vehicle, 0.3% DMSO. Data are mean and s.d. for experiments performed in quadruplicate.

FIG. 8E shows Bak$^{-/-}$ MEFs that contain endogenous BAX exhibiting the morphologic features of apoptosis in response to BAM7 treatment (15 μM). The time lapse images reveal progressive cellular shrinkage, membrane blebbing, and the formation of apoptotic bodies. 1, 20 min; 2, 6 h; 3, 12 h; 4, 12.5 h; 5, 13.5 h, 6, 14.5 h; 7, 16.5 h; 8, 17.5 h.

FIG. 9A-9D are bar graphs that shows formula (I) compounds selectively impair the viability of Bak$^{-/-}$ MEFs, but had no effect on MEFs that lack BAX (Bax$^{-/-}$) or both BAX and BAK (Bax$^{-/-}$Bak$^{-/-}$). For each triplet of bars centered on the indicated x-axis value, the BAK knockout result is the left-most bar; the BAX knockout result is the middle bar; and the double knockout result is the right-most bar.

Figure 10A:
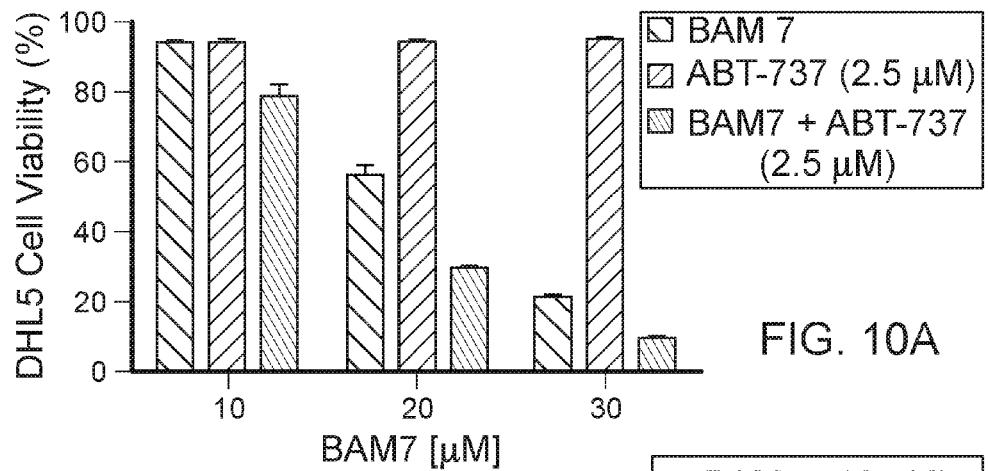

FIG. 10A shows that BAM7 dose-responsively impairs the viability of DHL5 diffuse large B-cell lymphoma (DLBCL) cells and the addition of BCL-2/BCL-XL inhibitor ABT-737 further sensitizes the cells to BAM7 anti-cancer activity.

Figure 10B:
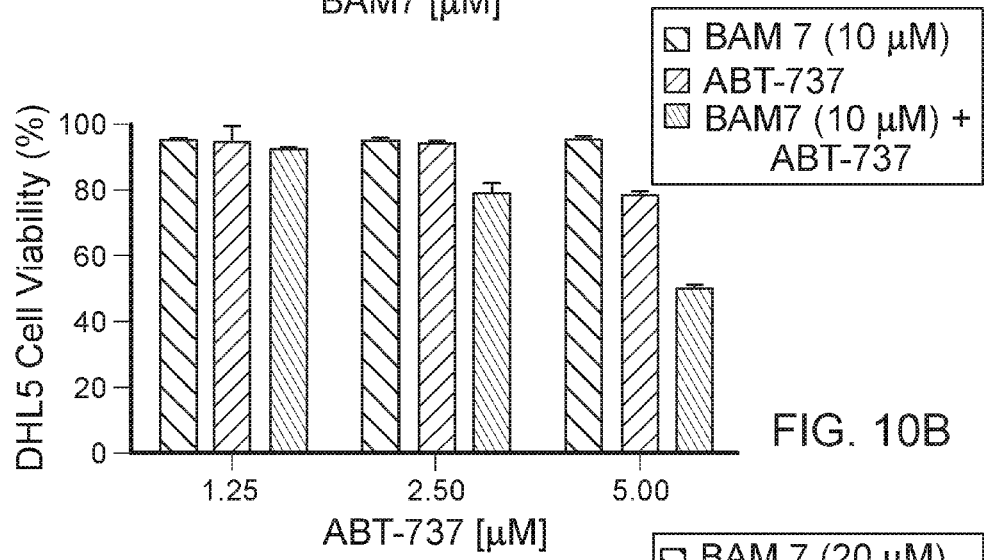
Figure 10C:
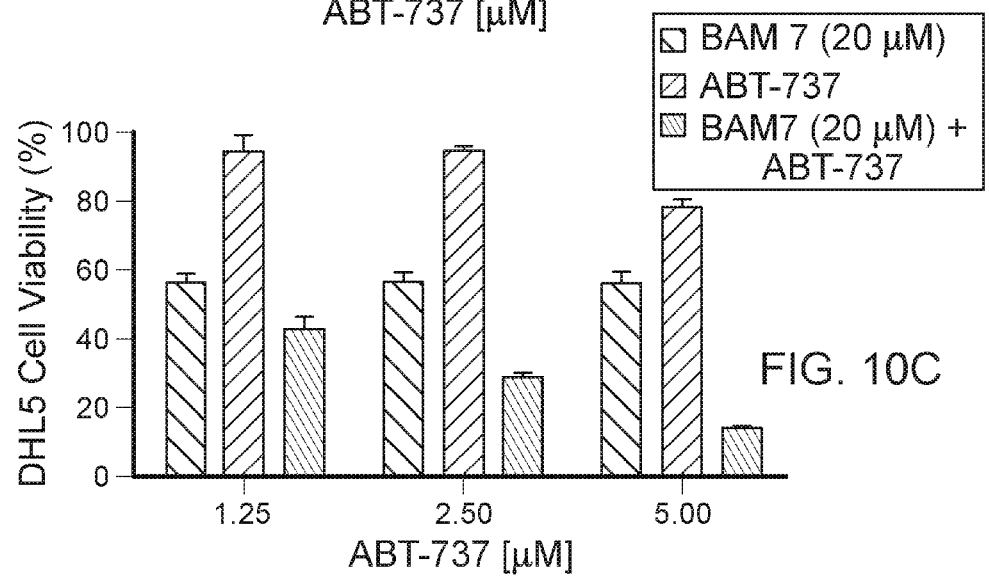

FIGS. 10B and 10C are bar graphs showing that BAM7 can sensitize DHL5 DLBCL cells to ABT-737, which is otherwise less effective in DHL5 cells due to the expression of anti-apoptotic proteins that lie outside its binding spectrum.

In FIGS. 10A-10C, for each triplet of bars centered on the indicated x-axis value, the BAM7 (10 μM) is the left-most bar; the ABT-737 is the middle bar; and BAM7 (10 μM) plus ABT-737 is the right-most bar.

FIG. 11 includes the chemical structures and binding data for formula (I) compounds.

FIG. 12 includes the chemical structures of some formula (I) compounds.

Figure 4A:
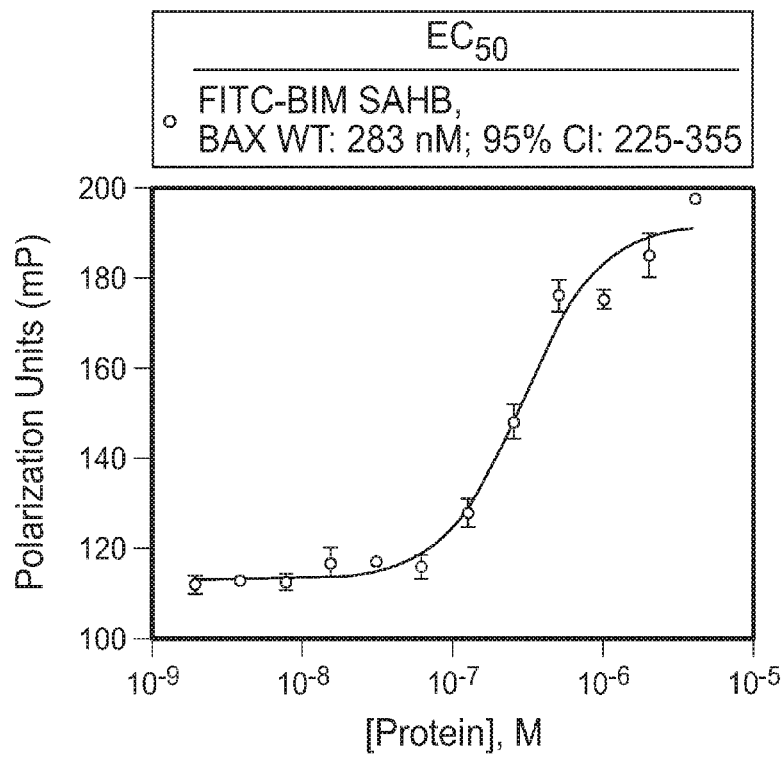
FIG. 4A is a graph showing the direct binding interaction between FITC-BIM SAHB and recombinant full-length BAX. This formed the basis for developing a competitive fluorescence polarization binding assay to screen for BAMs.
Figure 4B:
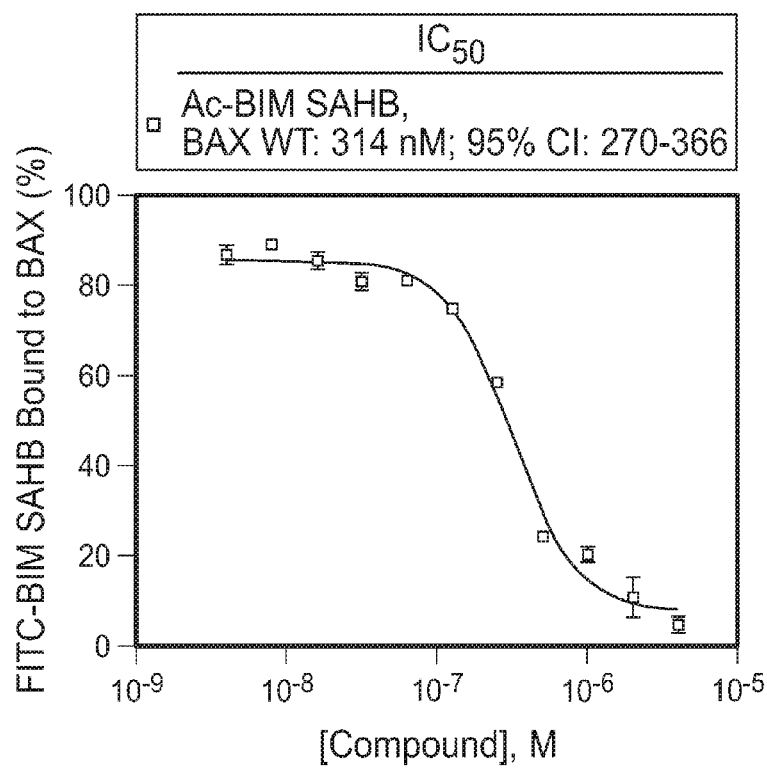
FIG. 4B is a graph showing that acetylated BIM SAHB (Ac-BIM SAHB), which effectively competed with FITC-BIM SAHB for BAX binding, served as a positive control for the assay.
Figure 4C:
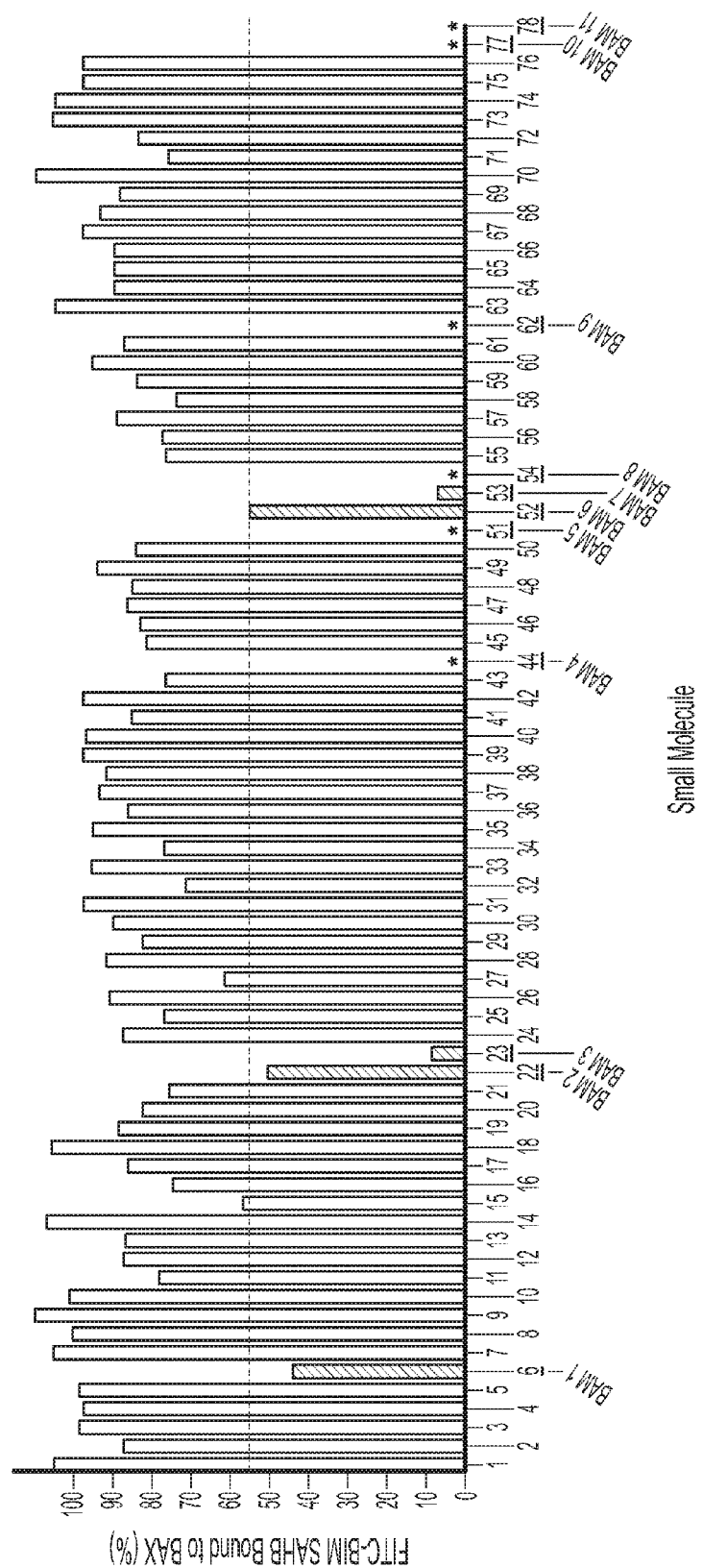
FIG. 4C is a bar graph showing that eleven molecules achieved >55% displacement of FITC-BIM SAHB at the 100 µM screening dose. These eleven compounds were advanced to dose-responsive competitive binding analysis. *, no detectable FITC-BIM SAHB binding.
Figure 13:
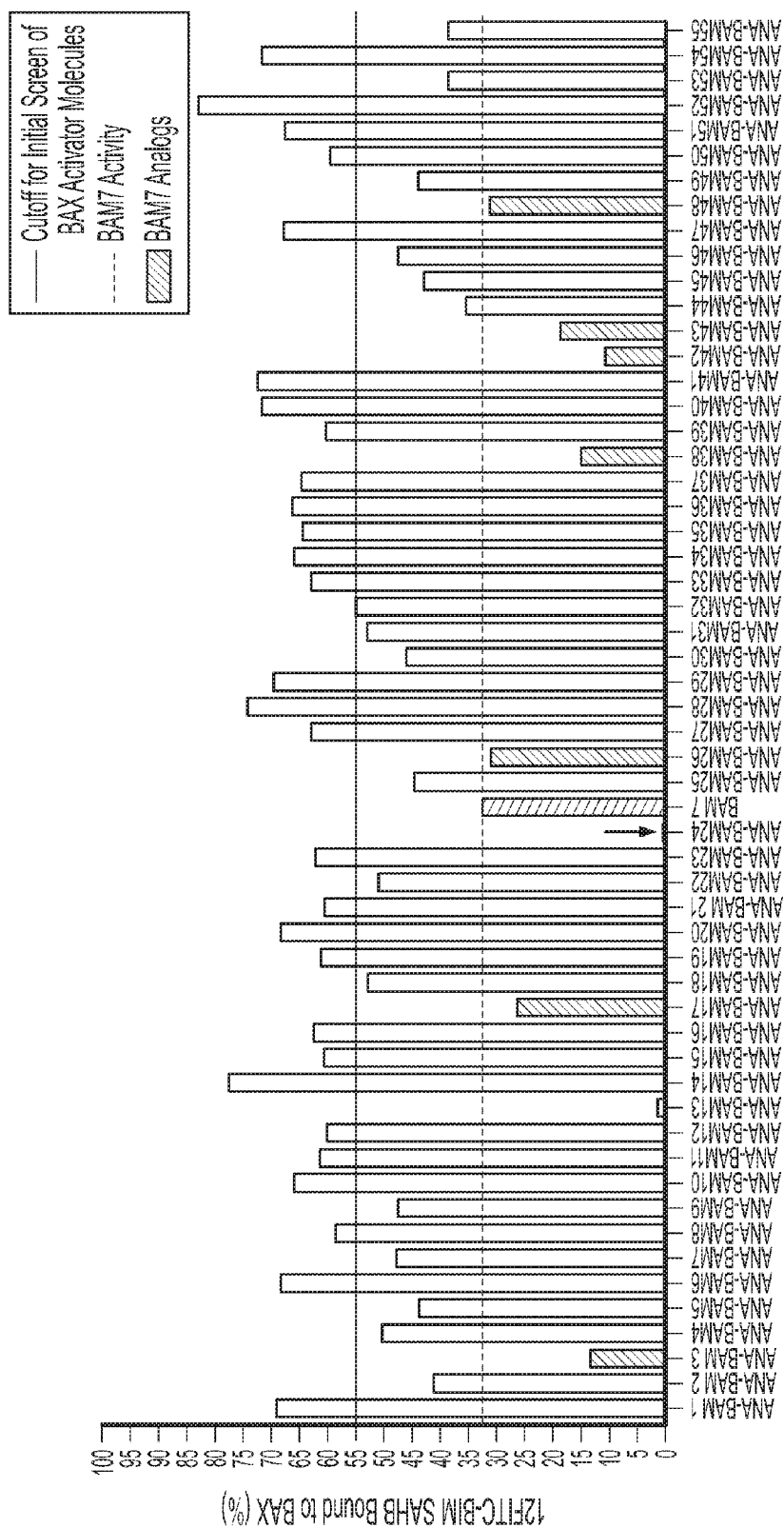

FIG. 13 includes data that supplements the screening data provided in FIG. 4C.

Figure 14:
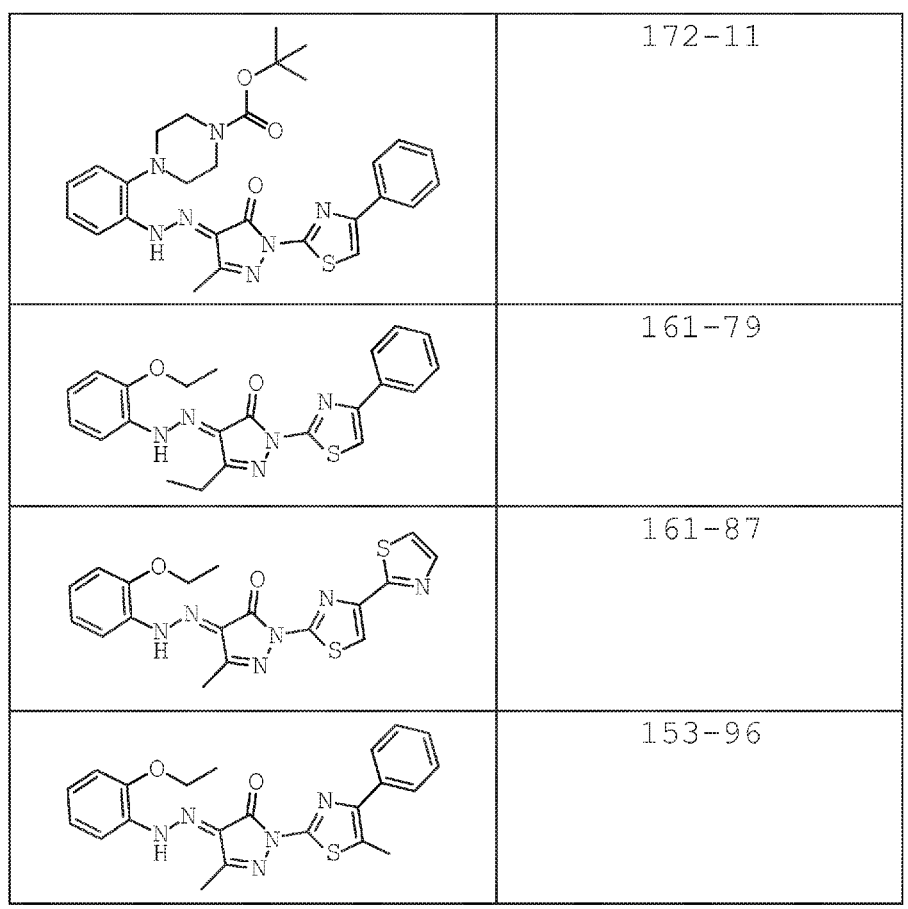
Figure 15A:
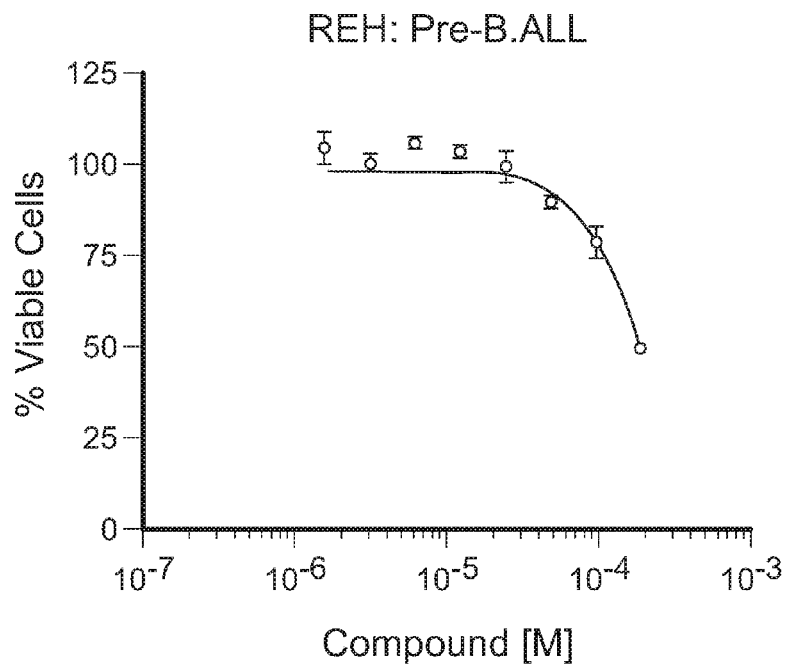
Figure 15B:
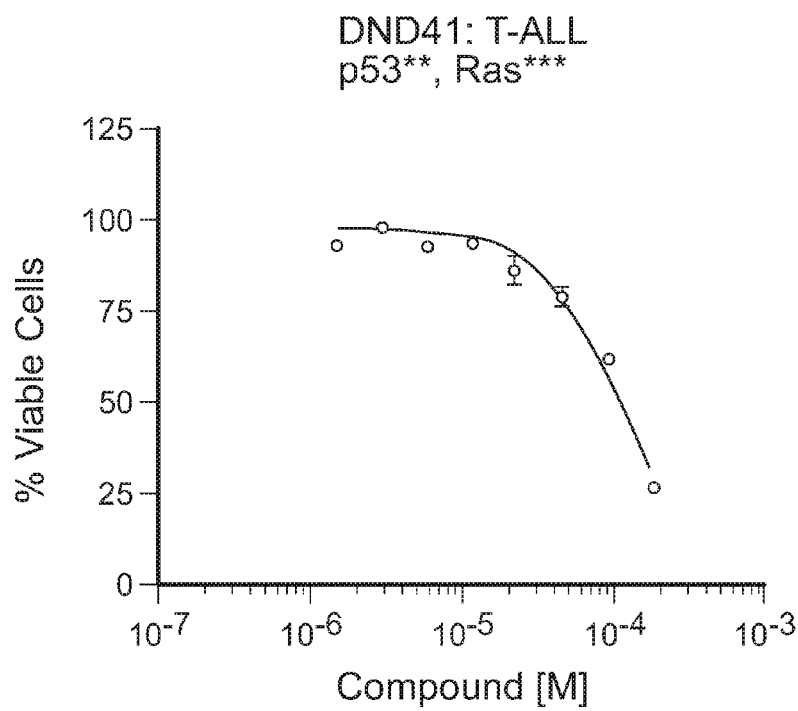
Figure 15C:
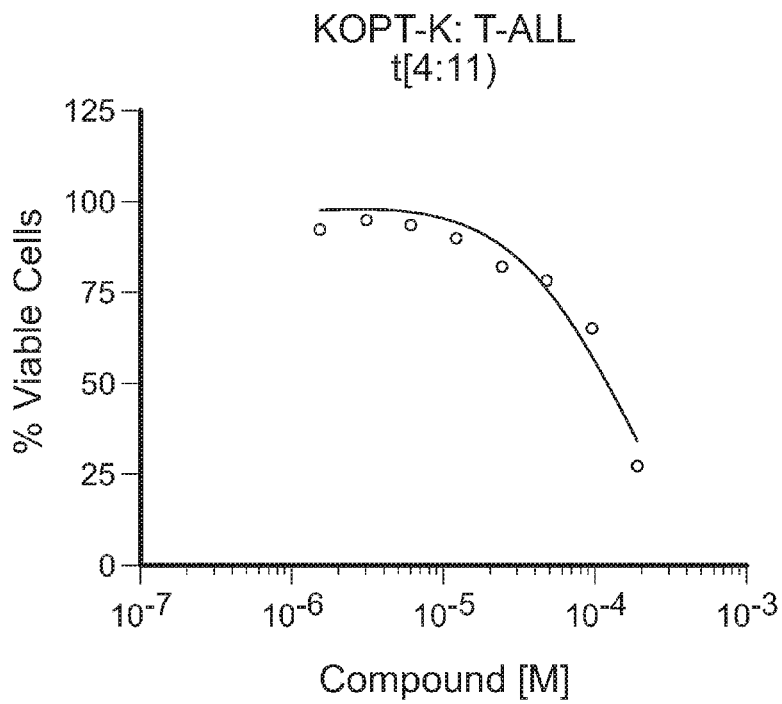
Figure 15D:
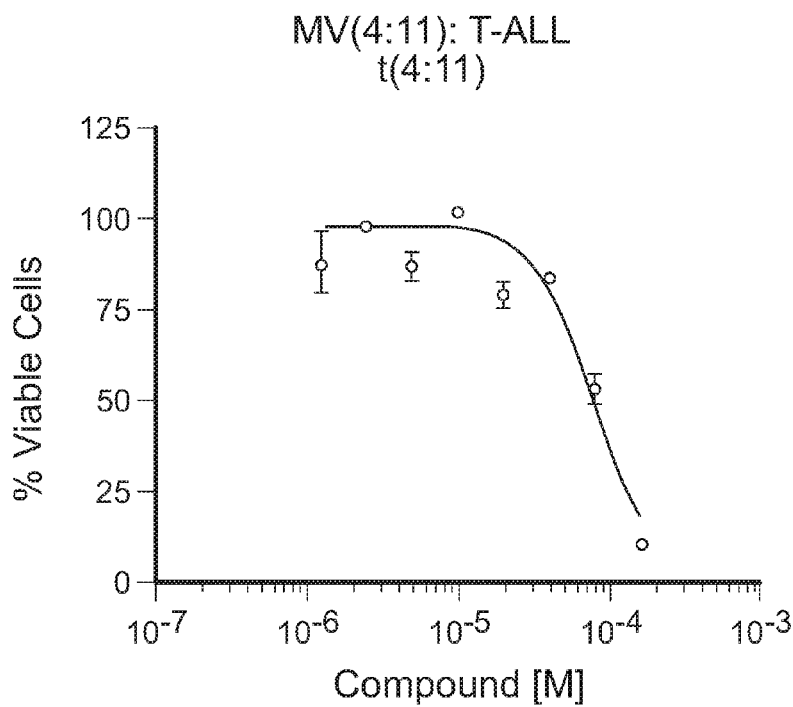
Figure 15E:
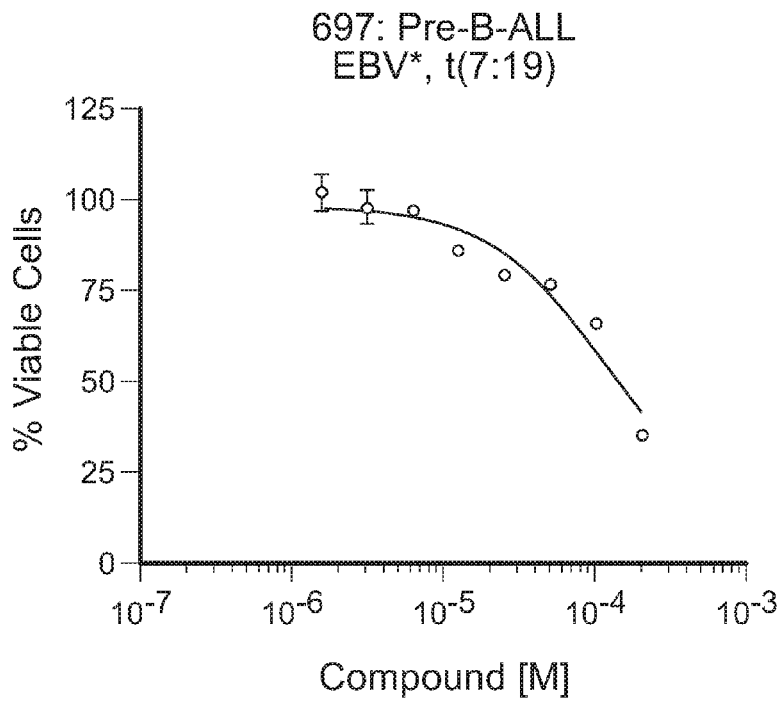
Figure 15F:
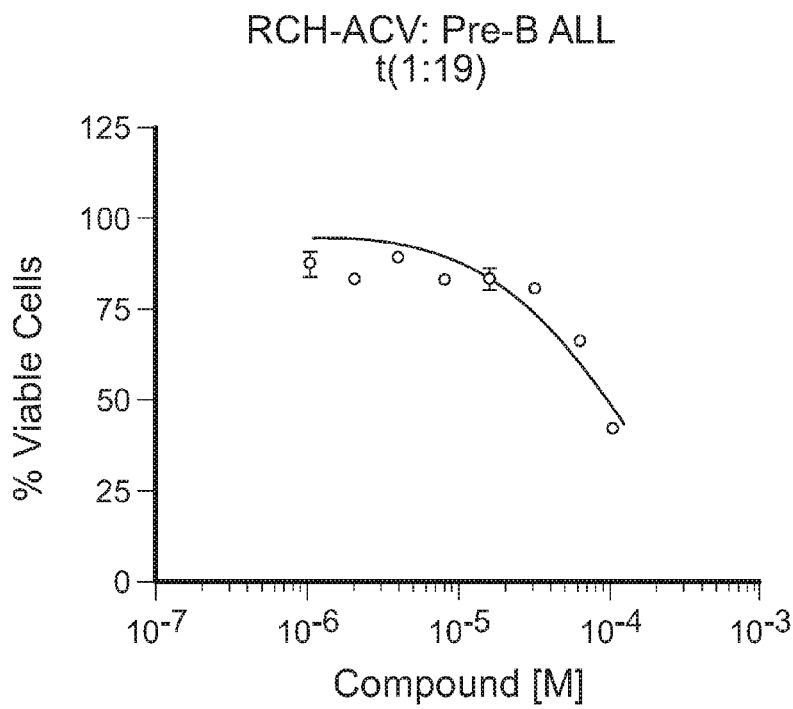
Figure 15G:
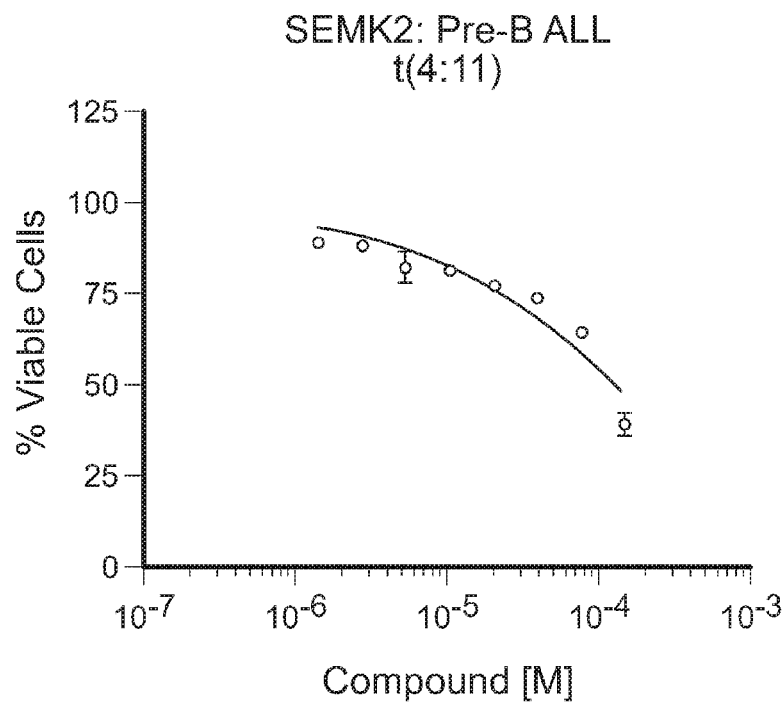
Figure 15H:
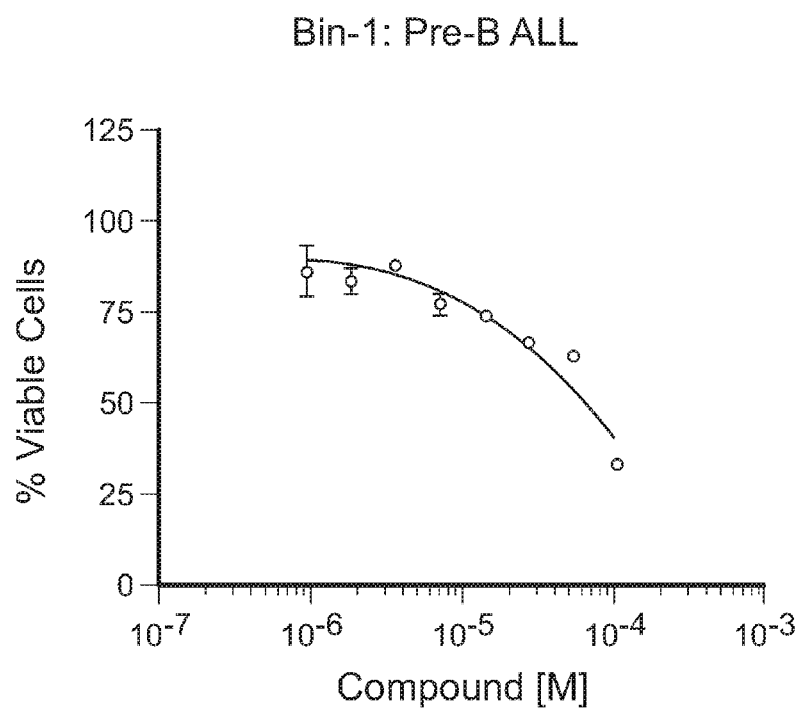

FIG. 14 includes the chemical structures of some formula (I) compounds that are encompassed by formula (I-A) or (I-B).

FIGS. 15A-15H are graphs that demonstrate the anti-leukemic activity of BAM7.

Figure 16:
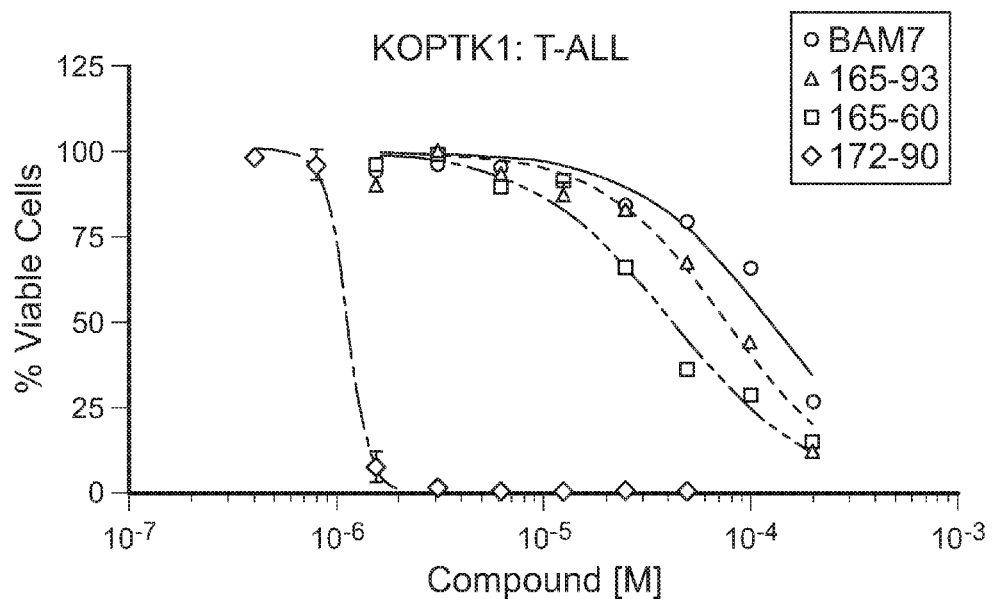

FIG. 16 is a graph that compares the anti-leukemic activity of BAM7 to compounds 165-93, 165-60, and 172-90 (see FIG. 14).

Figure 17:
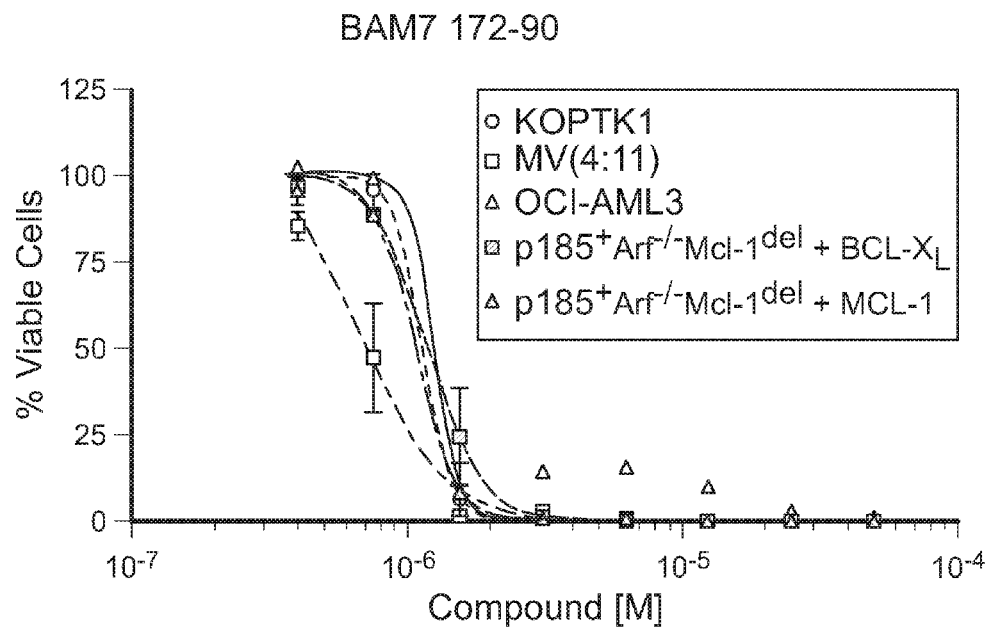

FIG. 17 is a graph that demonstrates the broad anti-leukemic activity of compound 172-90.

FIGS. 18A and 18B are graphs that demonstrate that compound 172-90 overcomes the apoptotic resistance conferred by BCL-2 family anti-apoptotic members BCL-XL and MCL-1; whereas the BCL-2/BCL-XL selective inhibitor ABT-737 induces cell death of the BCL-XL-dependent leukemia cell line, significant resistance to ABT-737 is manifest in the isogenic MCL-1 dependent leukemia cell line. In contrast, FIGS. 18C and 18D are graphs that demonstrate that compound 172-90 induces dose-responsive caspase 3/7 activity and cell death in both cell lines, overcoming formidable apoptotic resistance.

FIGS. 19A-19F are reaction schemes showing the syntheses used to prepare a variety of compounds of formula (I), such as those delineated in FIG. 14.

DETAILED DESCRIPTION

This application features pyrazol-3-one compounds that activate a pro-apoptotic function of BAX, making them therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of cells (e.g., diseased or damaged cells; e.g., insufficient apoptosis of diseased or damaged cells; or lack of or reduced apoptosis of diseased or damaged cells). Examples of such diseases, disorders, and conditions include (but are not limited to) those associated with blockade(s) of cell death pathways (e.g., over-expression of anti-apoptotic BCL-2 proteins), e.g., hyperproliferative diseases, such as cancer. While not wishing to be bound by theory, it is believed that the compounds described herein induce and increase apoptosis in target cells (e.g., pathogenic cells including, but not limited to, cancer cells), thereby suppressing tumor growth and/or proliferation. It is further believed that increasing apoptosis in said target cells reestablishes the normal apoptotic control that, during homeostasis, is associated with a regulated balance between pro- and anti-apoptotic protein functions.

Compounds

This application features pyrazol-3-one compounds having formula (I) below as well as compositions and methods that include the formula (I) compounds.

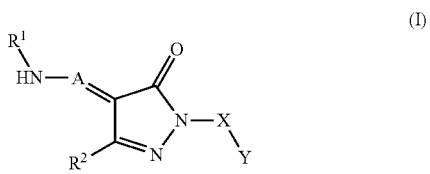
(I)

Here and throughout this specification, the attendant variables $R^1$, $R^2$, A, X, and Y (and any sub-variables) can be as defined anywhere herein.

It is appreciated that certain features of the invention, which are, for clarity, described in the context of separate embodiments, can also be provided in combination in a single embodiment. Conversely, various features of the invention which are, for brevity, described in the context of a single embodiment, can also be provided separately or in any suitable sub-combination.

Thus, for ease of exposition, it is also understood that where in this specification, a variable (e.g., $R^1$) is defined by "as defined anywhere herein" (or the like), the definitions for that particular variable include the first occurring and broadest generic definition as well as any sub-generic and specific definitions delineated anywhere in this specification.

Variable X

In some embodiments, X is heteroaryl, which contains 5 ring atoms, wherein from 1-2 of the ring atoms is/are independently selected from N, NH, N($C_1$-$C_3$ alkyl), O, and S; wherein:
  X is connected to the pyrazolone nitrogen via a ring carbon atom in X; and
  X is optionally further substituted with 1 $R^a$:
or
  X is phenyl optionally substituted with from 1-5 $R^a$.

In some embodiments, X is heteroaryl, which contains 5 ring atoms, wherein from 1-2 of the ring atoms is/are independently selected from N, NH, N($C_1$-$C_3$ alkyl), O, and S; wherein:
  X is connected to the pyrazolone nitrogen via a ring carbon atom in X; and
  X is optionally further substituted with 1 $R^a$:

In some embodiments, X contains 2 ring atoms independently selected from N, NH, N($C_1$-$C_3$ alkyl), O, and S (e.g., selected from N and S; e.g., selected from N and NH).

In certain embodiments, one of the two ring atoms is independently selected from N, NH, and N($C_1$-$C_3$ alkyl) (e.g., N), and the other ring atom is independently selected from N, NH, N($C_1$-$C_3$ alkyl), O, and S (e.g., the other ring atom is O or S, e.g., S; or e.g., NH).

As an example, X can have formula X-1:

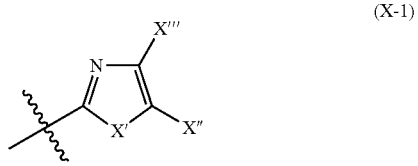
(X-1)

in which:
  X' is NH, O, or S; and
  one of X" and X'" is Y, and the other of X" and X'" is H or $R^a$.

Embodiments in which X has formula X-1 can include one or more of the following features.

X' is S. X' is NH.

X'" is Y, which can be as defined anywhere herein, and X" is H or $R^a$.

X' is S; and X'" is Y, which can be as defined anywhere herein, and X" is H or $R^a$ (e.g., X" is H).

X' is NH; and X'" is Y, which can be as defined anywhere herein, and X" is H or $R^a$ (e.g., X" is H).

X" is H.

X" is $R^a$. In certain embodiments, $R^a$ is $C_1$-$C_8$ (e.g., $C_1$-$C_6$, $C_1$-$C_3$)alkyl (e.g., $CH_3$). In other embodiments, $R^a$ is phenyl that is optionally substituted with from 1-4 $R^e$. In still other embodiments, $R^a$ is or $C_3$-$C_8$ cycloalkyl which is optionally substituted with from 1-4 independently selected $C_1$-$C_4$ alkyl groups.

X" is Y, which can be as defined anywhere herein; and X'" is H or $R^a$. In embodiments, X' is S or NH (e.g., S).

Variable Y

In some embodiments, Y is:
  (i) $C_6$-$C_{10}$ aryl, which is optionally substituted with from 1-5 independently selected $R^b$; or
  (ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^b$; or
  (iii) $C_1$-$C_6$ alkyl or $C_1$-$C_6$ haloalkyl, each of which is optionally substituted with —OH, —$NH_2$, or —SH.

In some embodiments, Y is $C_6$-$C_{10}$ aryl, which is optionally substituted with from 1-5 independently selected $R^b$. In certain embodiments, Y is phenyl, which is optionally substituted with from 1-5 independently selected $R^b$. In certain embodiments, Y is unsubstituted phenyl.

In some embodiments, Y is heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^b$.

In some embodiments, Y is heteroaryl, which contains from 5-6 ring atoms, wherein from 1-4 (e.g., 1-2) of the ring atoms is independently selected from N, NH, N($C_1$-$C_3$ alkyl), O, and S; and wherein said heteroaryl ring is optionally substituted with from 1-3 independently selected $R^b$.

In some embodiments, Y is $C_1$-$C_6$ alkyl or $C_1$-$C_6$ haloalkyl, each of which is optionally substituted with —OH, —$NH_2$, or —SH (e.g., $C_1$-$C_6$ alkyl, which is optionally substituted with —OH, —$NH_2$, or —SH; e.g., $C_1$-$C_6$ alkyl, such as $CH_3$).

Variable $R^1$ $R^1$ is:
  (i) $C_6$-$C_{10}$ aryl, which is optionally substituted with from 1-5 independently selected $R^c$; or
  (ii) heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^c$; or
  (iii) —C(O)—($C_6$-$C_{10}$ aryl or heteroaryl, which contains from 5-10 ring atoms as defined in $R^1$ definition (i) and (ii), respectively); or
  (iv) hydrogen.

In some embodiments, $R^1$ is any one, two, or three of the above (e.g., (i) and/or (ii) and one of (iii) or (iv); e.g., (i) and/or (ii); e.g., (iii) and/or (iv)).

In some embodiments, $R^1$ is $C_6$-$C_{10}$ aryl, which is optionally substituted with from 1-5 independently selected $R^c$.

In certain embodiments, $R^1$ is phenyl, which is substituted with from 1-5 (e.g., 1-3, 1-2, or 1) independently selected $R^c$.

In certain embodiments, each occurrence of $R^c$ is, independently, selected from any one the substituents delineated collectively in (aaa), (bbb), (ccc), and (ddd) below:

(aaa) $C_1$-$C_6$ alkoxy, $C_1$-$C_6$ alkyl, $C_1$-$C_6$ haloalkyl, —NH($C_1$-$C_6$ alkyl), N($C_1$-$C_6$ alkyl)$_2$, or —NHC(O)($C_1$-$C_6$ alkyl), each of which is optionally substituted with —OH, —NH$_2$, or —SH;

(bbb) C(O)OH; —C(O)O($C_1$-$C_6$ alkyl); —OC(O)($C_1$-$C_6$ alkyl); —SO$_2$NH$_2$; —SO$_2$NH($C_1$-$C_6$ alkyl); or —SO$_2$N($C_1$-$C_6$ alkyl)$_2$; or —C(O)O—(CH$_2$)$_{1-3(e.g., 1)}$—C(O)-(phenyl optionally substituted as defined in (ddd) below (e.g., —C(O)O—CH$_2$—C(O)-(phenyl);

(ccc) $C_3$-$C_6$ cycloalkoxy or L-heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., a bond); e.g., $R^c$ is morpholino or piperazinyl; and (ddd) phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH.

In certain embodiments, each occurrence of $R^c$ is, independently, selected from:

$C_1$-$C_6$ alkoxy;

$C_1$-$C_6$ alkoxy (e.g., $C_2$-$C_6$ alkoxy, e.g., ethoxy); or $C_1$-$C_6$ alkoxy (e.g., $C_2$-$C_6$ alkoxy, e.g., ethoxy) that is substituted with —NH$_2$;

$C_1$-$C_6$ alkyl;

—NHC(O)($C_1$-$C_6$ alkyl)

—C(O)OH;

L-heterocyclyl containing from 5-7 (e.g., 5-6, or 6) ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., a bond); e.g., $R^c$ is morpholino or piperazinyl; and phenyl or heteroaryl containing from 5-6 ring atoms, wherein from 1-2 of the ring atoms of the heteroaryl is independently selected from N, NH, N($C_1$-$C_3$ alkyl), O, and S; wherein each of said phenyl and heteroaryl is optionally substituted with from 1-3 substituents independently selected from halo; hydroxyl; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH.

In certain embodiments, $R^c$ is $C_1$-$C_6$ alkoxy (e.g., ethoxy e.g., containing branched alkyl, such as iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy) that is substituted with —NH$_2$.

In certain embodiments, $R^1$ has formula A:

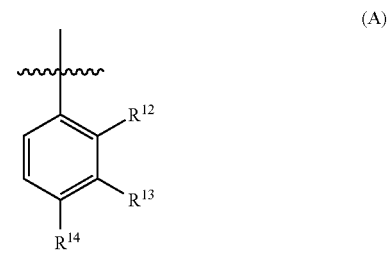

(A)

wherein one or two of $R^{12}$, $R^{13}$, and $R^{14}$ is(are) an independently selected $R^c$, and the other(s) is(are) hydrogen.

Embodiments in which $R^1$ has formula A can include one or more of the following features.

$R^{12}$ is $R^c$.

$R^{13}$ is H.

R14 is H.

$R^{14}$ is $R^c$.

$R^{12}$ is $R^c$, and each of $R^{13}$ and $R^{14}$ is H.

$R^{14}$ is $R^c$, and each of $R^{12}$ and $R^{13}$ is H.

In some of the above described embodiments, $R^c$ is $C_1$-$C_6$ alkoxy (e.g., ethoxy or iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy).

In embodiments, $R^c$ can be $C_1$-$C_6$ alkoxy (e.g., $C_2$-$C_6$ alkoxy, e.g., ethoxy; e.g., containing branched alkyl, such a iso-propoxy) that is substituted with —NH$_2$.

In some of the above described embodiments, $R^c$ is —C(O)OH (or a salt thereof, e.g., sodium salt thereof).

In some of the above described embodiments, $R^c$ is L-heterocyclyl containing from 5-7 (e.g., 6) ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups; and wherein L is a bond or $C_1$-$C_6$ alkylene (e.g., L is a bond or CH$_2$; e.g., a bond); e.g., $R^c$ is morpholino or piperazinyl.

$R^{13}$ is H, and each of $R^{12}$ and $R^{14}$ is $R^c$. In certain embodiments, one of $R^{12}$ and $R^{14}$ is $C_1$-$C_6$ alkoxy (e.g., ethoxy), and the other of $R^{12}$ and $R^{14}$ is independently selected from:

$C_1$-$C_6$ alkoxy;

$C_1$-$C_6$ alkoxy (e.g., $C_2$-$C_6$ alkoxy, e.g., ethoxy); or $C_1$-$C_6$ alkoxy (e.g., $C_2$-$C_6$ alkoxy, e.g., ethoxy) that is substituted with —NH$_2$;

$C_1$-$C_6$ alkyl;

—C(O)OH;

—NHC(O)($C_1$-$C_6$ alkyl);

L-heterocyclyl containing from 5-7 ring atoms, wherein from 1-2 of the ring atoms of the heterocyclyl is independently selected from N, NH, N($C_1$-$C_6$ alkyl), NC(O)(C$_1$-C$_6$ alkyl), NC(O)O(C$_1$-C$_6$ alkyl), O, and S; and each of which is optionally substituted with from 1-3 independently selected C$_1$-C$_4$ alkyl groups; and wherein L is a bond or C$_1$-C$_6$ alkylene (e.g., a bond); e.g., R$^c$ is morpholino or piperazinyl; and phenyl or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; —C(O)(C$_1$-C$_6$ alkyl); C(O)OH; —C(O)O(C$_1$-C$_6$ alkyl); nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy; C$_1$-C$_6$ thioalkoxy; C$_1$-C$_6$ thiohaloalkoxy; C$_1$-C$_6$ alkyl, and C$_1$-C$_6$ haloalkyl, wherein said alkyl or alkyl portion is optionally substituted with —OH, —NH$_2$, or —SH.

In some embodiments, R$^1$ is heteroaryl, which contains from 5-10 ring atoms, wherein from 1-4 of the ring atoms is independently selected from N, NH, N(C$_1$-C$_3$ alkyl), O, and S; and wherein said heteroaryl ring is optionally substituted with from 1-3 independently selected R$^c$.

In certain embodiments, R$^1$ is heteroaryl, which contains from 5-6 ring atoms, wherein from 1-4 (e.g., 1-2) of the ring atoms is independently selected from N, NH, N(C$_1$-C$_3$ alkyl), O, and S; and wherein said heteroaryl ring is optionally substituted with from 1-3 (e.g., 1-2 or 1) independently selected R$^c$. For example, R$^1$ can be thiazolyl.

In other embodiments, R$^1$ is heteroaryl, which contains from 8-10 ring atoms, wherein from 1-4 (e.g., 1-2) of the ring atoms is independently selected from N, NH, N(C$_1$-C$_3$ alkyl), O, and S; and wherein said heteroaryl ring is optionally substituted with from 1-3 (e.g., 1-2 or 1) independently selected R$^c$. For example, R$^1$ can be indazolyl.

In some embodiments, R$^1$ is hydrogen.

In some embodiments, R$^1$ is —C(O)—(C$_6$-C$_{10}$ aryl or heteroaryl, which contains from 5-10 ring atoms as defined in R$^1$ definition (i) and (ii), respectively); e.g., —C(O)-(heteroaryl, which contains from 5-10 (e.g., 5-6, e.g., 5) ring atoms as defined in R$^1$ definition (i) and (ii), respectively), such as —C(O)-(thiazolyl).

Variable R$^2$

In some embodiments, R$^2$ is C$_1$-C$_8$ alkyl (e.g., C$_1$-C$_6$ alkyl, e.g., C$_1$-C$_3$ alkyl, e.g., CH$_3$).

In some embodiments, R$^2$ is phenyl that is optionally substituted with from 1-4 R$^e$. In certain embodiments, R$^2$ is unsubstituted phenyl.

In some embodiments, R$^2$ is heteroaryl containing from 5-6 (e.g., 5) ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$. In certain embodiments, R$^2$ is heteroaryl containing from 5 ring atoms, wherein from 1-4 of the ring atoms is independently selected from N, NH, N(C$_1$-C$_3$ alkyl), NC(O)(C$_1$-C$_6$ alkyl), O, and S; and wherein said heteroaryl is optionally substituted with from 1-3 R$^e$; e.g., thienyl or furyl.

In some embodiments, R$^2$ is C$_3$-C$_8$ cycloalkyl which is optionally substituted with from 1-4 independently selected C$_1$-C$_4$ alkyl groups.

Variable A

In some embodiments, A is N.

Non-Limiting Combinations of Attendant Variables

In some embodiments:

A is N;

X contains 2 ring atoms independently selected from N, NH, N(C$_1$-C$_3$ alkyl), O, and S, and one of the ring atoms is independently selected from N, NH, and N(C$_1$-C$_3$ alkyl) (e.g., N), and the other ring atom is independently selected from N, NH, N(C$_1$-C$_3$ alkyl), O, and S (e.g., the other ring atom is S or NH, e.g., S); and R$^1$ is C$_6$-C$_{10}$ aryl, which is optionally substituted with from 1-5 independently selected R$^c$ (e.g., R$^1$ is phenyl, which is substituted with from 1-5 (e.g., 1-3, 1-2, or 1) independently selected R$^c$), which R$^c$ can be as defined anywhere herein.

In some embodiments the compound has formula I-A:

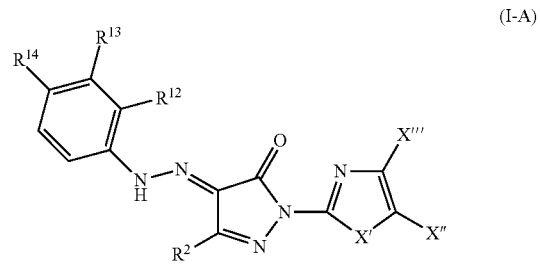

(I-A)

wherein:

X' is NH, O, or S (e.g., S or NH, e.g., S);

one of X" and X'" is Y, and the other of X" and X'" is H or R$^a$; and one or two of R$^{12}$, R$^{13}$, and R$^{14}$ is(are) an independently selected R$^c$, and the other(s) is(are) hydrogen; R$^2$ can be as defined anywhere herein.

Embodiments in which the compound has formula I-A can include one or more of the following features.

X' is S, X'" is Y, and X" is H or R$^a$ (e.g., X" is H).

X' is NH, X'" is Y, and X" is H or R$^a$ (e.g., X" is H).

R$^a$ is C$_1$-C$_8$ alkyl (e.g., C$_1$-C$_6$ alkyl, e.g., C$_1$-C$_3$ alkyl, e.g., CH$_3$).

Y is C$_6$-C$_{10}$ aryl, which is optionally substituted with from 1-5 independently selected R$^b$ (e.g., Y is unsubstituted phenyl).

R$^{12}$ is R$^c$, and each of R$^{13}$ and R$^{14}$ is H; or R$^{14}$ is R$^c$, and each of R$^{12}$ and R$^{14}$ is H.

Each occurrence of R$^c$ is, independently, selected from:

C$_1$-C$_6$ alkoxy;

C$_1$-C$_6$ alkoxy (e.g., C$_2$-C$_6$ alkoxy, e.g., ethoxy); or C$_1$-C$_6$ alkoxy (e.g., C$_2$-C$_6$ alkoxy, e.g., ethoxy) that is substituted with —NH$_2$;

C$_1$-C$_6$ alkyl;

—C(O)OH;

—NHC(O)(C$_1$-C$_6$ alkyl);

L-heterocyclyl containing from 5-7 ring atoms, wherein from 1-2 of the ring atoms of the heterocyclyl is independently selected from N, NH, N(C$_1$-C$_6$ alkyl), NC(O)(C$_1$-C$_6$ alkyl), NC(O)O(C$_1$-C$_6$ alkyl), O, and S; and each of which is optionally substituted with from 1-3 independently selected C$_1$-C$_4$ alkyl groups; and wherein L is a bond or C$_1$-C$_6$ alkylene (e.g., a bond); e.g., R$^c$ is morpholino or piperidinyl; and phenyl or heteroaryl containing from 5-6 ring atoms, wherein from 1-2 of the ring atoms of the heteroaryl is independently selected from N, NH, N(C$_1$-C$_3$ alkyl), O, and S; wherein each of said phenyl and heteroaryl is optionally substituted with from 1-3 substituents independently selected from halo; hydroxyl; cyano; —C(O)(C$_1$-C$_6$ alkyl); C(O)OH; —C(O)O(C$_1$-C$_6$ alkyl); nitro; —NH$_2$; —NH(C$_1$-C$_6$ alkyl), N(C$_1$-C$_6$ alkyl)$_2$, —NHC(O)(C$_1$-C$_6$ alkyl), C$_1$-C$_6$ alkoxy; C$_1$-C$_6$ haloalkoxy;

$C_1$-$C_6$ thioalkoxy; $C_1$-$C_6$ thiohaloalkoxy; $C_1$-$C_6$ alkyl, and $C_1$-$C_6$ haloalkyl, wherein said alkyl or alkyl portion is optionally substituted with —OH, —NH$_2$, or —SH.

$R^c$ is $C_1$-$C_6$ alkoxy (e.g., ethoxy; e.g., containing branched alkyl, such as iso-propoxy).

$R^c$ is $C_1$-$C_6$ alkoxy (e.g., $C_2$-$C_6$ alkoxy, e.g., ethoxy; e.g., containing branched alkyl, such a iso-propoxy).

$R^c$ is $C_1$-$C_6$ alkoxy (e.g., $C_2$-$C_6$ alkoxy, e.g., ethoxy; e.g., containing branched alkyl, such a iso-propoxy) that is substituted with —NH$_2$.

$R^2$ is $C_1$-$C_8$ alkyl (e.g., $C_1$-$C_6$ alkyl, e.g., $C_1$-$C_3$ alkyl, e.g., CH$_3$). $R^2$ is phenyl that is optionally substituted with from 1-4 $R^e$. $R^2$ is heteroaryl containing from 5-6 (e.g., 5) ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 W.

In some embodiments of formula I-A:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl); and
$R^2$ is $C_1$-$C_8$ alkyl (e.g., $C_1$-$C_6$ alkyl, e.g., $C_1$-$C_3$ alkyl, e.g., CH$_3$).

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl);
$R^2$ is $C_1$-$C_8$ alkyl (e.g., $C_1$-$C_6$ alkyl, e.g., $C_1$-$C_3$ alkyl, e.g., CH$_3$, and
$R^{12}$ is:
—C(O)OH; or
$C_1$-$C_6$ alkoxy (e.g., $C_2$-$C_6$ alkoxy, e.g., ethoxy; e.g., containing branched alkyl, such a iso-propoxy) that is optionally substituted with —NH$_2$, such as —OCH$_2$CH$_3$ or —OCH$_2$CH$_2$NH$_2$; or
heterocyclyl containing from 5-7 (e.g., 6) ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups, such as an optionally substituted piperazinyl ring.

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl);
$R^2$ is $C_1$-$C_8$ alkyl (e.g., $C_1$-$C_6$ alkyl, e.g., $C_1$-$C_3$ alkyl, e.g., CH$_3$, and
$R^{12}$ is $C_1$-$C_6$ alkoxy (e.g., $C_2$-$C_6$ alkoxy, e.g., ethoxy; e.g., containing branched alkyl, such a iso-propoxy) that is optionally substituted with —NH$_2$, such as —OCH$_2$CH$_3$ or —OCH$_2$CH$_2$NH$_2$; (see e.g., compounds 172-90 and 165-93).

In some embodiments of formula I-A:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl); and
$R^2$ is phenyl that is optionally substituted with from 1-4 $R^e$ (e.g., each occurrence of $R^e$ is, independently, halo; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted phenyl).

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl);
$R^2$ is phenyl that is optionally substituted with from 1-4 $R^e$ (e.g., each occurrence of $R^e$ is, independently, halo; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted phenyl); and
$R^{12}$ is
—C(O)OH; or
$C_1$-$C_6$ alkoxy (e.g., $C_2$-$C_6$ alkoxy, e.g., ethoxy; e.g., containing branched alkyl, such a iso-propoxy) that is optionally substituted with —NH$_2$, such as —OCH$_2$CH$_3$ or —OCH$_2$CH$_2$NH$_2$; or
heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups, such as an optionally substituted piperazinyl ring.

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., CH$_3$); (e.g., X'' is H or CH$_3$; e.g., X'' is H);
Y is $C_6$-$C_{10}$ aryl, which is optionally substituted with from 1-5 independently selected $R^b$ (e.g., Y is unsubstituted phenyl);
$R^2$ is phenyl that is optionally substituted with from 1-4 $R^e$ (e.g., each occurrence of $R^e$ is, independently, halo; cyano; —C(O)($C_1$-$C_6$ alkyl); C(O)OH; —C(O)O($C_1$-$C_6$ alkyl); nitro; —NH$_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted phenyl); and
$R^{12}$ is —C(O)OH (see, e.g., compound 165-74).

In some embodiments of formula I-A:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., $CH_3$); (e.g., X'' is H or $CH_3$; e.g., X'' is H);
Y is $C_6$-$C_{10}$ aryl, which is optionally substituted with from 1-5 independently selected $R^b$ (e.g., Y is unsubstituted phenyl); and
$R^2$ is heteroaryl containing from 5-6 (e.g., 5) ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$, such as thienyl, furanyl, or thiazolyl; (e.g., each occurrence of $R^e$ is, independently, halo; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted heteroaryl, such as unsubstituted thienyl, furanyl, or thiazolyl).

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., $CH_3$); (e.g., X'' is H or $CH_3$; e.g., X'' is H);
Y is $C_6$-$C_{10}$ aryl, which is optionally substituted with from 1-5 independently selected $R^b$ (e.g., Y is unsubstituted phenyl);
$R^2$ is heteroaryl containing from 5-6 (e.g., 5) ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$, such as thienyl, furanyl, or thiazolyl; (e.g., each occurrence of $R^e$ is, independently, halo; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted heteroaryl, such as unsubstituted thienyl, furanyl, or thiazolyl); and
$R^{12}$ is
—C(O)OH; or
$C_1$-$C_6$ alkoxy (e.g., $C_2$-$C_6$ alkoxy, e.g., ethoxy; e.g., containing branched alkyl, such a iso-propoxy) that is optionally substituted with —$NH_2$, such as —$OCH_2CH_3$ or —$OCH_2CH_2NH_2$; or
heterocyclyl containing from 5-7 ring atoms, wherein from 1-2 of the ring atoms of the heterocyclyl is independently selected from N, NH, N($C_1$-$C_6$ alkyl), NC(O)($C_1$-$C_6$ alkyl), NC(O)O($C_1$-$C_6$ alkyl), O, and S; and each of which is optionally substituted with from 1-3 independently selected $C_1$-$C_4$ alkyl groups, such as an optionally substituted piperazinyl ring.

In certain of these formula I-A embodiments:
X' is S or NH;
X''' is Y;
X'' is H or $R^a$; $R^a$ is $C_1$-$C_8$ alkyl (e.g., $C_1$-$C_6$ alkyl, e.g., $C_1$-$C_3$ alkyl, e.g., $CH_3$); (e.g., X'' is H or $CH_3$; e.g., X'' is H);
Y is $C_6$-$C_{10}$ aryl, which is optionally substituted with from 1-5 independently selected R'' (e.g., Y is unsubstituted phenyl);
$R^2$ is heteroaryl containing from 5-6 (e.g., 5) ring atoms, wherein from 1-4 of the ring atoms is independently selected from N, NH, N($C_1$-$C_3$ alkyl), NC(O)($C_1$-$C_6$ alkyl), O, and S; and wherein said heteroaryl is optionally substituted with from 1-3 $R^e$, such as thienyl, furanyl, or thiazolyl; (e.g., each occurrence of $R^e$ is, independently, halo; cyano; —C(O)($C_1$-$C_6$ alkyl); C(O)OH; —C(O)O($C_1$-$C_6$ alkyl); nitro; —$NH_2$; —NH($C_1$-$C_6$ alkyl), N($C_1$-$C_6$ alkyl)$_2$, —NHC(O)($C_1$-$C_6$ alkyl), $C_1$-$C_6$ alkoxy; $C_1$-$C_6$ haloalkoxy; $C_1$-$C_6$ thioalkoxy; $C_1$-$C_6$ thiohaloalkoxy; $C_1$-$C_6$ alkyl, $C_3$-$C_6$ cycloalkyl; and $C_1$-$C_6$ haloalkyl; or e.g., $R^2$ is unsubstituted heteroaryl, such as unsubstituted thienyl, furanyl, or thiazolyl); and
$R^{12}$ is —C(O)OH (see, e.g., compound 165-87).

In some embodiments:
A is N;
X contains 2 ring atoms independently selected from N, NH, N($C_1$-$C_3$ alkyl), O, and S, and one of the ring atoms is independently selected from N, NH, and N($C_1$-$C_3$ alkyl), and the other ring atom is independently selected from N, NH, N($C_1$-$C_3$ alkyl), O, and S; and
$R^1$ is heteroaryl, which contains from 5-10 ring atoms, wherein from 1-4 of the ring atoms is independently selected from N, NH, N($C_1$-$C_3$ alkyl), O, and S; and wherein said heteroaryl ring is optionally substituted with from 1-3 independently selected $R^c$.

In some embodiments, the compound has formula I-B:

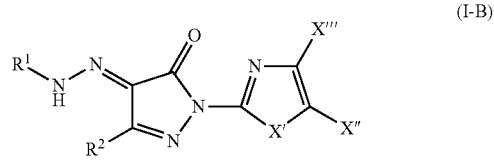

(I-B)

wherein:
X' is NH, O, or S; and
one of X'' and X''' is Y, and the other of X'' and X''' is H or $R^a$.

Embodiments in which the compound has formula I-B can include one or more of the following features.
X' is S, X''' is Y, and X'' is H or $R^a$ (e.g., X'' is H).
X' is NH, X''' is Y, and X'' is H or $R^a$ (e.g., X'' is H).
$R^1$ is thiazolyl.
Y is $C_6$-$C_{10}$ aryl, which is optionally substituted with from 1-5 independently selected $R^b$. $R^2$ is phenyl that is optionally substituted with from 1-4 $R^e$. $R^2$ is unsubstituted phenyl.

Compound Forms and Salts

In some embodiments, the compounds described herein may contain one or more asymmetric centers and thus occur as racemates and racemic mixtures, enantiomerically enriched mixtures, single enantiomers, individual diastereomers and diastereomeric mixtures (e.g., including (R)- and (S)-enantiomers, diastereomers, (D)-isomers, (L)-isomers, (+) (dextrorotatory) forms, (−) (levorotatory) forms, the racemic mixtures thereof, and other mixtures thereof). Additional asymmetric carbon atoms may be present in a substituent, such as an alkyl group. All such isomeric forms, as well as mixtures thereof, of these compounds are expressly included in the present invention. The compounds described herein may also or further contain linkages wherein bond rotation is restricted about that particular linkage, e.g. restriction resulting from the presence of a ring or double bond (e.g., carbon-carbon bonds, carbon-nitrogen bonds such as amide bonds). Accordingly, all cis/trans and E/Z isomers and rotational isomers are expressly included in the present invention. The compounds of this invention may also be represented in multiple tautomeric forms; in such instances, the invention expressly includes all tautomeric forms of the compounds described herein, even though only a single tautomeric form may be represented. All such isomeric forms of such compounds are expressly included in the present invention. Unless otherwise mentioned or indicated, the chemical designation of a compound encompasses the mixture of all possible stereochemically isomeric forms of that compound.

Optical isomers can be obtained in pure form by standard procedures known to those skilled in the art, and include, but are not limited to, diastereomeric salt formation, kinetic resolution, and asymmetric synthesis. See, for example, Jacques, et al., Enantiomers, Racemates and Resolutions (Wiley Interscience, New York, 1981); Wilen, S. H., et al., Tetrahedron 33:2725 (1977); Eliel, E. L. Stereochemistry of Carbon Compounds (McGraw-Hill, N Y, 1962); Wilen, S. H. Tables of Resolving Agents and Optical Resolutions p. 268 (E. L. Eliel, Ed., Univ. of Notre Dame Press, Notre Dame, Ind. 1972), each of which is incorporated herein by reference in their entireties. It is also understood that this invention encompasses all possible regioisomers, and mixtures thereof, which can be obtained in pure form by standard separation procedures known to those skilled in the art, and include, but are not limited to, column chromatography, thin-layer chromatography, and high-performance liquid chromatography.

The compounds of this invention include the compounds themselves, as well as their salts and their prodrugs, if applicable. A salt, for example, can be formed between an anion and a positively charged substituent (e.g., amino) on a compound described herein. Suitable anions include chloride, bromide, iodide, sulfate, nitrate, phosphate, citrate, methanesulfonate, trifluoroacetate, and acetate. Likewise, a salt can also be formed between a cation and a negatively charged substituent (e.g., carboxylate) on a compound described herein. Suitable cations include sodium ion, potassium ion, magnesium ion, calcium ion, and an ammonium cation such as tetramethylammonium ion. Examples of prodrugs include $C_{1-6}$ alkyl esters of carboxylic acid groups, which, upon administration to a subject, are capable of providing active compounds.

Pharmaceutically acceptable salts of the compounds of this invention include those derived from pharmaceutically acceptable inorganic and organic acids and bases. As used herein, the term "pharmaceutically acceptable salt" refers to a salt formed by the addition of a pharmaceutically acceptable acid or base to a compound disclosed herein. As used herein, the phrase "pharmaceutically acceptable" refers to a substance that is acceptable for use in pharmaceutical applications from a toxicological perspective and does not adversely interact with the active ingredient.

Examples of suitable acid salts include acetate, adipate, alginate, aspartate, benzoate, benzenesulfonate, bisulfate, butyrate, citrate, camphorate, camphorsulfonate, digluconate, dodecyl sulfate, ethanesulfonate, formate, fumarate, glucoheptanoate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization. Salt forms of the compounds of any of the formulae herein can be amino acid salts of carboxy groups (e.g. L-arginine, -lysine, -histidine salts).

Lists of suitable salts are found in Remington's Pharmaceutical Sciences, 17th ed., Mack Publishing Company, Easton, Pa., 1985, p. 1418; Journal of Pharmaceutical Science, 66, 2 (1977); "Pharmaceutical Salts: Properties, Selection, and Use A Handbook; Wermuth, C. G. and Stahl, P. H. (eds.) Verlag Helvetica Chimica Acta, Zurich, 2002 [ISBN 3-906390-26-8]; and Berge et al. (1977) "Pharmaceutical Salts", J. Pharm. Sci. 66:1-19; each of which is incorporated herein by reference in its entirety.

The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the invention.

In addition to salt forms, the invention provides compounds which are in a prodrug form. Prodrugs of the compounds described herein are those compounds that undergo chemical changes under physiological conditions to provide the compounds of the invention. Additionally, prodrugs can be converted to the compounds of the invention by chemical or biochemical methods in an ex vivo environment. For example, prodrugs can be slowly converted to the compounds of the invention when placed in a transdermal patch reservoir with a suitable enzyme or chemical reagent. Prodrugs are often useful because, in some situations, they may be easier to administer than the parent drug. They may, for instance, be more bioavailable by oral administration than the parent drug. The prodrug may also have improved solubility in pharmacological compositions over the parent drug. A wide variety of prodrug derivatives are known in the art, such as those that rely on hydrolytic cleavage or oxidative activation of the prodrug. An example, without limitation, of a prodrug would be a compound of the invention which is administered as an ester (the "prodrug"), but then is metabolically hydrolyzed to the carboxylic acid, the active entity. In embodiments, the ester can be an alkyl ester (e.g., $C_1$-$C_3$ alkyl, e.g., $CH_3$ or $CH_2CH_3$; or $C_3$-$C_6$ alkyl, e.g., $C_3$-$C_6$ branched alkyl, e.g., t-butyl, isopropyl, isobutyl). Additional examples include peptidyl derivatives of a compound of the invention.

The invention also includes various hydrate and solvate forms of the compounds (and salts thereof) described herein.

The compounds of the invention may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the invention, whether radioactive or not, are intended to be encompassed within the scope of the invention.

Synthesis of Compounds

The compounds described herein can be conveniently prepared in accordance with the procedures outlined herein, from commercially available starting materials, compounds known in the literature, or readily prepared intermediates, by employing standard synthetic methods and procedures known to those skilled in the art. Standard synthetic methods and procedures for the preparation of organic molecules and functional group transformations and manipulations can be readily obtained from the relevant scientific literature or from standard textbooks in the field. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvents used, but such conditions can be determined by one skilled in the art by routine optimization procedures. Those skilled in the art of organic synthesis will recognize that the nature and order of the synthetic steps presented may be varied for the purpose of optimizing the formation of the compounds described herein.

Synthetic chemistry transformations (including protecting group methodologies) useful in synthesizing the compounds described herein are known in the art and include, for example, those such as described in R. C. Larock, *Comprehensive Organic Transformations,* 2d. ed., Wiley-VCH Publishers (1999); P. G. M. Wuts and T. W. Greene, *Protective Groups in Organic Synthesis,* 4th Ed., John Wiley and Sons (2007); L. Fieser and M. Fieser, *Fieser and Fieser's Reagents for Organic Synthesis,* John Wiley and Sons (1994); and L. Paquette, ed., *Encyclopedia of Reagents for Organic Synthesis,* John Wiley and Sons (1995), and subsequent editions thereof.

The processes described herein can be monitored according to any suitable method known in the art. For example, product formation can be monitored by spectroscopic means, such as nuclear magnetic resonance spectroscopy (e.g., $^1$H or $^{13}$C), infrared spectroscopy (FT-IR), spectrophotometry (e.g., UV-visible), or mass spectrometry (MS), or by chromatography such as high performance liquid chromatograpy (HPLC) or thin layer chromatography (TLC).

Preparation of compounds can involve the protection and deprotection of various chemical groups. The need for protection and deprotection, and the selection of appropriate protecting groups can be readily determined by one skilled in the art. The chemistry of protecting groups can be found, for example, in Greene, et al., *Protective Groups in Organic Synthesis,* 2d. Ed., Wiley & Sons, 1991, which is incorporated herein by reference in its entirety.

The reactions of the processes described herein can be carried out in suitable solvents which can be readily selected by one of skill in the art of organic synthesis. Suitable solvents can be substantially nonreactive with the starting materials (reactants), the intermediates, or products at the temperatures at which the reactions are carried out, i.e., temperatures which can range from the solvent's freezing temperature to the solvent's boiling temperature. A given reaction can be carried out in one solvent or a mixture of solvents. Depending on the particular reaction step, suitable solvents for a particular reaction step can be selected.

Figure 1A:
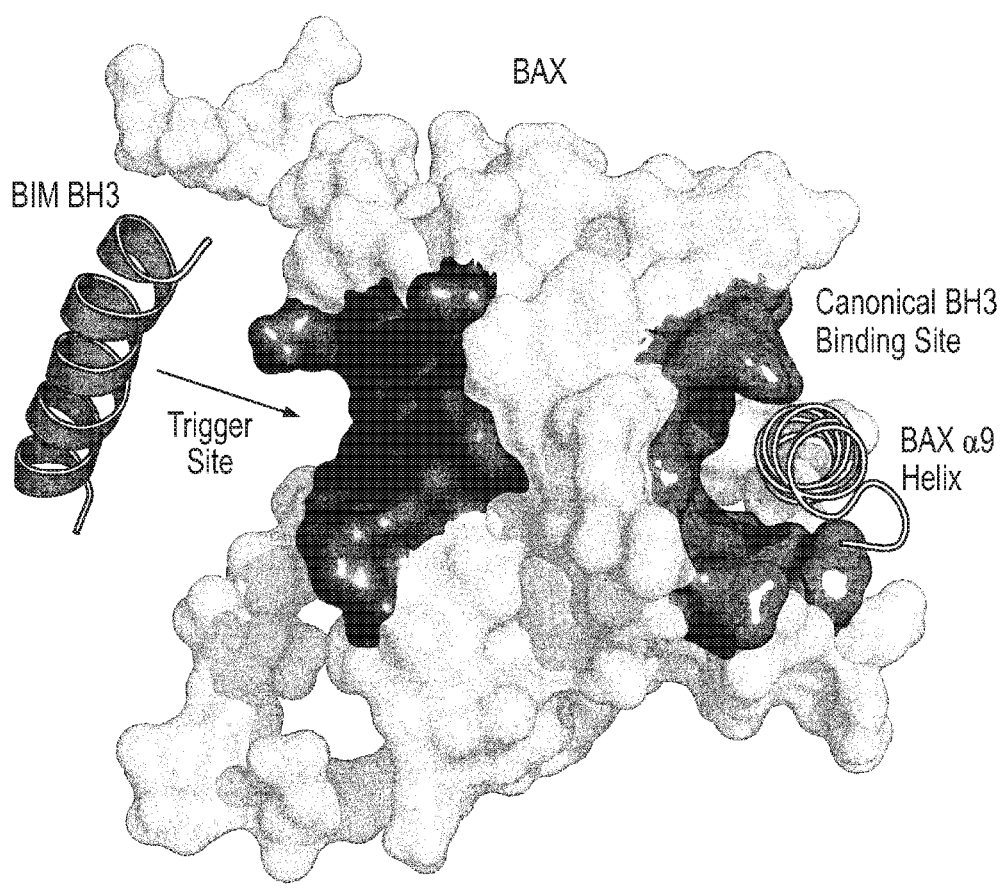
FIG. 1A is a structural depiction of BAX, which shows that the BIM BH3 trigger site on pro-apoptotic BAX (left hand side of structural depiction) localizes to the N-terminal face of the protein. In contrast, the canonical BH3 binding pocket of anti-apoptotic proteins (right hand side of structural depiction) maps to the opposite side of BAX and remains occupied by the C-terminal helix 9 (yellow) when the protein is in the inactive, monomeric state.
Figure 1B:
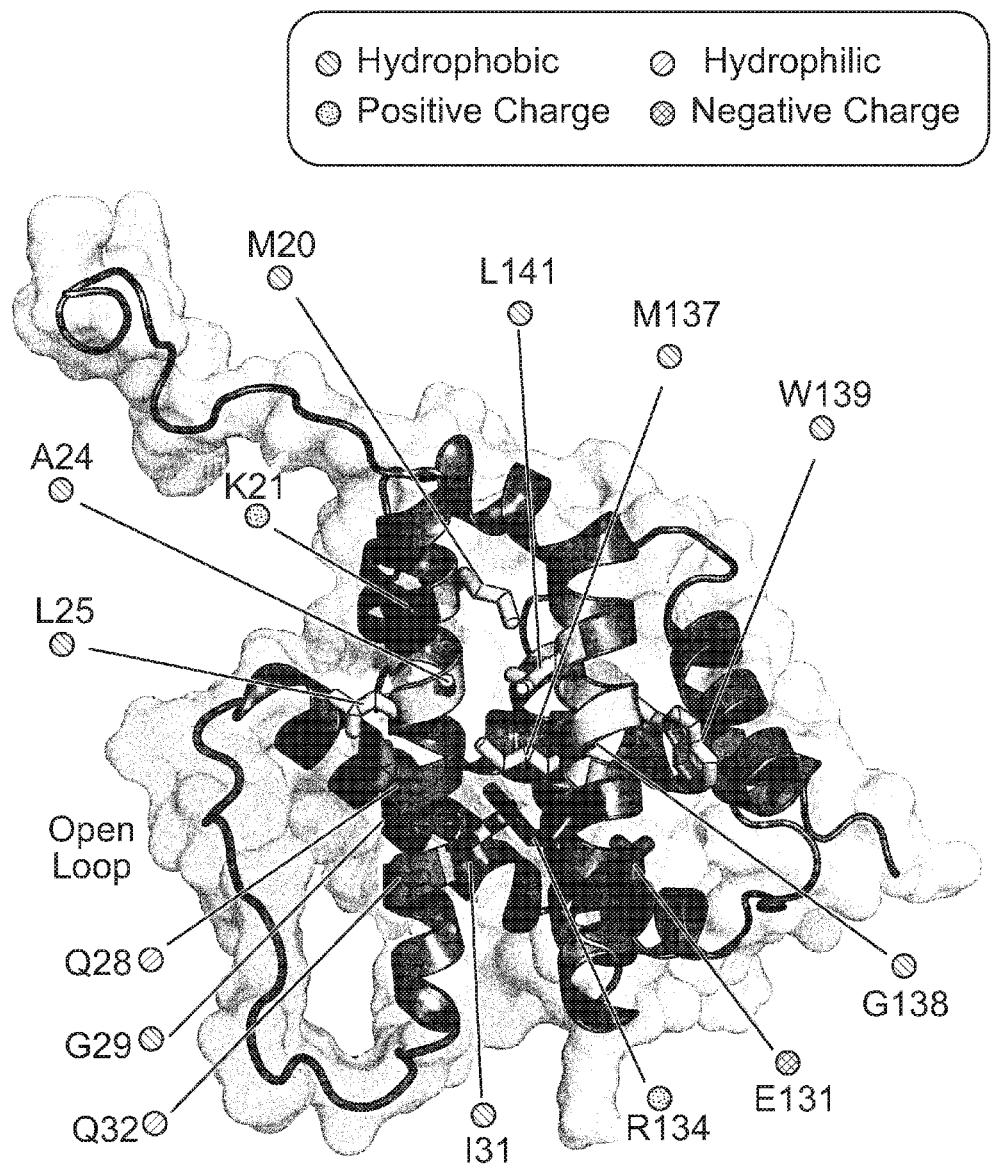
FIG. 1B is a structural depiction of BAX, which shows that the BH3 trigger site is comprised of a hydrophobic groove with a perimeter of charged and hydrophilic residues from α-helices 1 and 6. BAX is oriented to demonstrate its N-terminal face and the individual amino acids that comprise the trigger site, with the unstructured loop between α 1 and α 2 depicted in the open position.
Figure 2A:
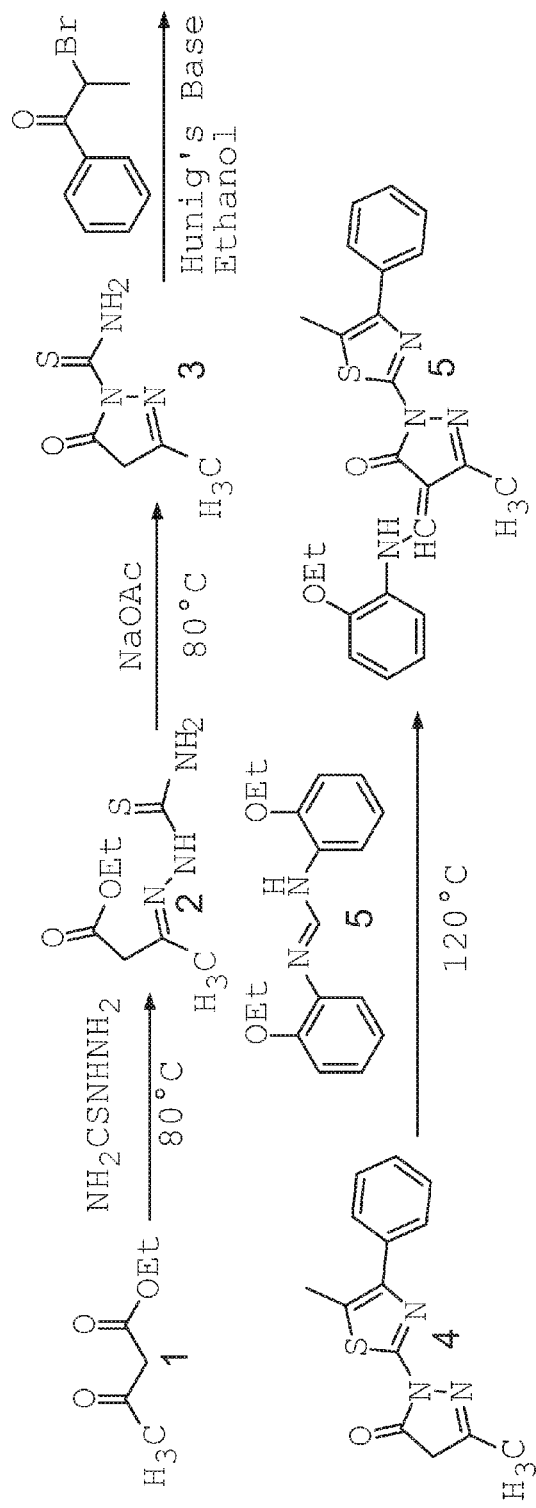
FIGS. 2A-2I are reaction schemes showing the syntheses used to prepare a variety of compounds of formula (I).
Figure 2B:
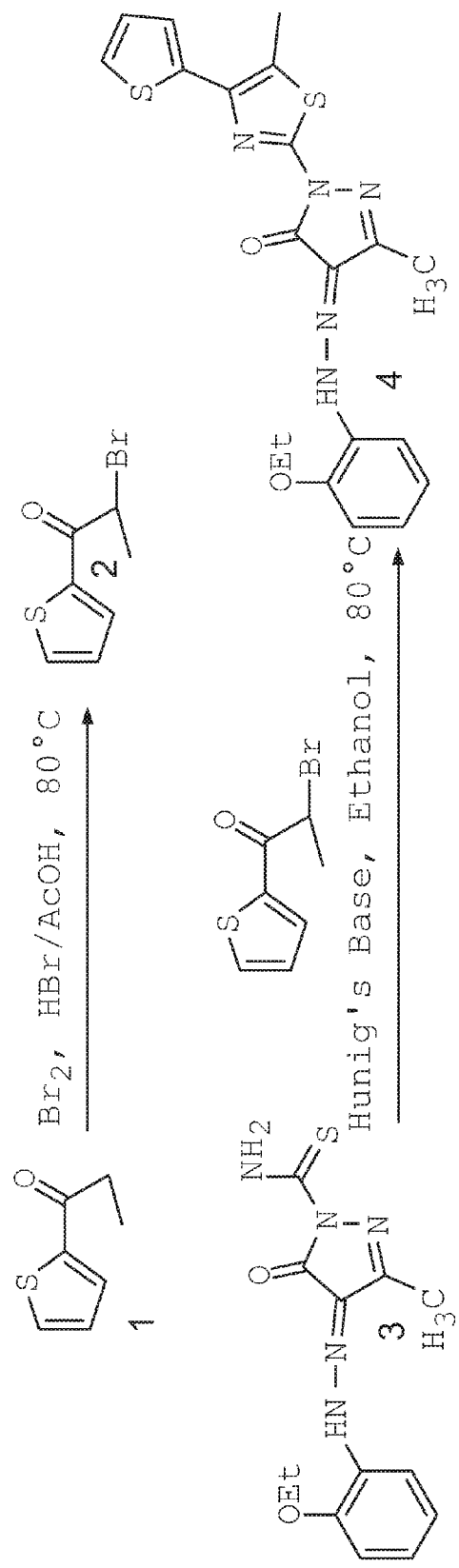
Figure 2C:
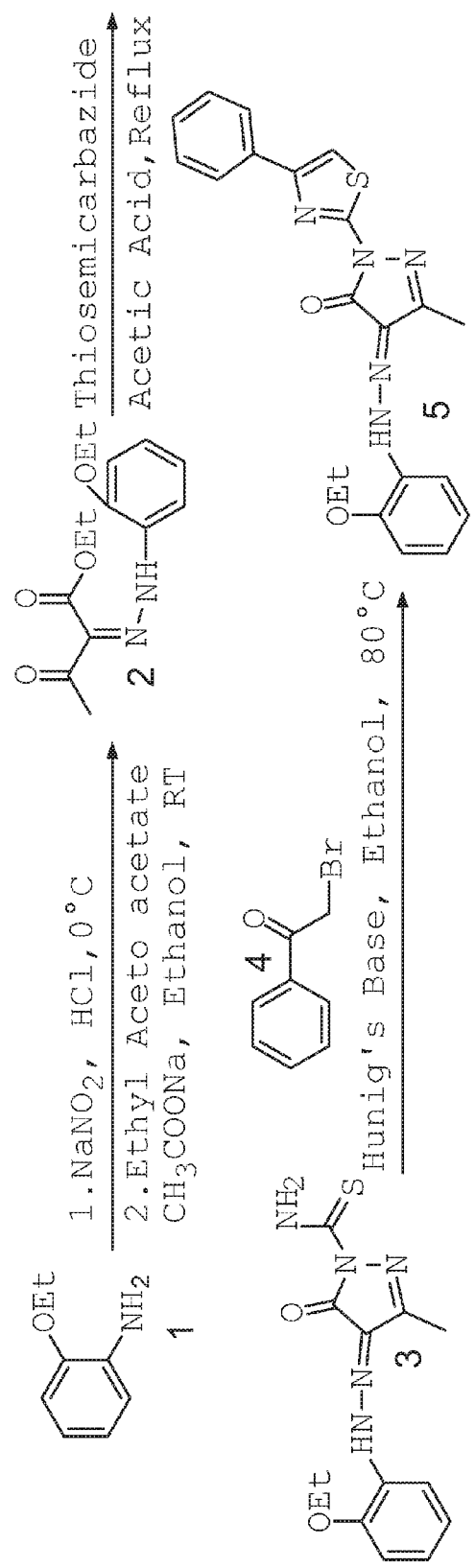
Figure 2D:
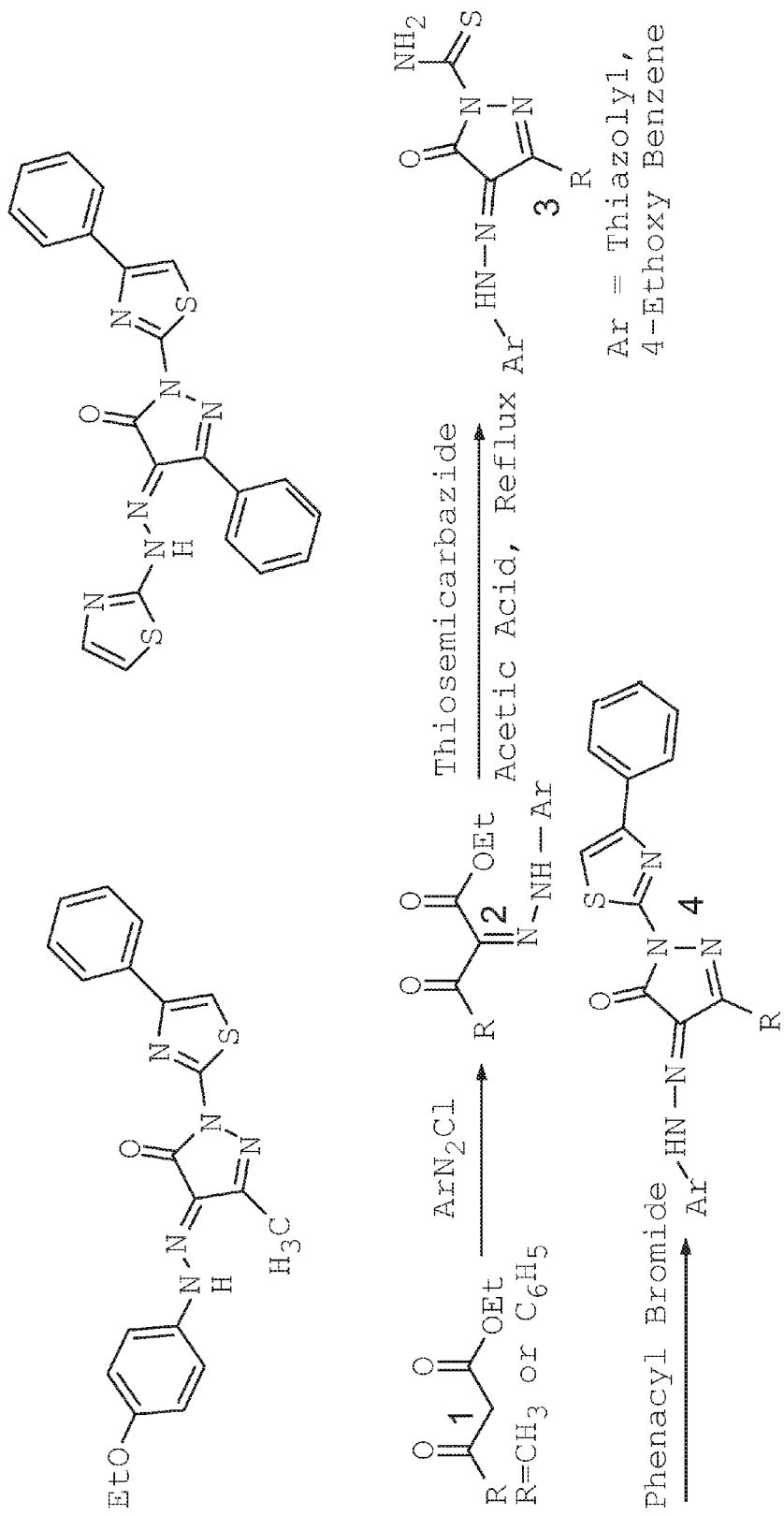
Figure 2E:
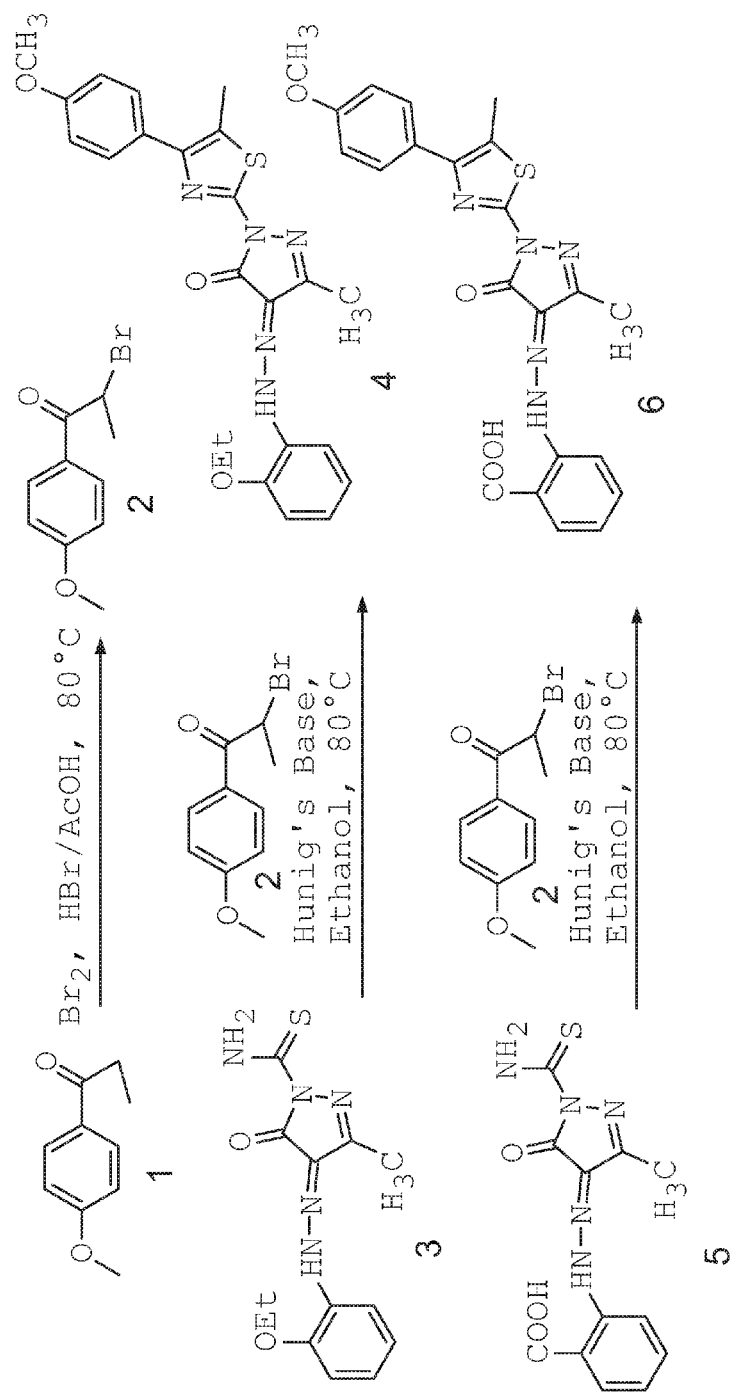
Figure 2F:
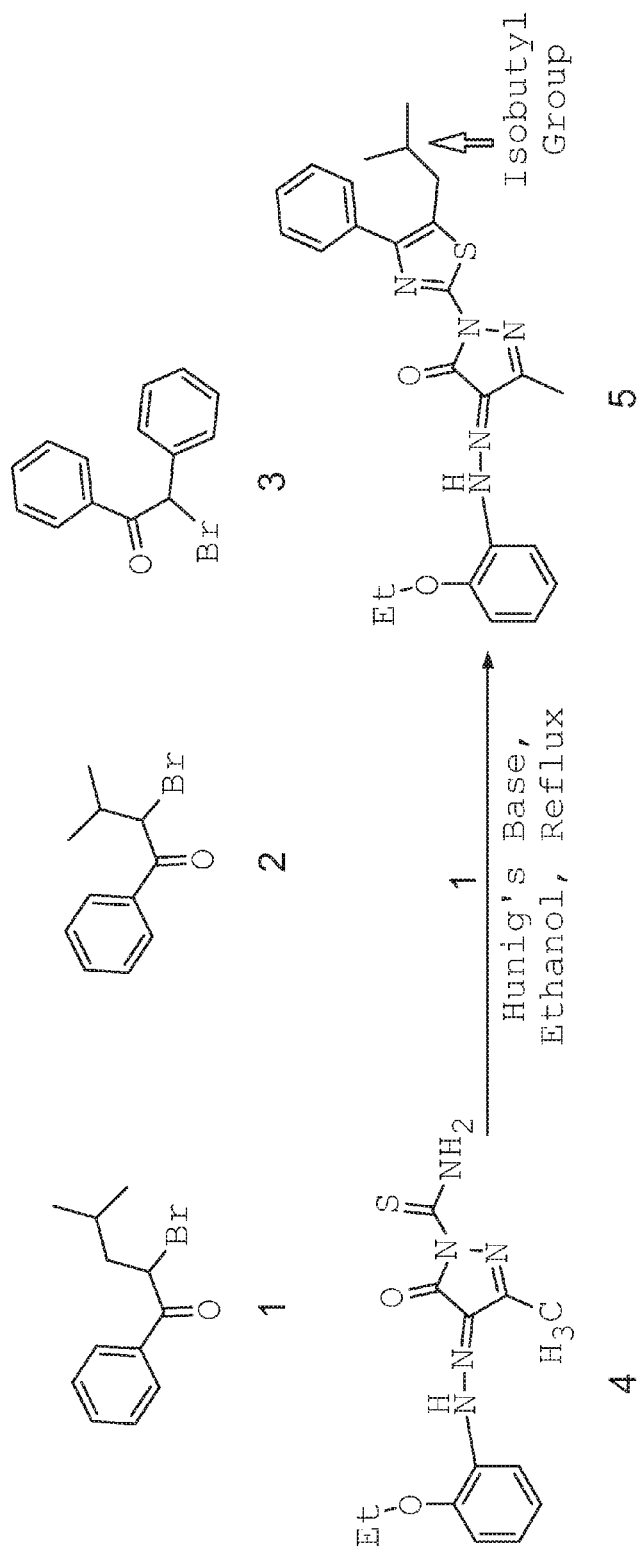
Figure 2G:
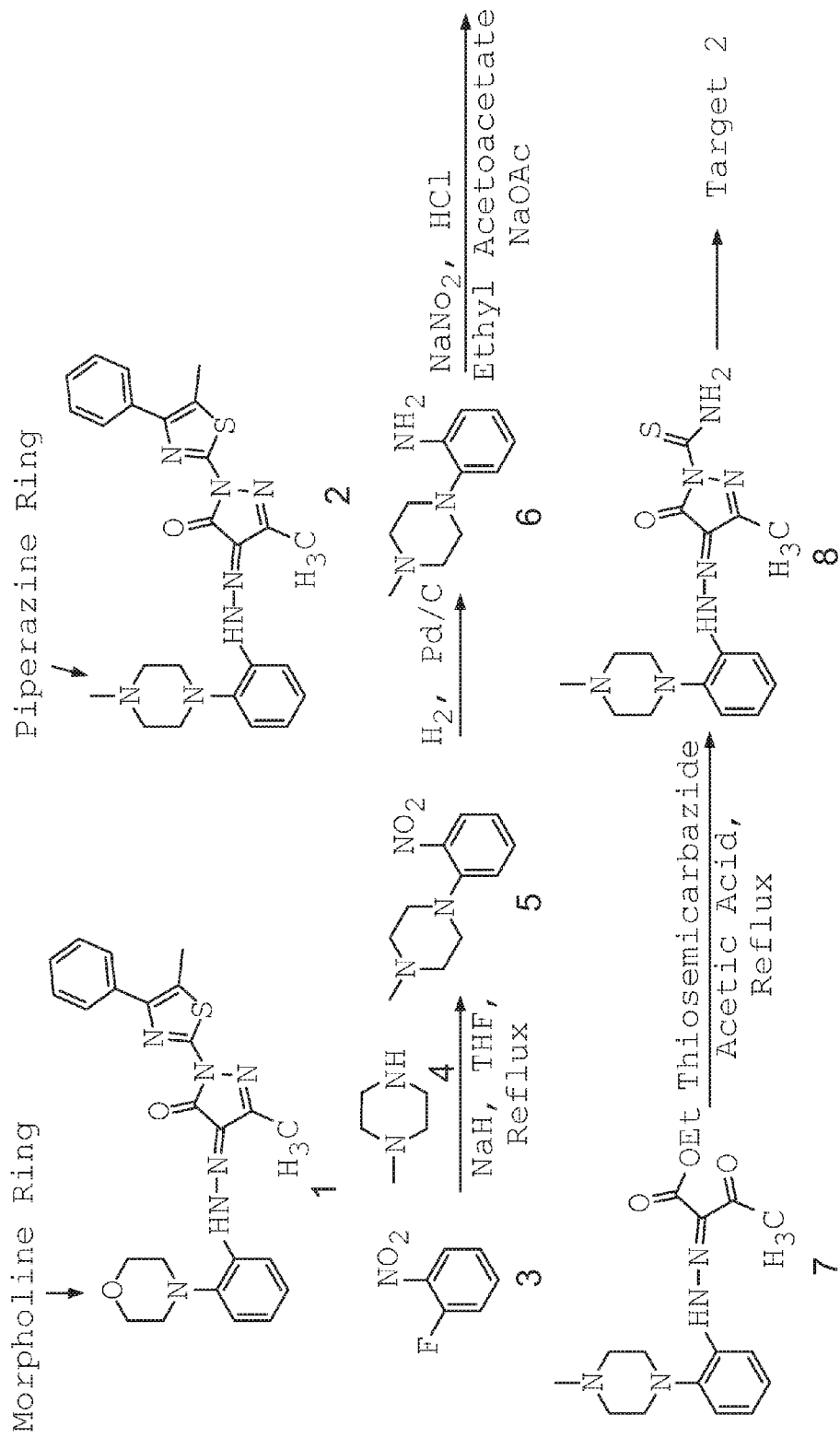
Figure 2H:
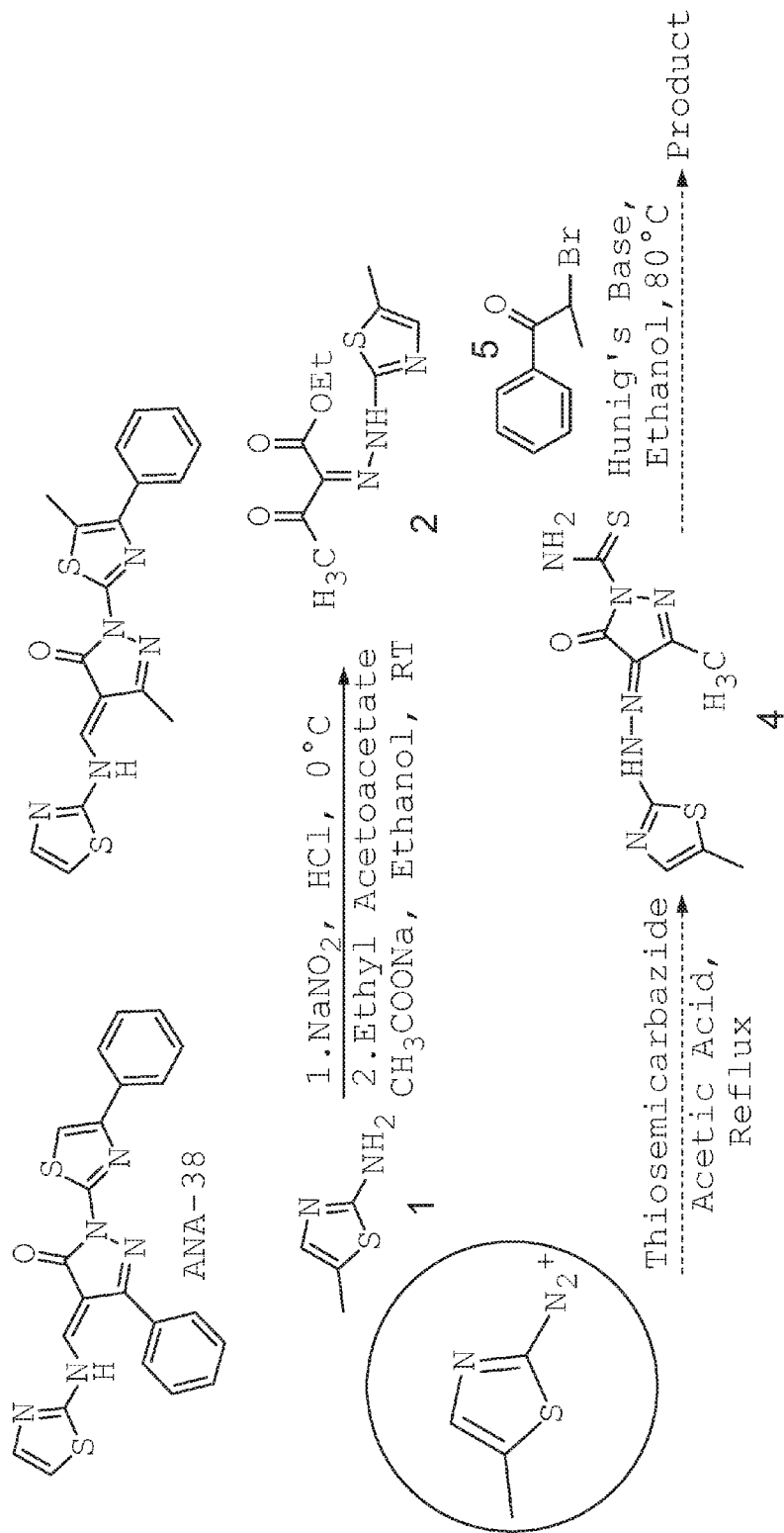
Figure 2I:
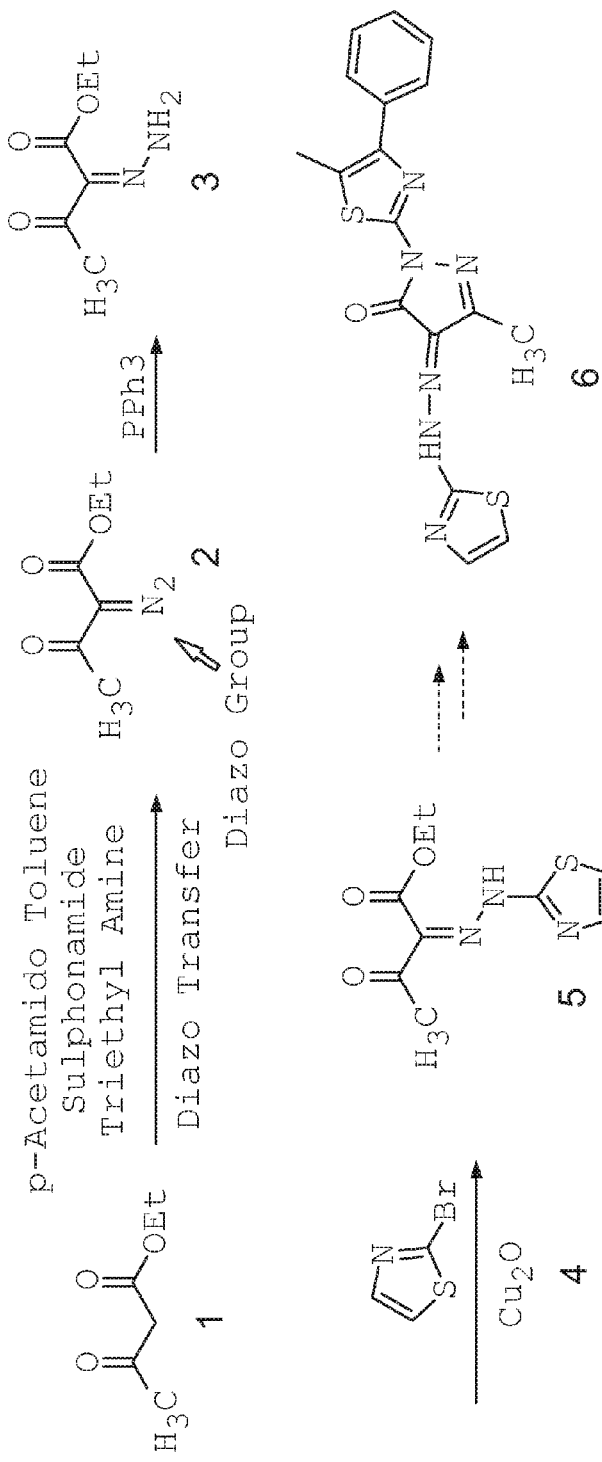

In some embodiments, the formula (I) compounds can be prepared using the reaction pathways and techniques as shown in FIGS. 2A-2I and 19A-19F. In FIG. 2B, compounds 161-87 and 153-96 can be prepared using this route using the corresponding thiazolyl and phenyl substituted reagents.

Pharmaceutical Compositions

The term "pharmaceutically acceptable carrier" refers to a carrier or adjuvant that may be administered to a subject (e.g., a patient), together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the compositions of this invention include, but are not limited to, ion exchangers, alumina, aluminum stearate, lecithin, self-emulsifying drug delivery systems (SEDDS) such as d-α-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts, or electrolytes, such as protamine sulfate, disodium hydrogen phosphate, potassium hydrogen phosphate, sodium chloride, zinc salts, colloidal silica, magnesium tri silicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as α-, β-, and γ-cyclodextrin, or chemically modified derivatives such as hydroxyalkylcyclodextrins, including 2- and 3-hydroxypropyl-β-cyclodextrins, or other solubilized derivatives may also be advantageously used to enhance delivery of compounds of the formulae described herein.

The compositions for administration can take the form of bulk liquid solutions or suspensions, or bulk powders. More commonly, however, the compositions are presented in unit dosage forms to facilitate accurate dosing. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient. Typical unit dosage forms include prefilled, premeasured ampules or syringes of the liquid compositions or pills, tablets, capsules, losenges or the like in the case of solid compositions. In such compositions, the compound is usually a minor component (from about 0.1 to about 50% by weight or preferably from about 1 to about 40% by weight) with the remainder being various vehicles or carriers and processing aids helpful for forming the desired dosing form.

The amount administered depends on the compound formulation, route of administration, etc. and is generally empirically determined in routine trials, and variations will necessarily occur depending on the target, the host, and the route of administration, etc. Generally, the quantity of active compound in a unit dose of preparation may be varied or adjusted from about 1, 3, 10 or 30 to about 30, 100, 300 or 1000 mg, according to the particular application. In a particular embodiment, unit dosage forms are packaged in a multipack adapted for sequential use, such as blisterpack, comprising sheets of at least 6, 9 or 12 unit dosage forms. The actual dosage employed may be varied depending upon the requirements of the patient and the severity of the condition being treated. Determination of the proper dosage for a particular situation is within the skill of the art. Generally, treatment is initiated with smaller dosages which are less than the optimum dose of the compound. Thereafter, the dosage is increased by small amounts until the optimum effect under the circumstances is reached. For convenience, the total daily dosage may be divided and administered in portions during the day if desired.

Use and Administration

This application features pyrazol-3-one compounds that activate pro-apoptotic BAX, making them therapeutically useful for treating (e.g., controlling, relieving, ameliorating, alleviating, or slowing the progression of) or preventing (e.g., delaying the onset of or reducing the risk of developing) diseases, disorders, and conditions associated with deregulated apoptosis of (e.g., diseased or damaged cells; e.g., insufficient apoptosis of diseased or damaged cells; or lack of or reduced apoptosis of diseased or damaged cells). Examples of such diseases, disorders, and conditions include (but are not limited to) those associated with blockade(s) of cell death pathways (e.g., over-expression of anti-apoptotic BCL-2 proteins), e.g., hyperproliferative diseases, such as cancer. While not wishing to be bound by theory, it is believed that the compounds described herein induce and increase apoptosis in target cells (e.g., pathogenic cells including, but not limited to, cancer cells), thereby suppressing tumor growth and/or proliferation. It is further believed that increasing apoptosis in said target cells reestablishes the normal apoptotic control that, during homeostasis, is associated with a regulated balance between pro- and anti-apoptotic protein functions.

The compounds and compositions described herein can, for example, be administered orally, parenterally (e.g., subcutaneously, intracutaneously, intravenously, intramuscularly, intraarticularly, intraarterially, intrasynovially, intrasternally, intrathecally, intralesionally and by intracranial injection or infusion techniques), by inhalation spray, topically, rectally, nasally, buccally, vaginally, via an implanted reservoir, by injection, subdermally, intraperitoneally, transmucosally, or in an ophthalmic preparation, with a dosage ranging from about 0.01 mg/kg to about 1000 mg/kg, (e.g., from about 0.01 to about 100 mg/kg, from about 0.1 to about 100 mg/kg, from about 1 to about 100 mg/kg, from about 1 to about 10 mg/kg) every 4 to 120 hours, or according to the requirements of the particular drug. The interrelationship of dosages for animals and humans (based on milligrams per meter squared of body surface) is described by Freireich et al., Cancer Chemother. Rep. 50, 219 (1966). Body surface area may be approximately determined from height and weight of the patient. See, e.g., Scientific Tables, Geigy Pharmaceuticals, Ardsley, N.Y., 537 (1970). In certain embodiments, the compositions are administered by oral administration or administration by injection. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

In some embodiments, the compounds described herein can be coadministered with one or more other therapeutic agents. In certain embodiments, the additional agents may be administered separately, as part of a multiple dose regimen, from the compounds of this invention (e.g., sequentially, e.g., on different overlapping schedules with the administration of one or more compounds of formula (I) (including any subgenera or specific compounds thereof)). In other embodiments, these agents may be part of a single dosage form, mixed together with the compounds of this invention in a single composition. In still another embodiment, these agents can be given as a separate dose that is administered at about the same time that one or more compounds of formula (I) (including any subgenera or specific compounds thereof) are administered (e.g., simultaneously with the administration of one or more compounds of formula (I) (including any subgenera or specific compounds thereof)). When the compositions of this invention include a combination of a compound of the formulae described herein and one or more additional therapeutic or prophylactic agents, both the compound and the additional agent can be present at dosage levels of between about 1 to 100%, and more preferably between about 5 to 95% of the dosage normally administered in a monotherapy regimen.

The compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form.

The compositions may be in the form of a sterile injectable preparation, for example, as a sterile injectable aqueous or oleaginous suspension. This suspension may be formulated according to techniques known in the art using suitable dispersing or wetting agents (such as, for example, Tween 80) and suspending agents. The sterile injectable preparation may also be a sterile injectable solution or suspension in a non-toxic parenterally acceptable diluent or solvent, for example, as a solution in 1,3-butanediol. Among the acceptable vehicles and solvents that may be employed are mannitol, water, Ringer's solution and isotonic sodium chloride solution. In addition, sterile, fixed oils are conventionally employed as a solvent or suspending medium. For this purpose, any bland fixed oil may be employed including synthetic mono- or diglycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions. Other commonly used surfactants such as Tweens or Spans and/or other similar emulsifying agents or bioavailability enhancers which are commonly used in the manufacture of pharmaceutically acceptable solid, liquid, or other dosage forms may also be used for the purposes of formulation.

The compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the compositions of this invention is useful when the desired treatment involves areas or organs readily accessible by topical application. For application topically to the skin, the composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The compositions of this invention may also be topically applied to the lower intestinal tract by rectal suppository formulation or in a suitable enema formulation.

In some embodiments, topical administration of the compounds and compositions described herein may be presented in the form of an aerosol, a semi-solid pharmaceutical composition, a powder, or a solution. By the term "a semi-solid composition" is meant an ointment, cream, salve, jelly, or other pharmaceutical composition of substantially similar consistency suitable for application to the skin. Examples of semi-solid compositions are given in Chapter 17 of The Theory and Practice of Industrial Pharmacy, Lachman, Lieberman and Kanig, published by Lea and Febiger (1970) and in Remington's Pharmaceutical Sciences, 21st Edition (2005) published by Mack Publishing Company, which is incorporated herein by reference in its entirety.

Topically-transdermal patches are also included in this invention. Also within the invention is a patch to deliver active chemotherapeutic combinations herein. A patch includes a material layer (e.g., polymeric, cloth, gauze, bandage) and the compound of the formulae herein as delineated herein. One side of the material layer can have a protective layer adhered to it to resist passage of the compounds or compositions. The patch can additionally include an adhesive to hold the patch in place on a subject. An adhesive is a composition, including those of either natural or synthetic origin, that when contacted with the skin of a subject, temporarily adheres to the skin. It can be water resistant. The adhesive can be placed on the patch to hold it in contact with the skin of the subject for an extended period of time. The adhesive can be made of a tackiness, or adhesive strength, such that it holds the device in place subject to incidental contact, however, upon an affirmative act (e.g., ripping, peeling, or other intentional removal) the adhesive gives way to the external pressure placed on the device or the adhesive itself, and allows for breaking of the adhesion contact. The adhesive can be pressure sensitive, that is, it can allow for positioning of the adhesive (and the device to be adhered to the skin) against the skin by the application of pressure (e.g., pushing, rubbing,) on the adhesive or device.

The compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A composition having the compound of the formulae herein and an additional agent (e.g., a therapeutic agent) can be administered using any of the routes of administration described herein. In some embodiments, a composition having the compound of the formulae herein and an additional agent (e.g., a therapeutic agent) can be administered using an implantable device. Implantable devices and related technology are known in the art and are useful as delivery systems where a continuous, or timed-release delivery of compounds or compositions delineated herein is desired. Additionally, the implantable device delivery system is useful for targeting specific points of compound or composition delivery (e.g., localized sites, organs). Negrin et al., Biomaterials, 22(6):563 (2001). Timed-release technology involving alternate delivery methods can also be used in this invention. For example, timed-release formulations based on polymer technologies, sustained-release techniques and encapsulation techniques (e.g., polymeric, liposomal) can also be used for delivery of the compounds and compositions delineated herein.

EXAMPLES

The invention will be further described in the following examples. It should be understood that these examples are for illustrative purposes only and are not to be construed as limiting this invention in any manner.

Example 1. Identification of Small Molecules that Bind the BAX Trigger Site

Figure 3A:
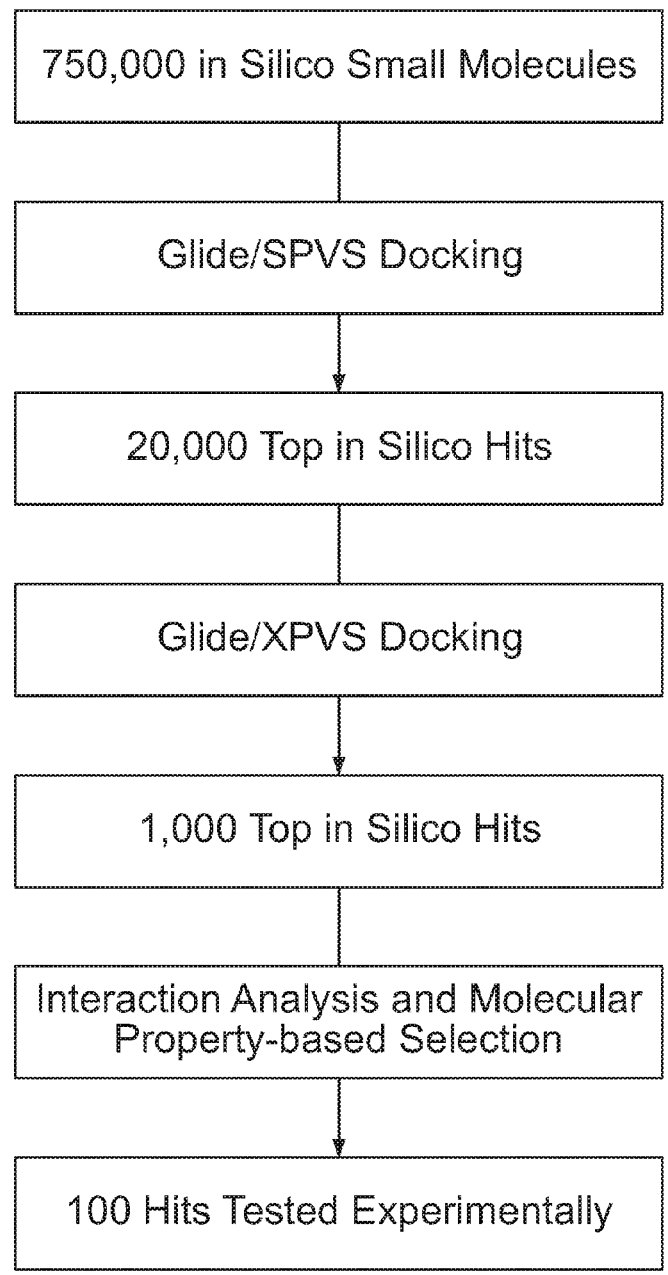
FIG. 3A is a flow diagram showing the results of a computational screening algorithm employing an in silico library of 750,000 small molecules docked on averaged minimized BAX structures. This screening yielded a panel of 100 candidate BAX activator molecules (BAMs).
Figure 3B:
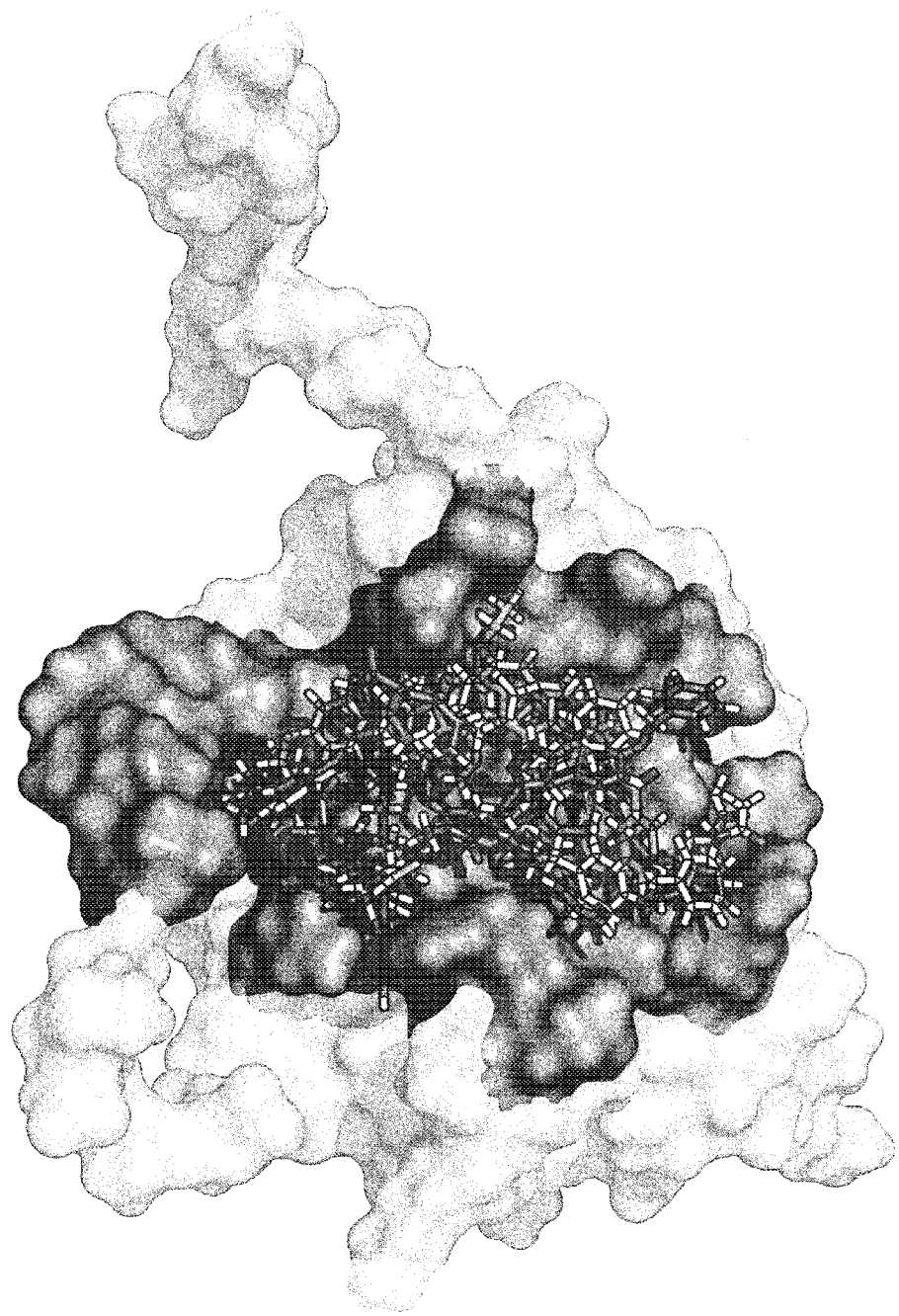
FIG. 3B is a compilation of the docked structures and demonstrates how candidate BAMs occupy the topographic landscape of the BAX trigger site.

We generated a diverse in silico compilation of 750,000 small molecules from commercially available libraries and docked the database of 3-dimensional molecules on average minimized BAX structures using Glide 4.0[19,20] in standard precision mode (SPVS) (FIG. 3A). The top-ranked 20,000 hits based on the Glidescore function for each BAX structural model were selected and re-docked to the BAX structures using extra precision docking mode (XPVS). The top 1,000 hits from each docking calculation were visualized with the Glide pose viewer and analyzed for their interactions with key BAX binding site residues. A subset of 100 molecules was selected for experimental analysis based on the presence of favorable hydrogen bonds, hydrophobic contacts, and molecular properties. Docking this compilation of putative BAX activator molecules (BAMs) demonstrates how the compounds blanket the surface of the BAX trigger site (FIG. 3B).

Figure 4D:
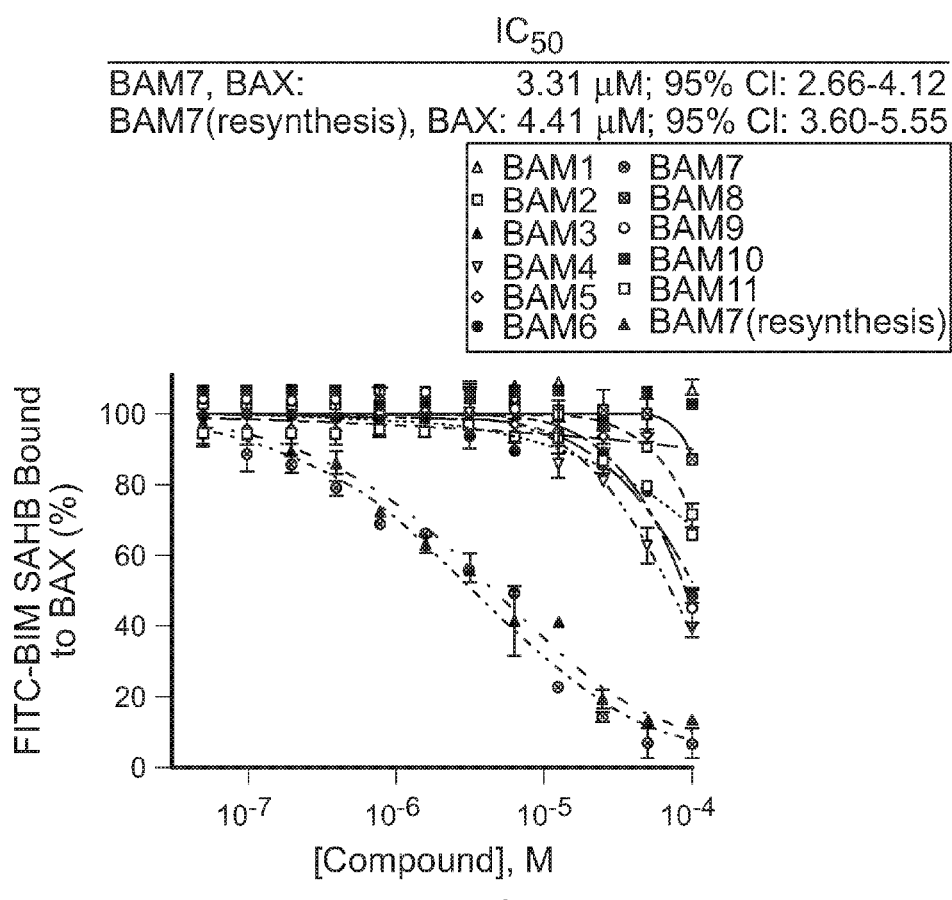
FIG. 4D is a graph that shows that a compound sometimes referred to herein as BAM7 emerged as the most effective of the tested small molecule competitors, displaying an $IC_{50}$ of 3.3 µM. Data are mean and s.d. for experiments performed in at least triplicate.
Figure 4E:
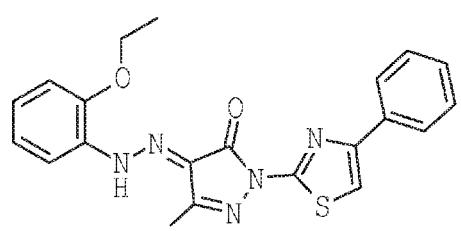
FIG. 4E shows the chemical structure of BAM7, which was confirmed by NMR and mass spectrometry, synthesized de novo, and found to have a similar $IC_{50}$ (4.4 µM) upon retesting by competitive FPA.
Figure 4F:
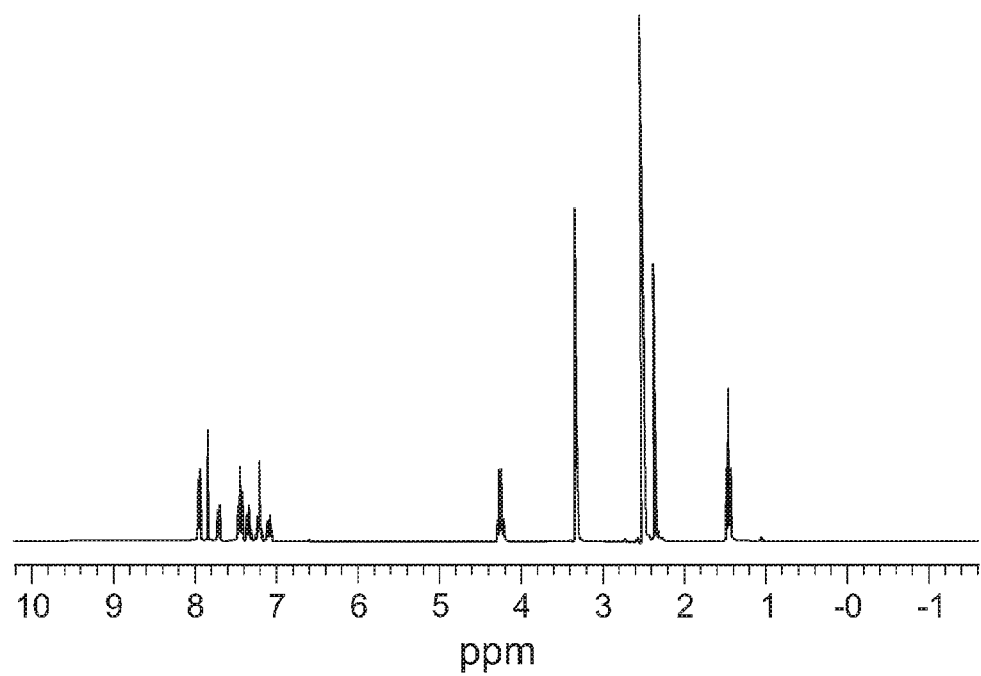
FIG. 4F shows the $^1$H-NMR spectrum of BAM7.

To evaluate the capacity of candidate BAMs to bind BAX, we developed a screening competitive fluorescence polarization assay (FPA) based on the interaction between recombinant BAX and the fluoresceinated Stabilized Alpha-Helix of BCL-2 domain (SAHB) modeled after BIM BH3 ($EC_{50}$, 283 nM) (FIG. 4A). Small molecules were then benchmarked against the displacement of FITC-BTM SAHB by N-terminal acetylated BIM SAH ($IC_{50}$, 314 nM) (FIG. 4B). Of the 78 molecules that lacked auto-fluorescence, 11 molecules achieved >55% displacement of FITC-BIM SAHB at the 100 µM screening dose (FIG. 4C). The ability of BAMs 1-11 to dose-responsively compete with FITC-BIM SAHB for BAX binding was then examined by FPA. BAM7 emerged as the most effective competitor, achieving an $IC_{50}$ of 3.3 µM, which compared favorably with unlabeled BIM SAHB considering that the molecule is only one-sixth the size of the BIM BH3 α-helical peptide (FIG. 4D). We verified the identity of BAM7 by NMR, resynthesized it, and documented a similar $IC_{50}$ value for competition with FITC-BIM SAHB (FIG. 4D). The chemical structure of BAM7 (MW 405.5) is shown in FIG. 4E and its $^1$H-NMR spectra shown in FIG. 4F.

Example 2. BAM7 is Selective for the BH3-Binding Site on BAX

Figure 5A:
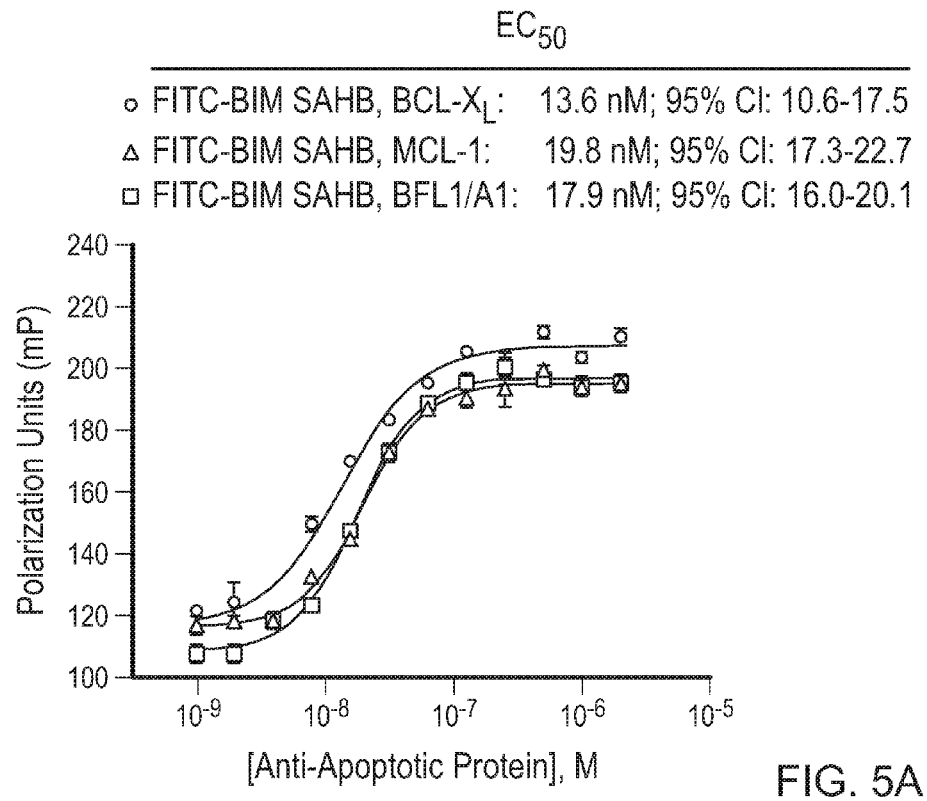
FIG. 5A is a graph showing that in addition to engaging BAX, FITC-BIM SAHB binds to the broad range of anti-apoptotic targets.
Figure 5B:
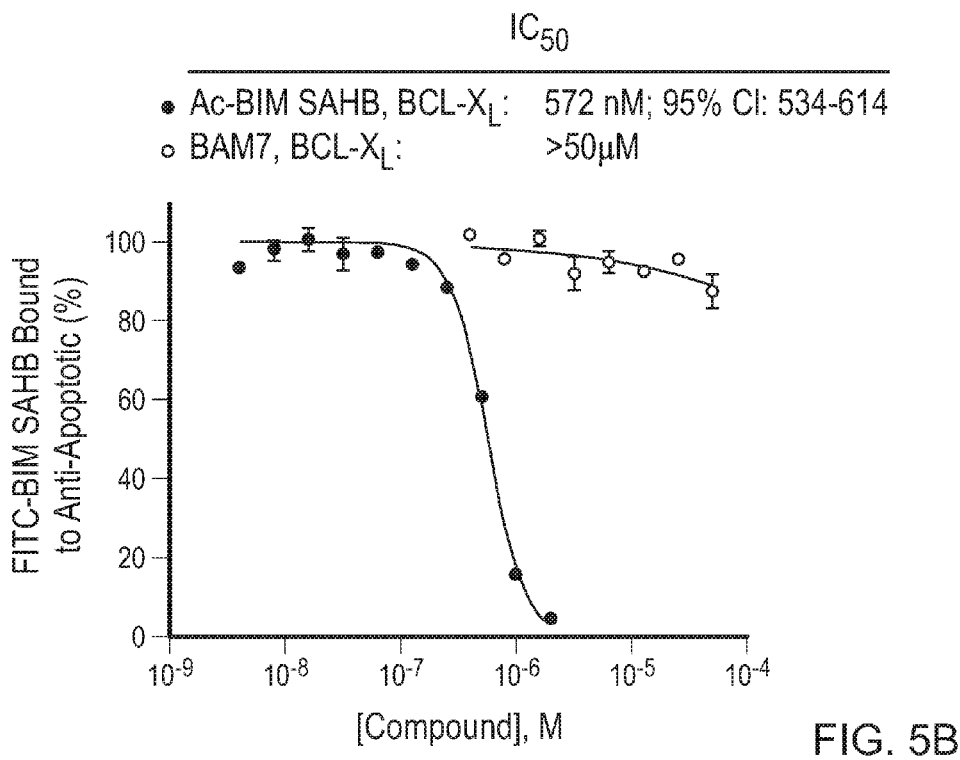
FIGS. 5B-5D are graphs summarizing the following data. The specificity of BAM7 for the BH3 binding site on BAX was examined by competitive FPA employing FITC-BIM SAHB and anti-apoptotic BCL-XL, MCL-1, and BFL-1/A1. Whereas Ac-BIM SAHB effectively competed with FITC-BIM SAHB for binding to a diversity of anti-apoptotic targets, BAM7 demonstrated little to no capacity to compete with FITC-BIM SAHB for interaction at the BH3 binding sites of anti-apoptotic proteins. Data are mean and s.d. for experiments performed in at least triplicate.
Figure 5C:
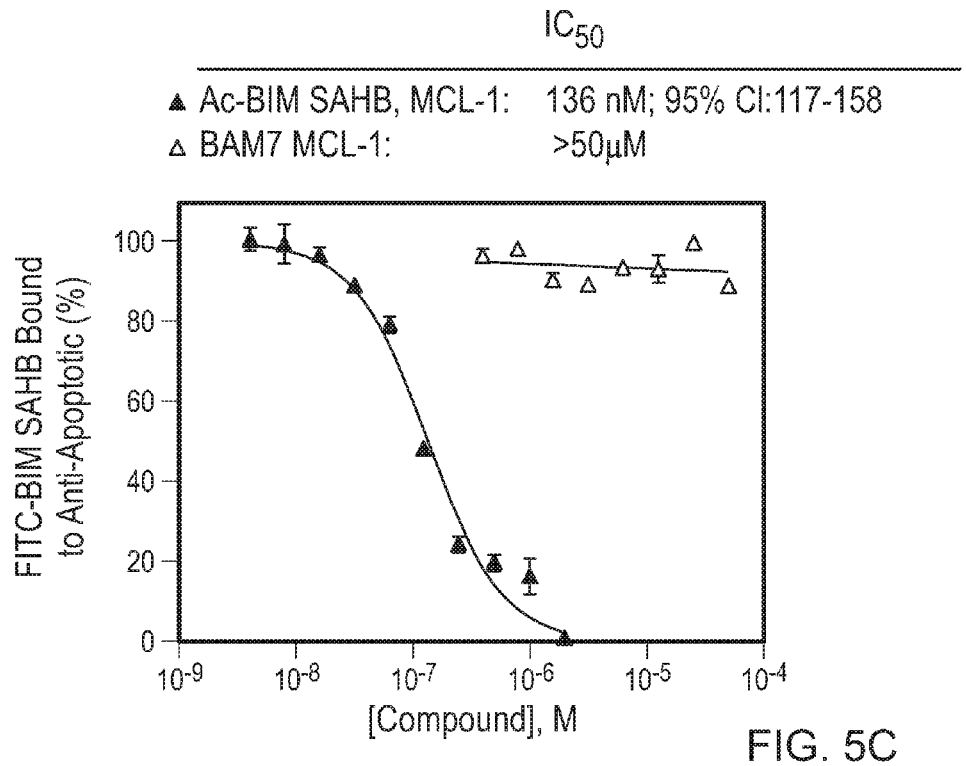
Figure 5D:
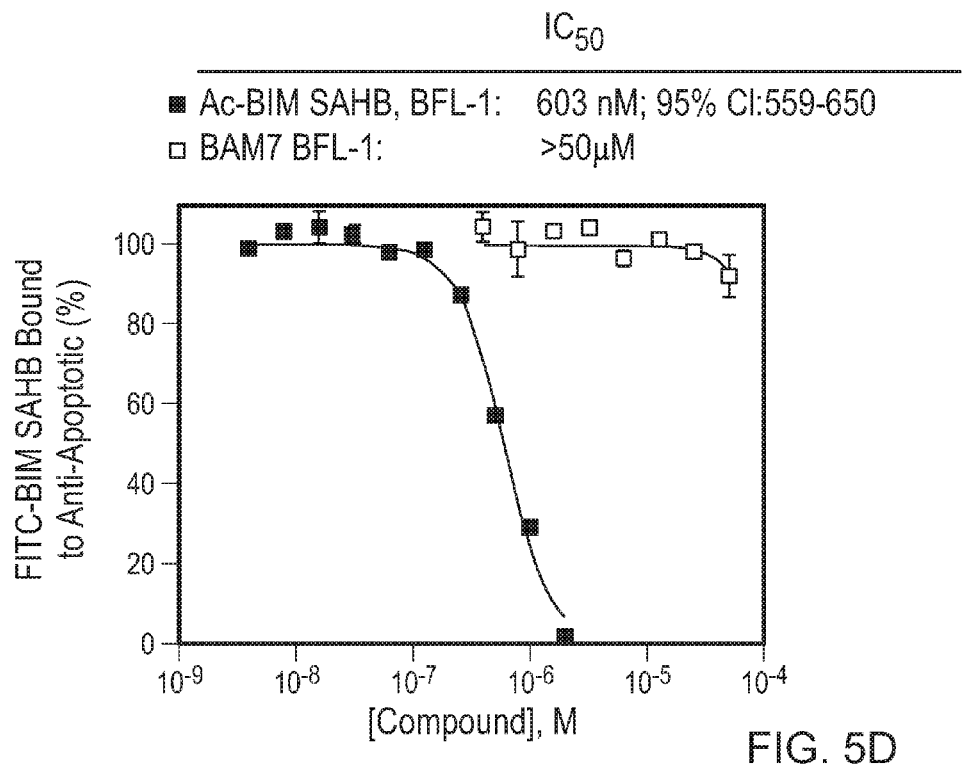

The BH3 binding pocket of anti-apoptotic targets shares topographic similarities with the BH3 trigger site on BAX, including a hydrophobic groove that engages the hydrophobic face of BH3 helices and a perimeter of similarly oriented charged and polar residues that are complementary to discrete residues of the hydrophilic BH3 interface. The two BH3 binding sites differ in their geographic location, pocket depth, and functionality. Whereas BIM BH3 is compatible with both the BAX trigger site and anti-apoptotic pockets, we examined whether BAM7 was selective for BCL-2 family targets by competitive FPA. As demonstrated for BAX, direct FPA analyses documented high affinity interactions between FITC-BIM SAHB and the anti-apoptotic proteins BCL-XL ($EC_{50}$, 13.6 nM), MCL-1 ($EC_{50}$, 19.8 nM), and BFL-1/A1 ($EC_{50}$, 17.9 nM), which represent the structural diversity of the pro-survival arm of the BCL-2 family (FIG. 5A). Correspondingly, the N-terminal acetylated analogue of BIM SAHB effectively competed with FITC-BIM SAHB for binding to BCL-XL ($IC_{50}$, 572 nM), MCL-1 ($IC_{50}$, 136 nM), and BFL-1/A1 ($IC_{50}$, 603 nM) (FIGS. 5B-5D). These binding data highlight that BIM SAHB can readily engage the diversity of apoptotic targets. In striking contrast, BAM7 exhibited little to no anti-apoptotic binding interactions even at 50 µM dosing, revealing a remarkable selectivity of BAM7 for BAX (FIGS. 4D and 5B-5D).

Example 3. Structural Analysis of the BAM7/BAX Interaction

To determine if BAM7 selectively competed with FITC-BIM SAHB for binding to BAX through a direct trigger site interaction or an indirect allosteric effect, we performed NMR analysis of $^{15}$N-BAX upon BAM7 titration. As observed for BIM $SAHB_A$[17], the addition of BAM7 up to a 1:1 ratio induced significant backbone amide chemical shift changes in those BAX residues concentrated in the region of the α1/α6 trigger site (FIG. 6A). These data are consistent with a direct interaction between BAM7 and BAX at the very surface employed by the BIM BH3 helix to trigger BAX activation.

Figure 6B:
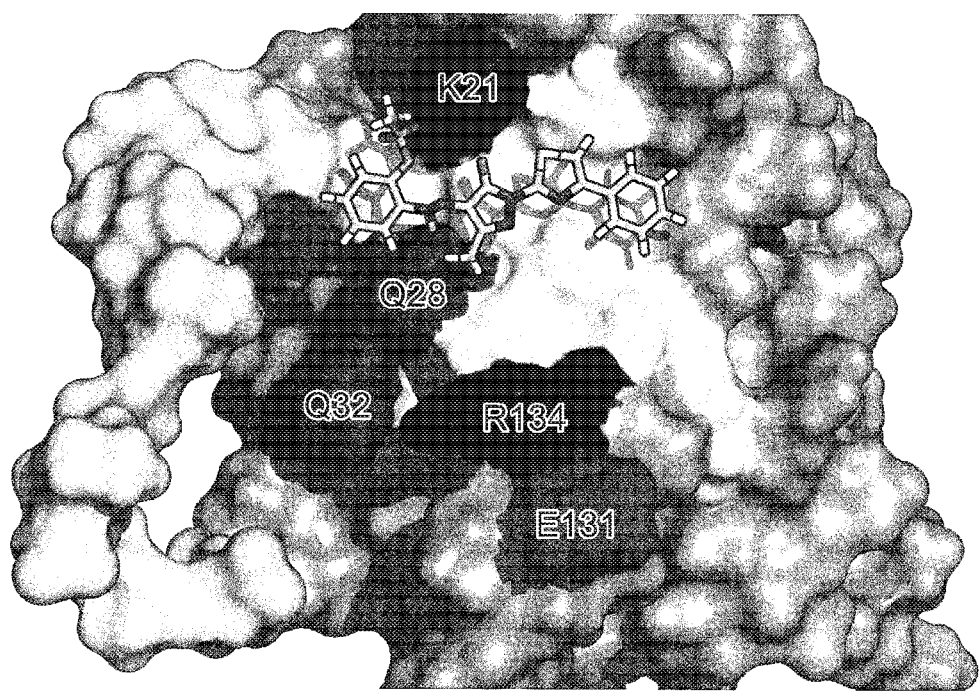
FIG. 6B is a structural depiction of the docked structure of BAM7 at the trigger site and predicts that the pyrazolone core of BAM7 sits at the base of the 6A7 activation epitope (amino acids 12-24), with the molecule's carbonyl group engaged in hydrogen bonding interactions with K21. The ethoxyphenyl group is positioned at the confluence of residues comprising the α1-α2 loop's C-terminus and the N-termini☐of α1 and α2, a presumed hinge region for loop opening upon initiation of direct BAX activation. The methyl and phenylthiazol R groups are predicted to make hydrophobic contact with aliphatic residues of α1 and α6, which also form a portion of the BIM BH3-binding groove.

We next performed molecular docking analysis to examine the predicted interactions between BAM7 and the BAX trigger site. Interestingly, BAM7 appears to insinuate itself along a crevice formed by residues located at (1) the junction between the α1-α2 loop's C-terminus and the N-terminus of α2, (2) the N-terminus of α1, and (3) the C-terminus of α6 (FIG. 6B). This is an intriguing model of the complex from a functional standpoint, as engagement of this region by BIM SAHB is believed to displace the α1-α2 loop and expose an epitope comprised of amino acids 12-24, which are recognized by the 6A7 antibody only upon BAX activation[21]. Indeed, the pyrazolone core of BAM7 sits at the base of the 6A7 activation epitope, with the carbonyl group engaged in hydrogen bonding interactions with K21, a key residue that participates in complementary charge-charge interactions with E158 of the BIM BH3 helix[11,17]. Whereas the ethoxyphenyl group abuts the confluence of residues at the α1-α2 loop's C-terminus and the N-termini of α1 and α2, a presumed hinge site for loop opening upon initiation of BAX activation, the methyl and phenylthiazol R groups make hydrophobic contact with that portion of the BIM BH3-binding groove formed by aliphatic residues of α1 and α6. Thus, docking analysis positions BAM7 at a critical region of the BAX trigger site implicated in ligand-induced α1-α2 loop displacement and resultant exposure of the 6A7 activation epitope. This binding region is geographically and functionally distinct from the canonical BH3-binding site located at the C-terminal face of anti-apoptotic BCL-2 family proteins, and may account for the remarkable selectivity of BAM7 for BAX.

Example 4. BAM7 Activates BAX and BAX-Dependent Cell Death

In order to transform from an inactive cytosolic monomer into a toxic mitochondrial oligomer, BAX undergoes a major conformational change upon BH3 triggering. We recently demonstrated using correlative structural and biochemical methods that these essential changes include "opening" of the α1/α2 loop, mobilization of the C-terminal α9 for mitochondrial translocation, and BAX BH3 exposure for propagating BAX activation[11]. To determine if the selective binding interaction we documented for BAM7 results in functional BAX activation, we performed a series of structural, biochemical, and cellular studies. First, we conducted an NMR analysis of $^{15}$N-BAX upon titration with higher concentrations of BAM7 to examine secondary structural changes that ensue upon ligand binding. We observed that increasing the ratio of BAM7/BAX from 1:1 to 2:1 caused additional chemical shift changes in the α1-α2 loop, the BH3 domain (α2), and in the C-terminal α9 helix, three discrete regions that also undergo allosteric changes in response to increased BIM SAHB exposure[11] (FIG. 7). To link these structural changes to the biochemical conversion of BAX from monomer to oligomer, we performed solution-phase BAX oligomerization assays in which BAX is exposed to increasing quantities of triggering ligand followed by monitoring of BAX species by size-exclusion chromatography over time. Like BIM SAHB[11], BAM7 triggered the conversion of BAX from monomer to oligomer in a dose- and time-responsive manner (FIG. 8A). To confirm that the SEC-based detection of BAM7-induced BAX oligomerization reflects functional activation of BAX for its release activity, we performed liposomal assays that explicitly evaluate the capacity of BAM7 to directly trigger BAX pore formation in the absence of other factors. Whereas treatment with BAX or BAM7 alone had no effect on the liposomes, the combination of BAM7 and BAX yielded dose-responsive liposomal release of entrapped fluorophore (FIG. 8B). Thus, the direct interaction between BAM7 and BAX at the trigger site induces the characteristic structural changes that yield functional BAX oligomerization.

Finally, we investigated whether this prototype BAX activator molecule that directly, selectively, and functionally activates BAX in vitro could induce BAX-dependent cell death. For these studies, we employed genetically-defined mouse embryo fibroblasts (MEFs) that either express only BAX (Bak$^{-/-}$), only BAK (Bax$^{-/-}$) or neither death effector (Bax$^{-/-}$Bak$^{-/-}$). Thus, to undergo apoptosis, MEFs rely on BAX and Bax$^{-/-}$ MEFs rely on BAK, whereas Bax$^{-/-}$Bak$^{-/-}$ MEFs are profoundly resistant to apoptosis[15]. Strikingly, BAM7 dose-responsively impaired the viability of Bak$^{-/-}$ MEFs that exclusively express BAX, but had no effect on Bax$^{-/-}$ MEFs that contain BAK but lack BAX (FIG. 8C). Similar specificity of action in Bak$^{-/-}$ MEFs was also observed for formula (I) compounds (FIG. 9A-D). BAM7-treated Bak$^{-/-}$ MEFs likewise exhibited characteristic microscopic features of apoptosis, including cellular shrinkage and membrane blebbing (FIG. 8E). Importantly, BAM7 did not affect the viability of Bax$^{-/-}$ Bak$^{-/-}$ MEFs, further confirming its specificity of action (FIG. 8C). To evaluate the cytosolic vs. mitochondrial distribution of BAX in response to BAM7 treatment, we transfected Bax$^{-/-}$Bak$^{-/-}$ MEFs with EGFP-BAX, labeled mitochondria with MitoTracker, and then monitored BAX translocation by confocal fluorescence microscopy. We observed a dose-responsive increase in BAX translocation as evidenced by conversion of the diffuse, cytosolic EGFP-BAX pattern to a mitochondrion-localized distribution (FIG. 8D).

Example 5. BAM7 Dose-Responsively Decreases Viability of DHL5 Diffuse Large B-Cell Lymphoma Cells (DLBCL) and Synergizes with the BCL-2/BCL-XL Inhibitor ABT-737

To assess the anti-cancer activity of BAM7, DHL5 DLBCL cells, which are relatively resistant to ABT-737, were exposed to BAM7 and dose-responsive impairment of cell viability was observed at 24 hours, as assessed by CellTiterGlo (FIG. 10A). Adding a subcytotoxic dose of the selective BCL-2/BCL-XL inhibitor ABT-737 further sensitized the cells to BAM7 (FIG. 10A). Conversely, BAM7 sensitized DHL5 cells to ABT-737 (FIG. 10B, 10C), which is otherwise less effective in DHL5 cells due to expression of anti-apoptotic proteins that lie outside its binding spectrum.

Thus, we find that BAM7 directly binds to the BAX trigger site and initiates the characteristic structural changes that lead to functional BAX activation. When applied to genetically-defined MEFs, BAM7 only kills the cell line that contains BAX, inducing the morphologic features of apoptosis; in the context of imaging Bax$^{-/-}$Bak$^{-/-}$ MEFs that express EGFP-BAX, BAX translocation from cytosol to mitochondria, and attendant cellular shrinkage and membrane blebbing, is also observed. BAM7 impairs the viability of DHL5 lymphoma cells and can sensitize the cells to the BCL-2/BCL-XL inhibitor AB7-737. Taken together, these studies demonstrate the feasibility of targeting BAX with a selective small molecule to trigger its pro-apoptotic activity.

Methods

In Silico Screening.

A diverse in silico library was generated from the following commercially available libraries downloaded from the ZINC database[34]: ACB Blocks, Asinex, Chembridge, Maybridge, Microsource, NCI, Peakdale, and FDA-approved. The in silico library was filtered for drug-like features, ADME properties, and appropriate functional groups with Qikprop. Molecules were converted to 3D all-atom structures, generating a maximum of 4 stereoisomers, ionization states for pH 7.0 and pH 2.0, and different tautomers with Ligprep. The database of in silico 3D molecules totaled approximately 750,000 compounds. BAX structures for docking were prepared using an averaged BAX closed-loop structure and an averaged BAX open-loop structure with GROMACS software. The two structures were generated in suitable format for docking with Maestro. Docking was performed using Glide, with the small molecule database for each BAX structure in standard precision mode (SPVS)[19]. The top 20,000 hits based on Glidescore function were selected and redocked to the BAX structures using extra precision docking mode (XPVS)[20]. The top 1000 hits from each docking calculation were visualized on the structure and then analyzed for interactions with key BAX residues, leading to selection of 100 compounds for experimental screening.

BCL-2 Family Protein Production.

Recombinant and tagless full-length BAX, BCL-X$_L$ΔC, MCL-1ΔNΔC, and BFL-1/A1ΔC were expressed and purified as previously reported[17,35]. Transformed *Escherichia coli* BL21 (DE3) were cultured in ampicillin-containing Luria Broth and protein expression was induced with 0.5 mM isopropyl β-D-1-thiogalactopyranoside (IPTG). The bacterial pellets were resuspended in buffer (250 mM NaCl, 20 mM Tris, complete protease inhibitor tablet, pH 7.2), sonicated, and after centifugation at 45,000×g for 45 min, the supernatants were applied to glutathione-agarose columns (Sigma) for GST-BCL-XLΔC, MCL-1ΔNΔC, and BFL-1/A1ΔC, or a chitin column (BioLabs) for Intein-BAX. On-bead digestion of GST-tagged protein was accomplished by overnight incubation at room temperature in the presence of thrombin (75 units) in PBS (3 mL), whereas the intein tag was cleaved from BAX by overnight incubation of the chitin beads at 4° C. with 50 mM DTT. BCL-X$_L$ΔC, MCL-1ΔNΔC, and BFL-1/A1ΔC were purified by size exclusion chromatography (SEC) using 150 mM NaCl, 50 mM Tris, pH 7.4 buffer conditions, and full-length monomeric BAX protein isolated by SEC using a Superdex-75 column (GE Healthcare) and 20 mM Hepes pH 7.2, 150 mM KCl buffer conditions.

Fluorescence Polarization Binding Assays.

Fluorescence polarization assays (FPA) were performed as previously described[35,36]. Briefly, direct binding curves were first generated by incubating FITC-BIM SAHB (50 nM) with serial dilutions of full-length BAX, BCL-X$_L$ΔC, MCL-1ΔNΔC, or BFL-1/A1ΔC and fluorescence polarization measured at 20 minutes on a SpectraMax M5 microplate reader (Molecular Devices). For competition assays, a serial dilution of small molecule or acetylated BIM SAHB (Ac-BIM SAHB) was combined with FITC-BIM SAHB (50 nM), followed by the addition of recombinant protein at ~EC$_{75}$ concentration, as determined by the direct binding assay (BAX: 500 nM; BCL-X$_L$ΔC, MCL-1ΔNΔC, BFL-1/A1ΔC: 200 nM). Fluorescence polarization was measured at 20 minutes and IC$_{50}$ values calculated by nonlinear regression analysis of competitive binding curves using Prism software (Graphpad).

BAM7 Characterization by Mass Spectrometry and $^1$H-NMR Spectroscopy.

4-(2-(2-ethoxyphenyl)hydrazono)-3-methyl-1-(4-phenyl thiazol-2-yl)-1H-pyrazol-5(4H)-one. LC-MS: ES+406 (M+1). $^1$H NMR (300 MHz, DMSO-d6) d 7.96 (d, 2H, J=8.1 Hz), 7.86 (s, 1H), 7.75 (d, 1H, J=7.8 Hz), 7.46 (t, 2H), 7.37-7.33 (m, 1H), 7.25-7.20 (m, 2H), 7.13-7.07 (m, 1H), 4.29-4.22 (q, 2H), 2.36 (s, 3H), 1.48 (t, 3H).

NMR Samples and Spectroscopy.

Uniformly $^{15}$N-labeled full-length human BAX was generated as previously described[17,37]. Protein samples were prepared in 25 mM sodium phosphate, 50 mM NaCl solution at pH 6.0 in 5% $D_2O$. BAM7 (10 mM stock) was titrated into a solution of 50 μM BAX to achieve the indicated molar ratios. Correlation $^1$H-$^{15}$N HSQC spectra[38] were acquired at 25° C. on a Bruker 800 MHz NMR spectrometer equipped with a cryogenic probe, processed using NMRPipe[39], and analyzed with NMRView[40]. The weighted average chemical shift difference Δ at the indicated molar ratio was calculated as $\sqrt{\{(\Delta H)^2+(\Delta N/5)^2\}/2}$ in p.p.m. The absence of a bar indicates no chemical shift difference, or the presence of a proline or residue that is overlapped or not assigned. BAX cross-peak assignments were applied as previously reported[37]. The significance threshold for backbone amide chemical shift changes was calculated based on the average chemical shift across all residues plus the standard deviation, in accordance with standard methods[41].

Structure Modeling.

Docked structures of BAX and BAM7 were generated using Glide 4.0[19,20] (Schrodinger, 2006) and analyzed using PYMOL[42].

BAX Oligomerization Assay.

BAM7 was added to a 200 □L solution (20 mM Hepes/KOH pH 7.2, 150 mM KCl, 0.5% CHAPS) containing size exclusion chromatography (SEC)-purified, monomeric BAX at the indicated BAM7:BAX ratios. The mixtures and BAX monomer alone were incubated at 30° C. for the indicated durations and then subjected to analysis by SEC using an SD75 column and 20 mM Hepes/KOH pH 7.2, 150 mM KCl running buffer. The monomeric and oligomeric fractions elute at ~11.5-12.0 min and ~6.5-7.5 min, respectively. Protein standards (GE Healthcare) were used to calibrate the molecular weights of gel filtration peaks. Replicates were performed using at least two independent preparations of freshly SEC-purified monomeric BAX protein.

Liposomal Release Assay.

Liposomes were prepared and release assays performed as previously described[32,43]. Liposomes were composed of the following molar percentages of lipids (Avanti Polar Lipids): phosphatidylcholine, 48%; phosphatidylethanolamine, 28%; phosphatidylinositol, 10%; dioleoyl phosphatidylserine, 10%; and tetraoleoyl cardiolipin, 4% and were loaded with ANTS/DPX (Molecular Probe) upon extrusion. BAX (400 nM) was combined with BAM7 (200 nM, 400 nM) in 96-well format (Corning) and then liposomes were added (10 μL, from 50 μM total lipid stock) in assay buffer (10 mM HEPES [pH 7], 200 mM KCl, 5 mM $MgCl_2$, and 0.2 mM EDTA) to a final volume of 100 Liposomal release was quantified based on the increase in fluorescence that occurs when the ANTS fluorophore is separated from the DPX quencher upon release from the liposomes into the supernatant. Fluorescence ($\lambda_{ex}$=355 nm and $\lambda_{em}$=520 nM) was measured for 2 hours at 30° C. using a Tecan Infinite M1000 plate reader. To measure maximal release, Triton X-100 was added to a final concentration of 0.2% (v/v) after 2 h and fluorescence measured for an additional 10 min. The percentage release of ANTS/DPX is calculated as percentage release=$((F-F_0)/(F_{100}-F_0))\times100$, where $F_0$ and $F_{100}$ are baseline and maximal fluorescence, respectively.

Cell Viability Assay.

Mouse embryonic fibroblasts (MEFs) cells were maintained in DMEM high glucose (Invitrogen) supplemented with 10% (v/v) FBS, 100 U/mL penicillin, 100 μg/mL streptomycin, 2 mM L-glutamine, 50 mM HEPES, 0.1 mM MEM non-essential amino acids and 50 μM β-mercaptoethanol MEFs ($2.5\times10^3$ cells/well) were seeded in 96-well opaque plates for 18-24 hours and then incubated with serial dilutions of BAM7 or vehicle (0.15% DMSO) in DMEM at 37° C. in a final volume of 100 μl. DHL5 cells were cultured as described (Deng et al. Cancer Cell, 12, 171-185, 2007) and subjected to vehicle, BAM7, ABT-737, and combinations thereof at the indicated doses. Cell viability was assayed at 24 hours by addition of CellTiter-Glo reagent according to the manufacturer's protocol (Promega), and luminescence measured using a SpectraMax M5 microplate reader (Molecular Devices). Viability assays were performed in at least triplicate and the data normalized to vehicle-treated control wells. Leukemia cell viability and caspase 3/7 assays were performed as described (Cohen et al, Chem Biol, 2012).

Light Microscopy.

MEFs (5,000 cells/well) were plated for 24 hours on glass bottom culture dishes (MatTek Corp., MA) and then incubated with BAM7 (15 μM) or vehicle (0.15% DMSO). Live cell imaging was performed using a TE2000-E2 Nikon microscopy equipped with a temperature and $CO_2$-controlled chamber that maintained an atmosphere of 3-5% humidified $CO_2$ at 37° C. A Hamamatsu Orca ER digital CCD camera was used to capture images at 20× magnification for 24 hours at 20 min intervals. Acquisition, hardware control, and image analysis was performed using Nikon NIS-Elements software.

BAX Translocation Assay.

MEFs were seeded on uncoated 24-well glass bottom plates at a density of $2.5\times10^5$ cells/well in 500 μL, of supplemented DMEM. After 6 hours, cells were transfected using Lipofectamine™ 2000 (Invitrogen) according to the manufacturer's protocol, using 750 ng of plasmid DNA and 1.0 μL, of Lipofectamine™ per well. Plasmid DNA was generated by cloning full-length BAX into the pEGFP-C3 plasmid (Clontech) using 5' PstI and 3' XbaI restriction sites. After overnight transfection, cells were treated with the indicated concentrations of BAM7 or vehicle (0.3% DMSO) in supplemented DMEM for 6 hours. Mitochondria were labeled with MitoTracker™ Red CMXRos (Invitrogen) according to the manufacturer's protocol using 20 nM probe in 500 μL supplemented, phenol red-free DMEM for 15 minutes. The cells were then incubated in fresh media for an addition 15 minutes prior to imaging. Confocal microscopy was performed using a Yokogawa spinning disk confocal microscope (Yokogawa Electric Corporation) equipped with a Nikon inverted Ti microscope. Solid state lasers set at 488 nm and 561 nm were used to visualize EGFP and MitoTracker® Red CMXRos, respectively. The plate temperature was maintained at 37° C. using an In Vivo environmental chamber (In Vivo Scientific). Images were collected using an Andor iXon DU-897 EM-CCD camera (Andor Technology) and analyzed with ImageJ software (NIH). Percent EGFP-positive cells was determined by counting EGFP-positive and Mitotracker-positive cells. Percent BAX translocation was calculated by dividing the number of cells containing mitochondrion-localized BAX by the total number of EGFP-positive cells. Each treatment was performed in quadruplicate with >200 cells counted per well.

Example 6. Additional Biological Activity

FIGS. 15A-15G are graphs that demonstrate the anti-leukemic activity of BAM7.

FIG. 16 is a graph that compares the anti-leukemic activity of BAM7 to compounds 165-93, 165-60, and 172-90 (see FIG. 14). Other comparative data is provided in the tables below:

| Compound | FITC-BIM SAHB Competition IC50 (µM) |
|---|---|
| BAM7 | 6 |
| 172-19 | 2.7 |
| 172-90 | 2 |
| 165-97 | 1.7 |
| 172-11 | 1.5 |

FIG. 17 is a graph that demonstrates the broad anti-leukemic activity of compound 172-90.

FIGS. 18A and 18B are graphs that demonstrate that compound 172-90 overcomes the apoptotic resistance conferred by BCL-2 family anti-apoptotic members BCL-XL and MCL-1; whereas the BCL-2/BCL-XL selective inhibitor ABT-737 induces cell death of the BCL-XL-dependent leukemia cell line, significant resistance to ABT-737 is manifest in the isogenic MCL-1 dependent leukemia cell line. In contrast, FIGS. 18C and 18D are graphs that demonstrate that compound 172-90 induces dose-responsive caspase 3/7 activity and cell death in both cell lines, overcoming formidable apoptotic resistance.

| Compound | FITC-BIM SAHB Competition IC50 (µM) |
|---|---|
| BAM7 | 6 |
| 161-79 | 6.2 |
| 183-50 | 2.5 |
| 165-60 | 0.9 |

| Compound | FITC-BIM SAHB Competition IC50 (µM) |
|---|---|
| BAM7 | 6 |
| 165-87 | 0.22 |
| 165-74 | 0.1 |

| Compound | FITC-BIM SABH Competition IC50 (µM) |
|---|---|
| BAM7 | 6 |
| 161-87 | 2.4 |
| 153-96 | 2 |
| 165-93 | 0.5 |

OTHER EMBODIMENTS

In some embodiments, compounds can have the 5,6 heteroring structure that is present in compounds 165-90, 165-94, and 165-95 in FIG. 11. In embodiments, the nitrogen in the 6-membered ring adjacent to the carbonyl can be substituted with X-Y in which X and Y can be as defined anywhere herein; and the remaining positions can be substituted with substituents as defined in $R^2$ as defined anywhere herein.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A compound of Formula (I-A):

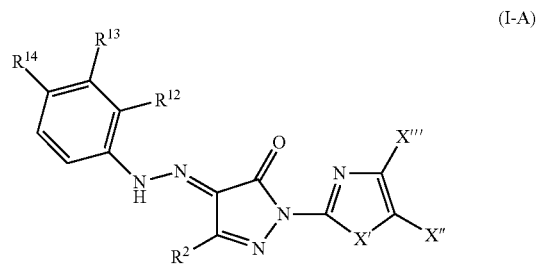

(I-A)

or a pharmaceutically acceptable salt thereof, wherein:
X' is S;
X" is H or $C_1$-$C_4$ alkyl;
X''' is unsubstituted heteroaryl, which contains from 5-6 ring atoms, wherein 1 or 2 of the ring atoms is independently selected from N and S;
$R^2$ is:
(i) $C_{1-4}$ alkyl; or
(ii) unsubstituted heteroaryl containing from 5-6 ring atoms, wherein 1, 2, 3, or 4 of the ring atoms is independently selected from N, NH, N($C_1$-$C_3$ alkyl), NC(O)($C_1$-$C_6$ alkyl), O, and S;
$R^{12}$ is selected from the group consisting of H, methoxy, phenoxy, benzyloxy, C(=O)$C_{1-4}$ alkoxy, and —C(=O)—($C_{1-4}$ alkoxy)-C(=O)-(phenyl);
$R^{13}$ is selected from the group consisting of H and $C_{2-4}$ alkoxy;
$R^{14}$ is selected from the group consisting of H, $C_{1-4}$ alkyl, $C_{1-4}$ alkoxy, NHC(=O)$C_{1-4}$ alkyl, and C(=O)$C_{1-4}$ alkoxy; and
wherein at least one of $R^{12}$, $R^{13}$, and $R^{14}$ is not H.

2. The compound of claim 1, wherein $R^2$ is $C_{1-4}$ alkyl.

3. A compound of Formula (I-A):

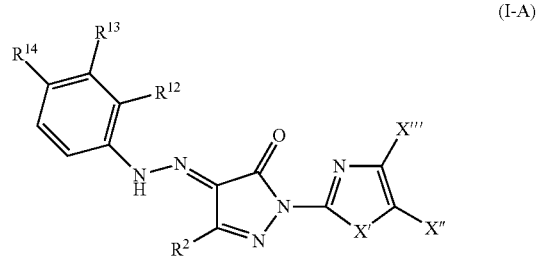

(I-A)

or a pharmaceutically acceptable salt thereof, wherein:
X' is S;
X" is H or $C_1$-$C_4$ alkyl;

X''' is:
(i) $C_6$-$C_{10}$ aryl, which is optionally substituted with 1, 2, 3, 4, or 5 independently selected $R^b$ groups; or
(ii) heteroaryl, which contains from 5-10 ring atoms, wherein 1, 2, 3, or 4 of the ring atoms is independently selected from N, NH, N($C_1$-$C_3$ alkyl), O, and S; and wherein said heteroaryl ring is optionally substituted with 1, 2, or 3 independently selected $R^b$ groups;
$R^2$ is heteroaryl containing from 5-6 ring atoms, wherein 1 or 2 of the ring atoms is independently selected from N and S;
$R^{12}$ is selected from the group consisting of H, methoxy, phenoxy, benzyloxy, C(=O)$C_{1-4}$ alkoxy, and —C(=O)—($C_{1-4}$ alkoxy)-C(=O)-(phenyl);
$R^{13}$ is selected from the group consisting of H and $C_{2-4}$ alkoxy;
$R^{14}$ is selected from the group consisting of H, $C_{1-4}$ alkyl, $C_{1-4}$ alkoxy, NHC(=O)$C_{1-4}$ alkyl, and C(=O)$C_{1-4}$ alkoxy;
wherein at least one of $R^{12}$, $R^{13}$, and $R^{14}$ is not H; and
$R^b$ is $C_{1-4}$ alkoxy.

4. The compound of claim 1, wherein $R^{12}$ is selected from the group consisting of H, methoxy, phenoxy, benzyloxy, —C(=O)OCH$_2$CH$_3$, and —C(=O)OCH$_2$C(=O)-phenyl.

5. The compound of claim 1, wherein $R^{13}$ is H or ethoxy.

6. The compound of claim 1, wherein $R^{14}$ is selected from the group consisting of H, methyl, methoxy, ethoxy, —NHC(=O)CH$_3$, and C(=O)OCH$_2$CH$_3$.

7. A compound which is selected from the group consisting of:

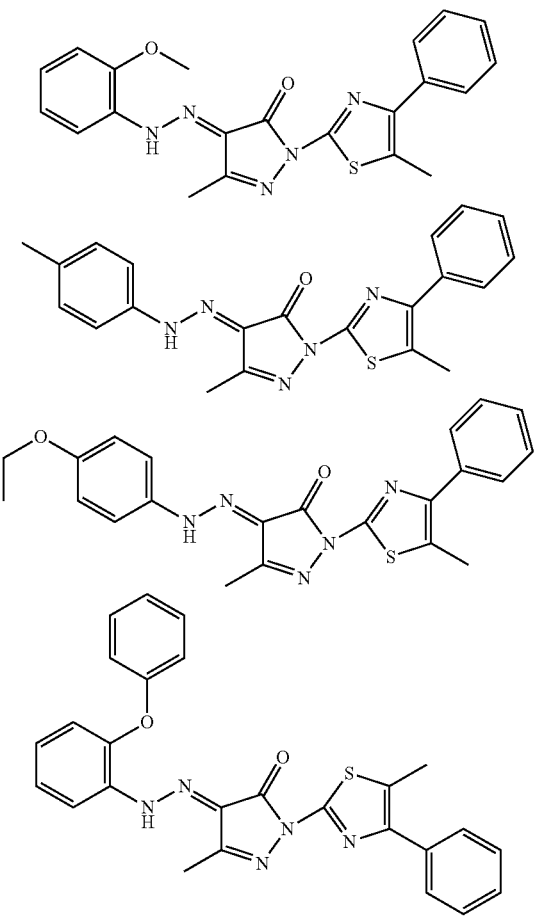

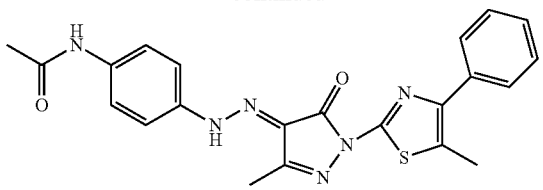

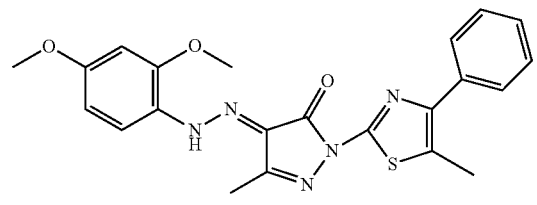

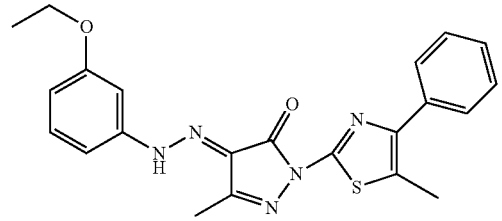

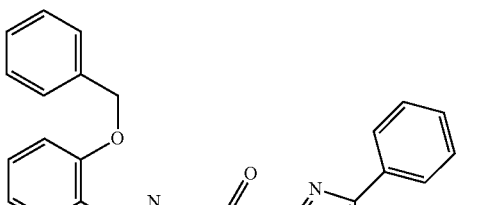

and

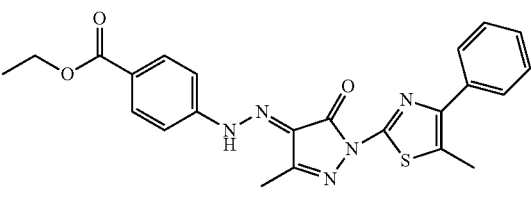

;

or a pharmaceutically acceptable salt thereof.

8. A pharmaceutical composition comprising a compound of claim 1, or a pharmaceutically acceptable salt thereof, and a pharmaceutically acceptable carrier.

9. A method of treating cancer in a subject, comprising administering the compound of claim 1, or a pharmaceutically acceptable salt thereof, to a subject in need of cancer treatment in an amount effective to treat the cancer, wherein the cancer is leukemia.

10. The method of claim 9, wherein the leukemia is selected from the group consisting of acute lymphoblastic leukemia (ALL) and acute myelogenous leukemia (AML).

11. A method of activating a pro-apoptotic function of BAX in a cell or tissue containing BAX, comprising contacting the cell or tissue with a compound of claim 1, or a pharmaceutically acceptable salt thereof.

12. A compound, which is selected from the group consisting of:

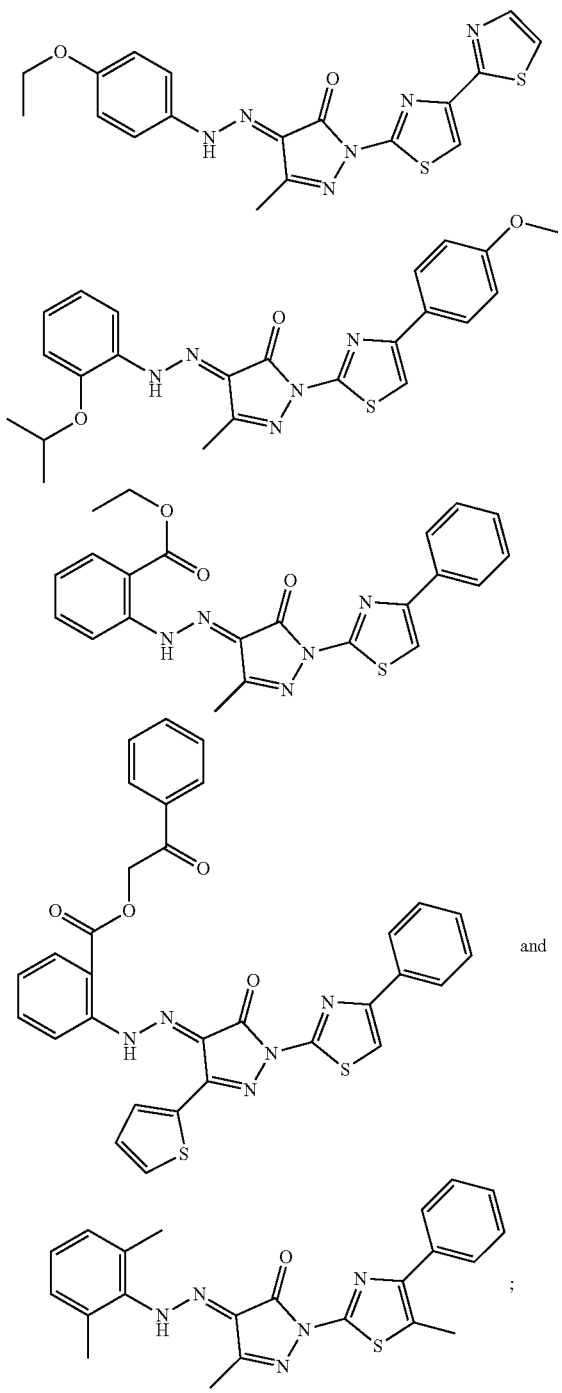

or a pharmaceutically acceptable salt thereof.

13. A pharmaceutical composition comprising a compound of claim 12, or a pharmaceutically acceptable salt thereof, and a pharmaceutically acceptable carrier.

14. The compound of claim 3, wherein $R^2$ is thienyl.

15. The compound of claim 3, wherein $R^{12}$ is selected from the group consisting of H, methoxy, phenoxy, benzyloxy, —C(═O)OCH$_2$CH$_3$, and —C(═O)OCH$_2$C(═O)-phenyl.

16. The compound of claim 3, wherein $R^{13}$ is H or ethoxy.

17. The compound of claim 3, wherein $R^{14}$ is selected from the group consisting of H, methyl, methoxy, ethoxy, —NHC(═O)CH$_3$, and C(═O)OCH$_2$CH$_3$.

18. A pharmaceutical composition comprising a compound of claim 3, or a pharmaceutically acceptable salt thereof, and a pharmaceutically acceptable carrier.

19. A pharmaceutical composition comprising a compound of claim 7, or a pharmaceutically acceptable salt thereof, and a pharmaceutically acceptable carrier.

20. A method of treating cancer in a subject, comprising administering the compound of claim 3, or a pharmaceutically acceptable salt thereof, to a subject in need of cancer treatment in an amount effective to treat the cancer, wherein the cancer is leukemia.

21. The method of claim 20, wherein the leukemia is selected from the group consisting of acute lymphoblastic leukemia (ALL) and acute myelogenous leukemia (AML).

22. A method of activating a pro-apoptotic function of BAX in a cell or tissue containing BAX, comprising contacting the cell or tissue with a compound of claim 3, or a pharmaceutically acceptable salt thereof.

23. A method of treating cancer in a subject, comprising administering the compound of claim 7, or a pharmaceutically acceptable salt thereof, to a subject in need of cancer treatment in an amount effective to treat the cancer, wherein the cancer is leukemia.

24. The method of claim 23, wherein the leukemia is selected from the group consisting of acute lymphoblastic leukemia (ALL) and acute myelogenous leukemia (AML).

25. A method of activating a pro-apoptotic function of BAX in a cell or tissue containing BAX, comprising contacting the cell or tissue with a compound of claim 7, or a pharmaceutically acceptable salt thereof.

26. A method of treating cancer in a subject, comprising administering the compound of claim 12, or a pharmaceutically acceptable salt thereof, to a subject in need of cancer treatment in an amount effective to treat the cancer, wherein the cancer is leukemia.

27. The method of claim 26, wherein the leukemia is selected from the group consisting of acute lymphoblastic leukemia (ALL) and acute myelogenous leukemia (AML).

28. A method of activating a pro-apoptotic function of BAX in a cell or tissue containing BAX, comprising contacting the cell or tissue with a compound of claim 12, or a pharmaceutically acceptable salt thereof.

* * * * *

UNITED STATES PATENT AND TRADEMARK OFFICE
CERTIFICATE OF CORRECTION

PATENT NO. : 10,000,478 B2  
APPLICATION NO. : 15/048918  
DATED : June 19, 2018  
INVENTOR(S) : Loren D. Walensky and Evripidis Gavathiotis Page 1 of 2

It is certified that error appears in the above-identified patent and that said Letters Patent is hereby corrected as shown below:

In the Drawings

Figure 19A:
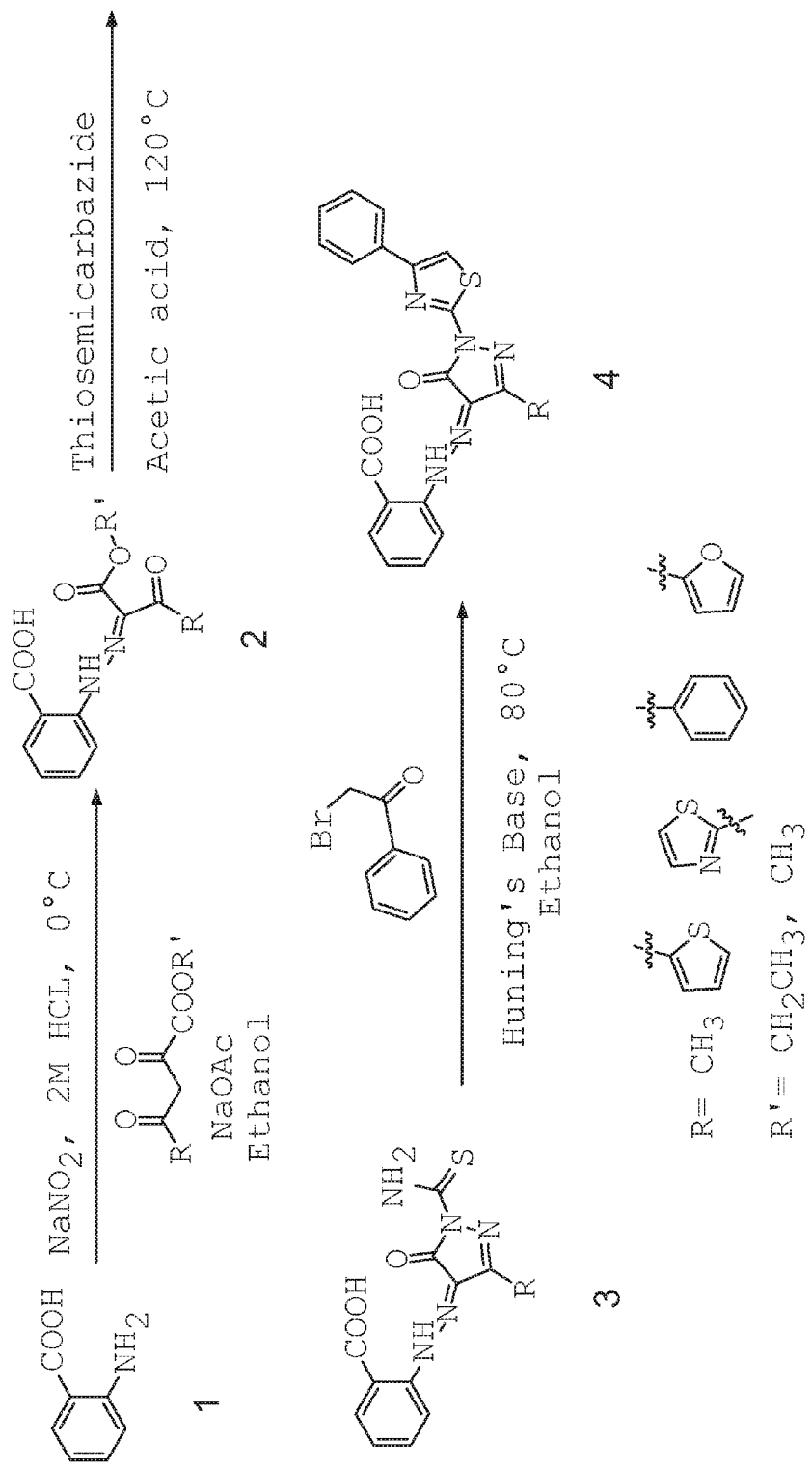

FIG. 19A: Delete "Huning's" and insert -- Hunig's -- therefor.

Figure 19B:
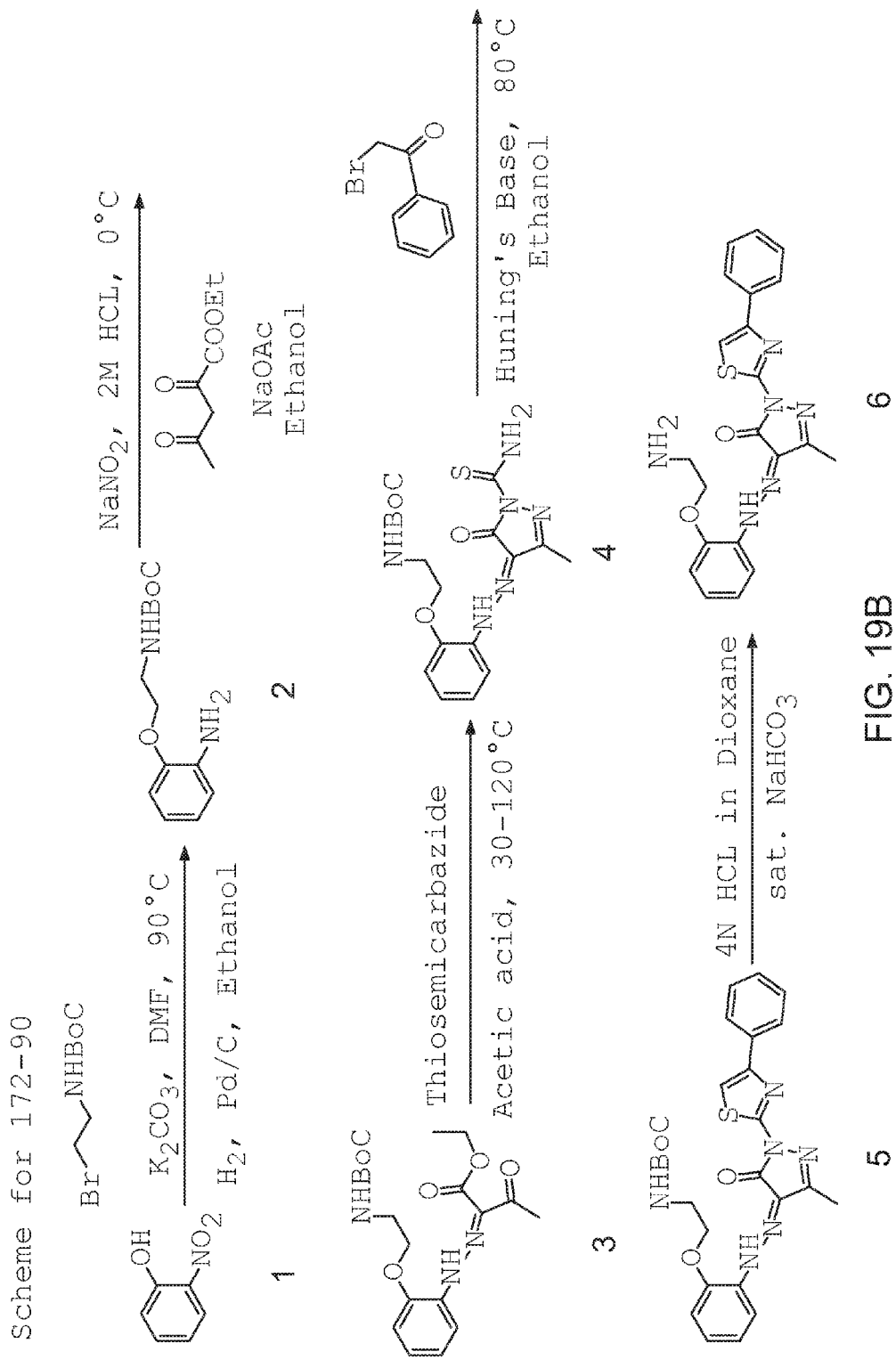

FIG. 19B: Delete "Huning's" and insert -- Hunig's -- therefor.

Figure 19C:
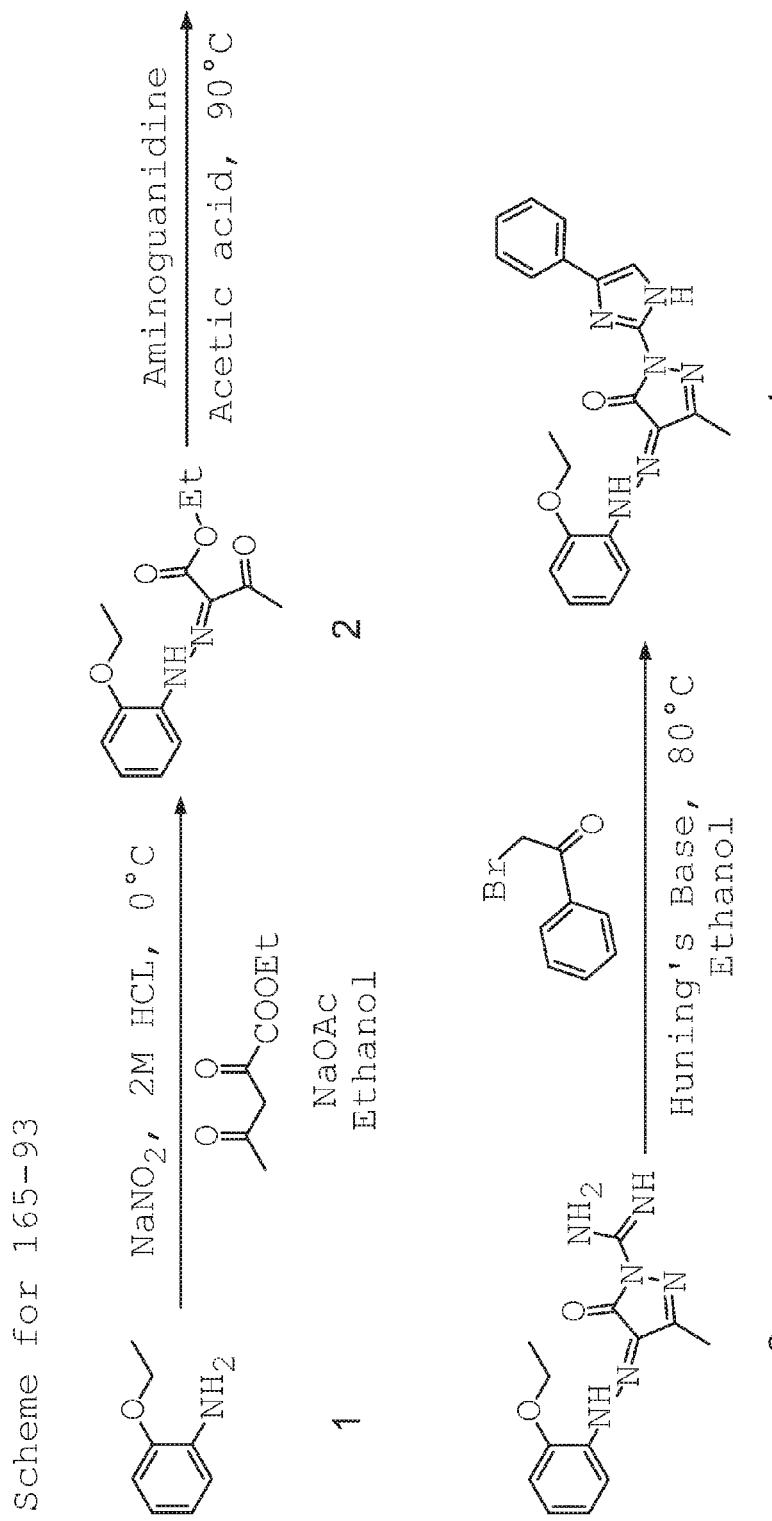

FIG. 19C: Delete "Huning's" and insert -- Hunig's -- therefor.

Figure 19D:
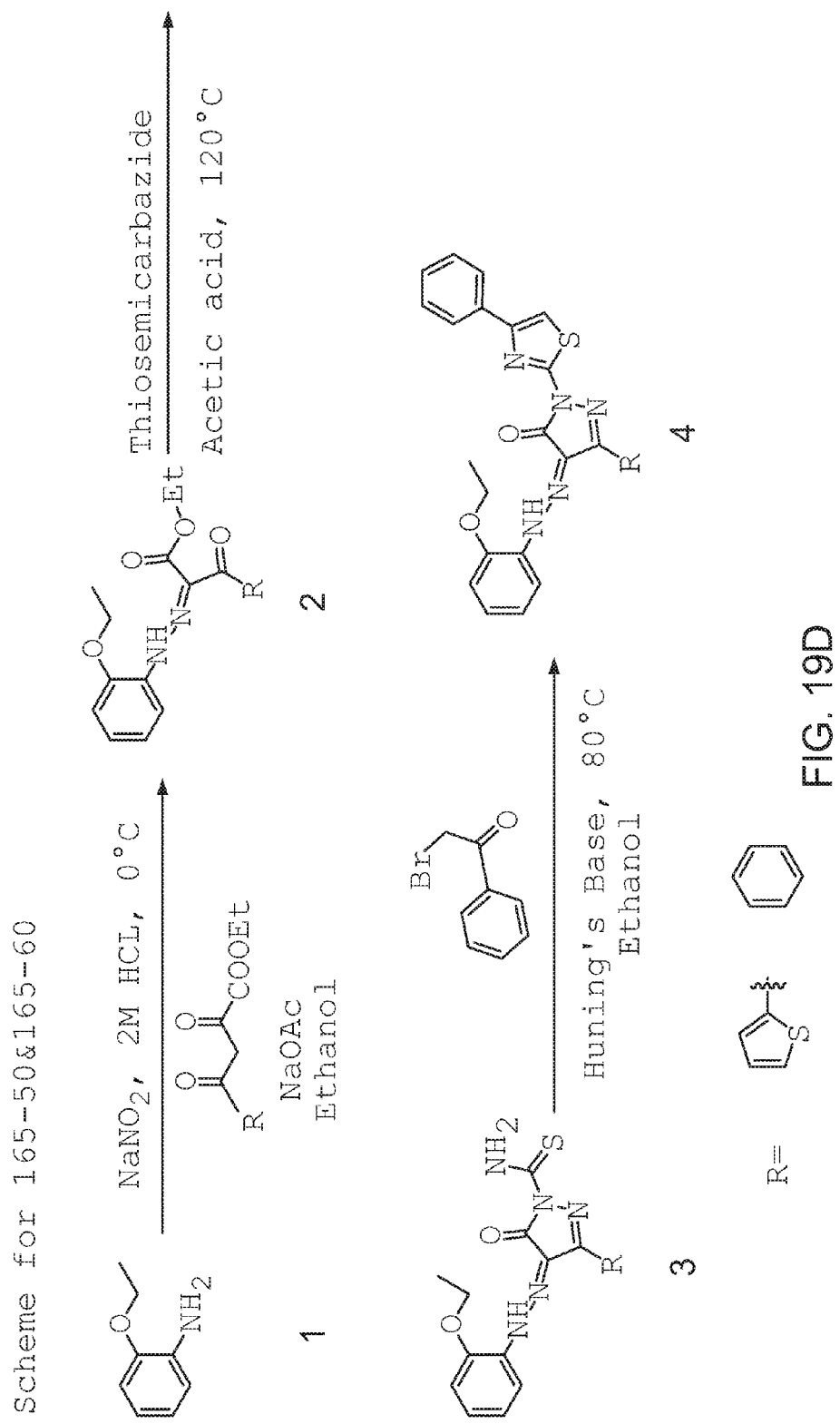

FIG. 19D: Delete "Huning's" and insert -- Hunig's -- therefor.

Figure 19E:
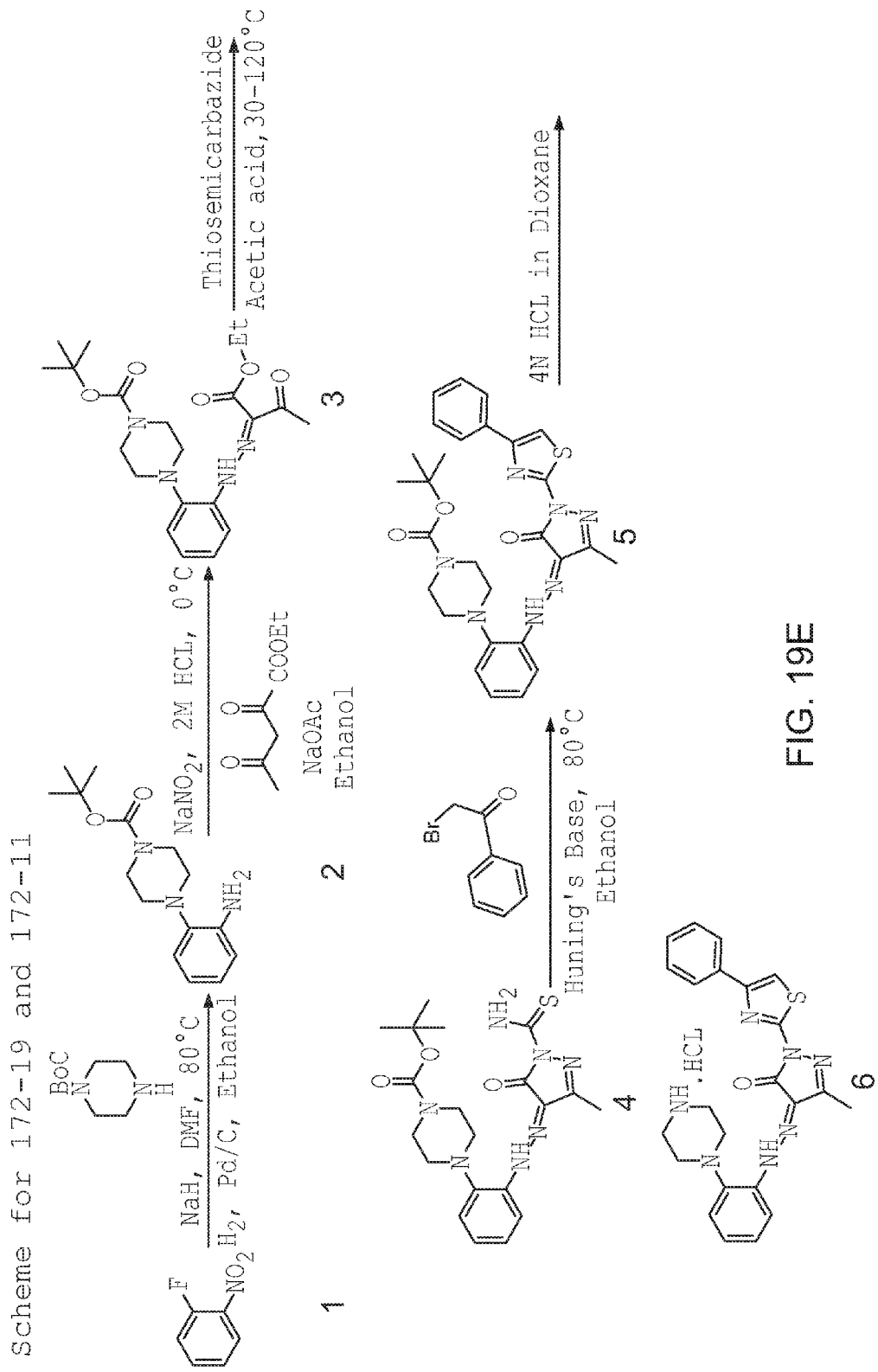
Figure 19F:
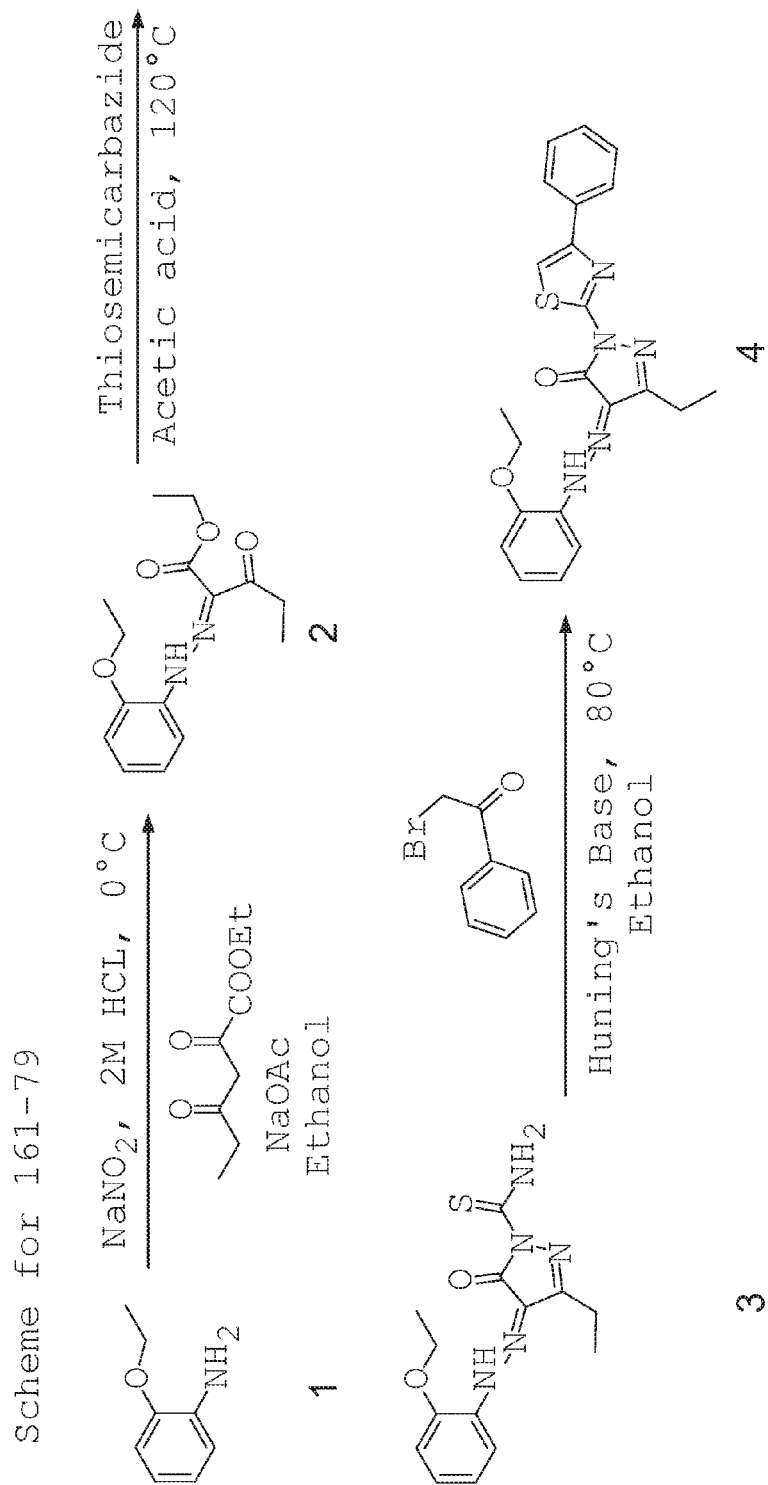

FIG. 19E: Delete "Huning's" and insert -- Hunig's -- therefor.

In the Specification

Column 1, Line 47: Delete "proapoptotic" and insert -- pro-apoptotic -- therefor.

Column 1, Line 62: Delete "Proapoptotic" and insert -- Pro-apoptotic -- therefor.

Column 3, Line 30: Delete "L27" and insert -- L25 -- therefor.

Column 3, Line 30: Delete "I133".

Column 3, Lines 38-39: Delete "proapoptotic" and insert -- pro-apoptotic -- therefor.

Column 3, Line 42: Insert -- . -- after "site"".

Column 3, Line 61: Insert -- . -- after "(I-A))".

Column 9, Line 52: Delete "proteosome" and insert -- proteasome -- therefor.

Signed and Sealed this  
Twenty-sixth Day of March, 2019

Andrei Iancu  
*Director of the United States Patent and Trademark Office*

CERTIFICATE OF CORRECTION (continued)
U.S. Pat. No. 10,000,478 B2

Column 10, Line 10: Delete "aminoglutethamide" and insert -- aminoglutethimide -- therefor.

Column 13, Line 30: Delete "cya nines" and insert -- cyanines -- therefor.

Column 21, Line 43: Delete "substitutents" and insert -- substituents -- therefor.

Column 23, Line 28: Delete "cycloakyl" and insert -- cycloalkyl -- therefor.

Column 25, Line 13: Delete "N-termini▢" and insert -- N-termini -- therefor.

Column 37, Line 67: Delete "palmoate" and insert -- pamoate -- therefor.

Column 39, Line 42: Delete "chromatograpy" and insert -- chromatography -- therefor.

Column 40, Line 43: Delete "losenges" and insert -- lozenges -- therefor.

Column 42, Line 59: Delete "and or" and insert -- and/or -- therefor.

Column 47, Line 64: Delete "AB7-737" and insert -- ABT-737 -- therefor.

Column 48, Line 36: Delete "centifugation" and insert -- centrifugation -- therefor.

Column 49, Line 34: Delete "▢L" and insert -- µL -- therefor.

Column 51, Line 55: Delete "SABH" and insert -- SAHB -- therefor.